(12) United States Patent
Bathe et al.

(10) Patent No.: US 7,160,711 B2
(45) Date of Patent: Jan. 9, 2007

(54) CORYNEFORM BACTERIA WHICH PRODUCE CHEMICAL COMPOUNDS I

(75) Inventors: Brigitte Bathe, Salzkotten (DE); Caroline Kreutzer, Melle (DE); Bettina Mockel, Dusseldorf (DE); Georg Thierbach, Bielefeld (DE)

(73) Assignee: Degussa AG, Dusseldorf (DE)

( * ) Notice: Subject to any disclaimer, the term of this patent is extended or adjusted under 35 U.S.C. 154(b) by 347 days.

(21) Appl. No.: 10/358,405

(22) Filed: Feb. 5, 2003

(65) Prior Publication Data
US 2003/0219881 A1 Nov. 27, 2003

Related U.S. Application Data

(63) Continuation-in-part of application No. PCT/EP02/08464, filed on Jul. 30, 2002.

(60) Provisional application No. 60/309,878, filed on Aug. 6, 2001.

(51) Int. Cl.
*C12N 1/12* (2006.01)
*C12N 15/00* (2006.01)

(52) U.S. Cl. .................... 435/252.3; 435/320.1

(58) Field of Classification Search ............. 435/252.3, 435/320.1
See application file for complete search history.

(56) References Cited

U.S. PATENT DOCUMENTS

| 5,700,661 A | * | 12/1997 | Katsumata et al. ........ 435/69.1 |
| 6,180,373 B1 | | 1/2001 | Wich et al. |
| 2003/0049804 A1 | | 3/2003 | Pompejus et al. |
| 2003/0219881 A1 | | 11/2003 | Brigitte et al. |

FOREIGN PATENT DOCUMENTS

| BE | 898864 | 8/1984 |
| EP | 0 974 666 A1 | 1/2000 |
| EP | 1 067 192 | 1/2001 |
| EP | 1 094 111 A2 | 4/2001 |
| EP | 1 108 790 A2 | 6/2001 |
| EP | 1 111 062 A1 | 6/2001 |
| EP | 1 172 437 | 1/2002 |
| WO | WO 91/13990 | 9/1991 |
| WO | WO 00 63388 | 10/2000 |
| WO | WO 01/09351 A1 | 2/2001 |
| WO | WO 03/014330 A2 | 2/2003 |
| WO | WO 03/040373 A2 | 5/2003 |

OTHER PUBLICATIONS

Kronemeyer et al., "Structure of the gluABCD cluster encoding the glutamate uptake system of cornebacterium glutamicum", Journal of Bacteriology, vol. 177, No. 5, 1995, pp. 1152-1158.

Ishino et al., "Nucleotide sequence of the meso-diaminopimelate D-dehydrogenase gene from corynebacterium glutamicum", Nucleic Acids Research, vol. 15, No. 9, 1987, p. 3917.

Schafer et al, "Small mobilizable multi-purpose cloning vectors derived from the *E. coli* plasmids pk18 and pk19: selection of defined deletions in the chromosome of corynebacterium glutamicum", Gene, vol. 145, No. 1, 1994, p. 69-73.

S. Moreau, "Prophage distributing in coryneform bacteria," Res. Microbiol., Institut Pasteur/Elsevier, p. 493-505, 1995.

Eikmanns et al., "Molecular aspects of lysine, threonine, and isoleucine biosynthesis in *Corynebacterium glutamicum*," Antonie van Leeuwenhoek, 20th ed., Kluwer Academic Publishers (The Netherlands), p. 145-163, (1993).

Rappuoli, "Integration of Corynbacteriophages Btox+, xtox+, and ytox− into Two Attachment Sites on the *Corynebacterium diphtheriae* Chromosome," Journal of Bacteriology, Americna Society for Microbiology, vol. 153 (No. 3), p. 1202-1210, 1983.

Adham et al., "Construction of a Xylanase-Producing Strain of Brevibacterium lactofermentum by Stable Integration of an Engineered xysA Gene from *Streptomyces halstedii* JM8," Applied and Environmental Microbiology, American Society for Microbiology, vol. 67 (No. 12), p. 5425-5430, (Dec. 2001).

Schwarzer et al., "Manipulation of *Corynebacterium glutamicum* by Gene Disruption and Replacement," *BIOTECHNOLOGY*, vol. 9 (No. 01), p. 84-87, (1991).

Correia et al., "Targeted integration of foreign genes into repetitive sequences of the *Brevibacterium lactofermentum* chromosome," IFEMS Microbiology Letters, p. 295-264, ( 1996).

Reinscheid et al., "Stable Expression of hom-1-thrB in *Corynebacterium glutamicum* and its Effect on the Carbon Glux to Threonine and Related Amino Acids," Applied and Environmental Microbiology, American Society for Microbiology, vol. 60 (No. 1), p. 126-132, ( 1994).

Jetten et al., "Effect of different levels of aspartokinase on the lysine production by *Corynebacterium lactofermentum*," Appl. Microbiol. Biotechnol., p. 76-82, ( 1995).

\* cited by examiner

*Primary Examiner*—Mark Navarro
(74) *Attorney, Agent, or Firm*—Pillsbury Winthrop Shaw Pittman LLP

(57) ABSTRACT

The invention relates to coryneform bacteria which have, in addition to at least one copy, present at the natural site (locus), of an open reading frame (ORF), gene or allele which codes for the synthesis of a protein or an RNA, in each case a second, optionally third or fourth copy of this open reading frame (ORF), gene or allele at in each case a second, optionally third or fourth site in a form integrated into the chromosome and processes for the preparation of chemical compounds by fermentation of these bacteria.

16 Claims, 7 Drawing Sheets

Figure 1: Plasmid pK18mobsacBglu1_1
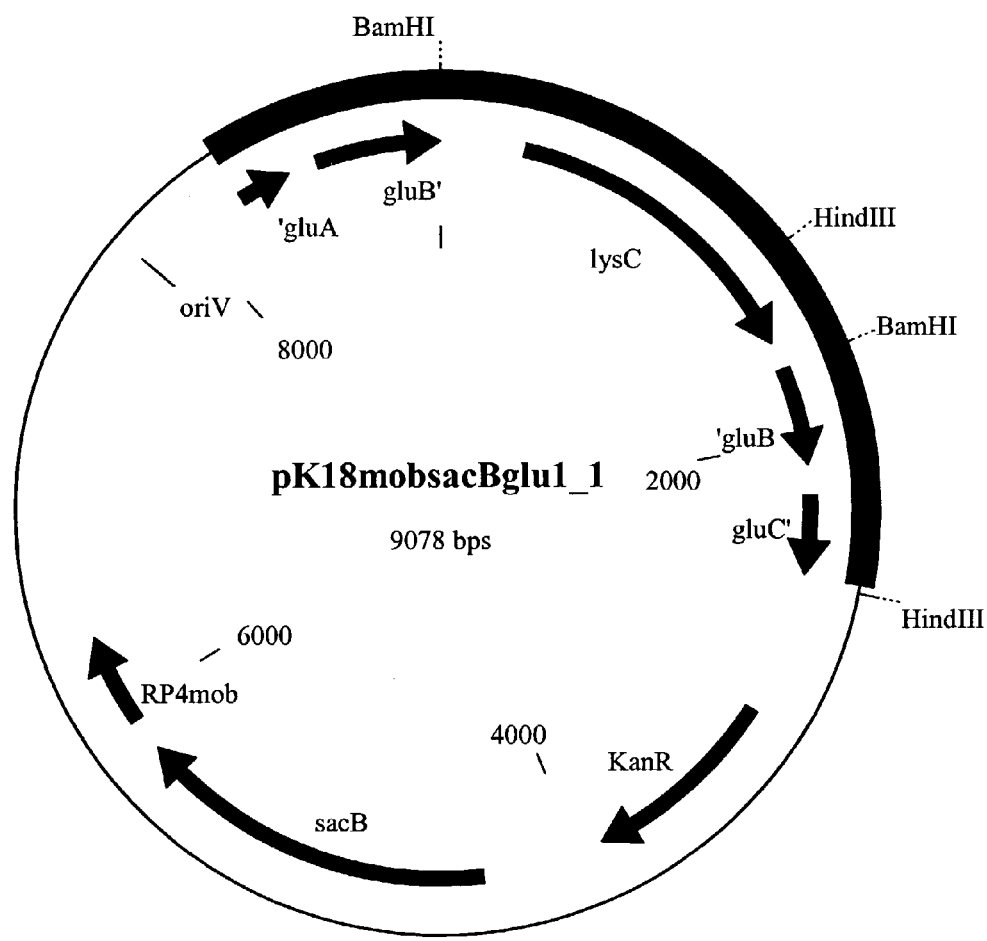

Figure 2: Plasmid pK18mobsacBaecD1_1
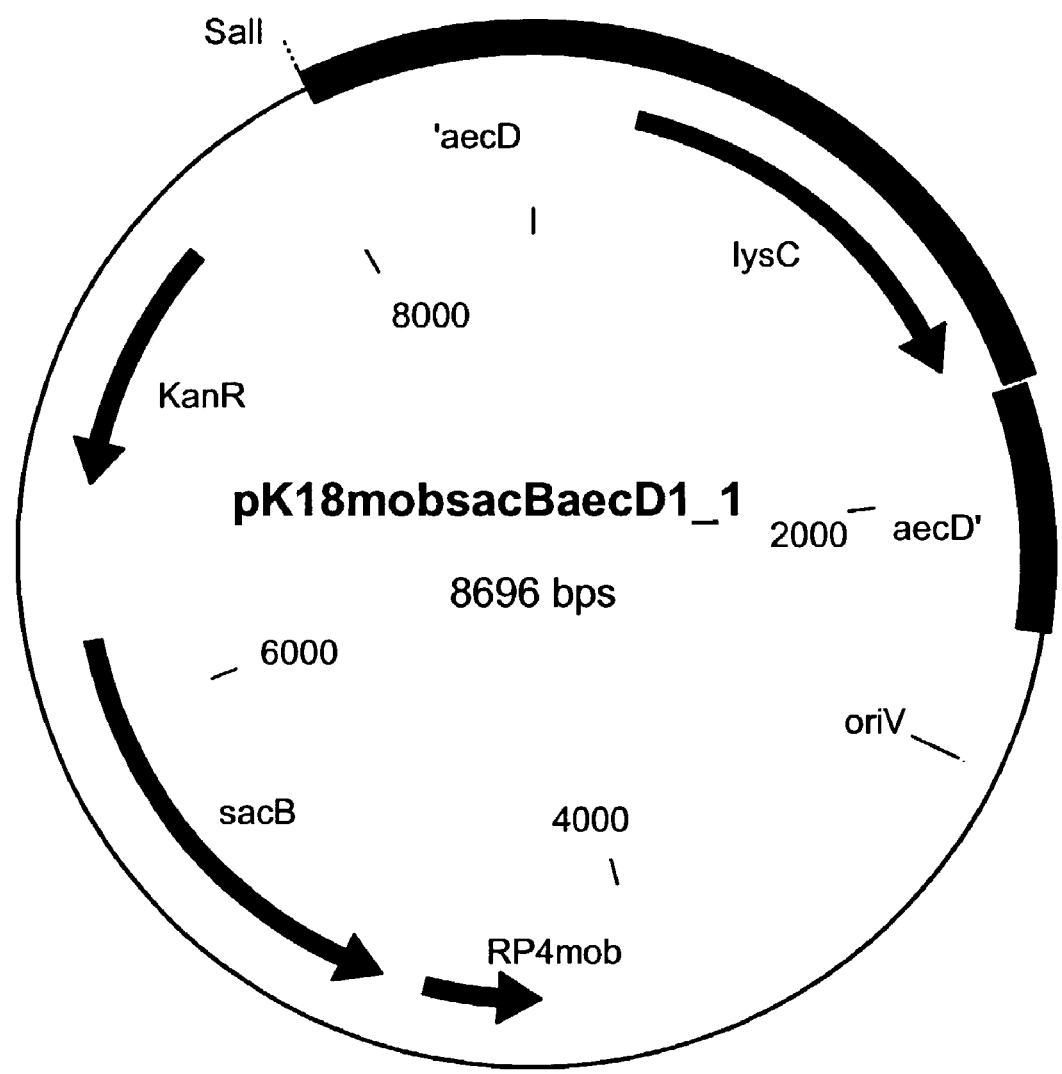

Figure 3: Plasmid pK18mobsacBpck1_1
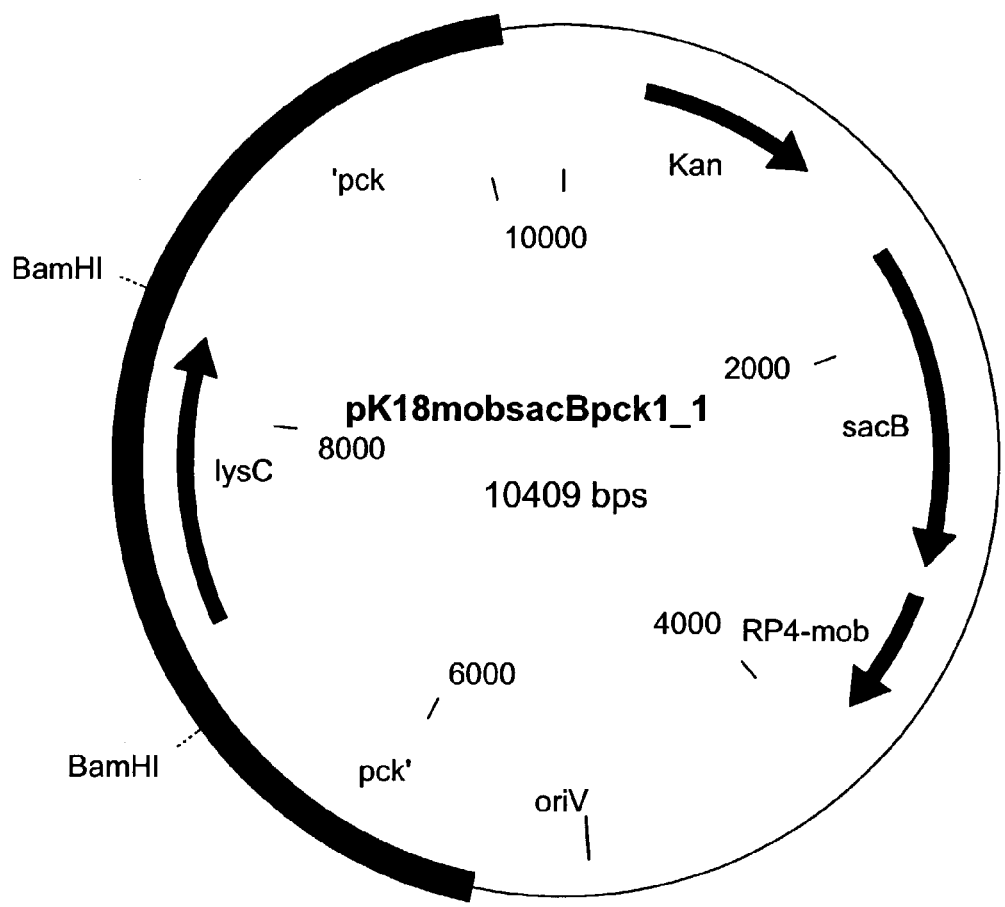

Figure 4: Plasmid pK18mobsacBgluB2_1
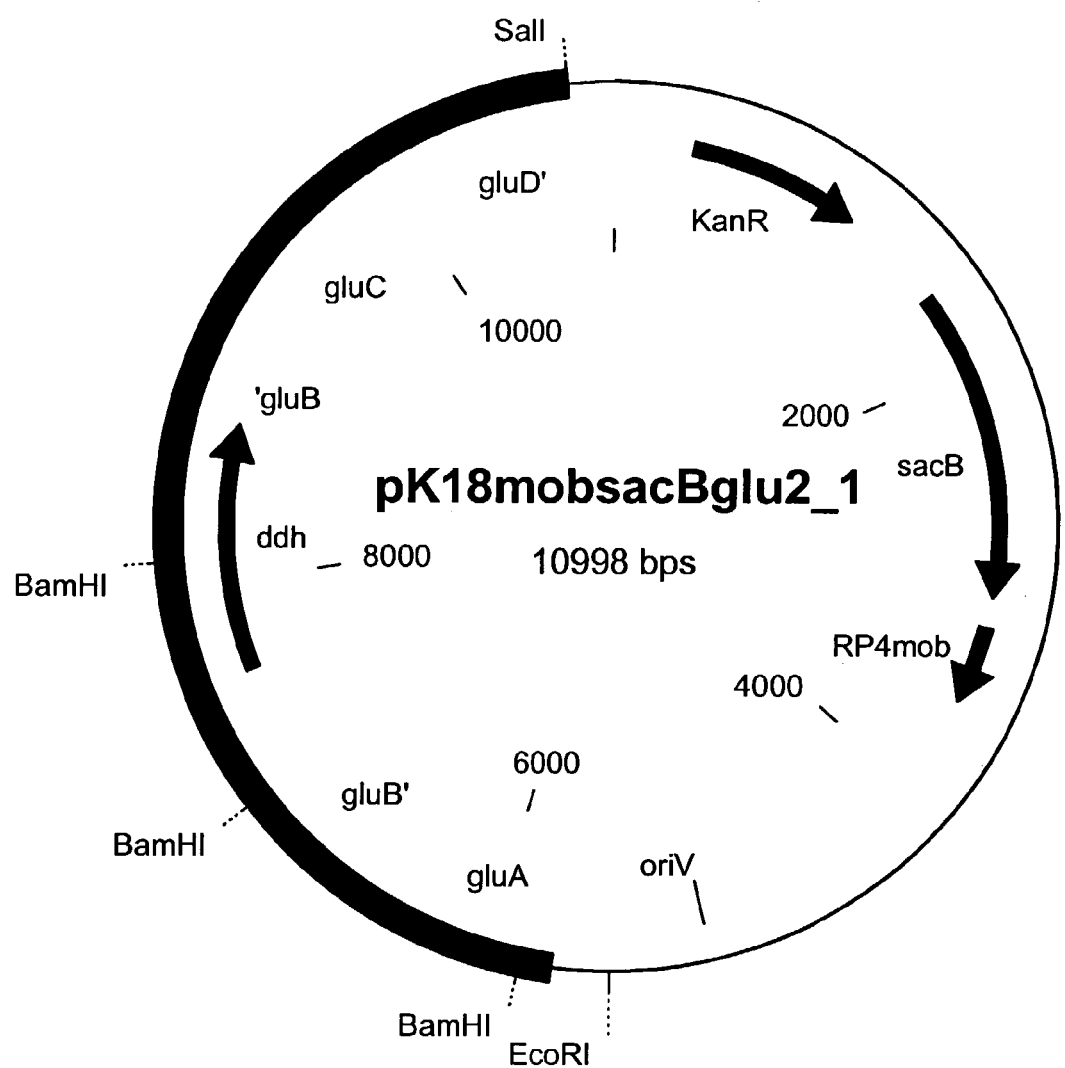

Figure 5: Plasmid pK18mobsacBaecD2_1
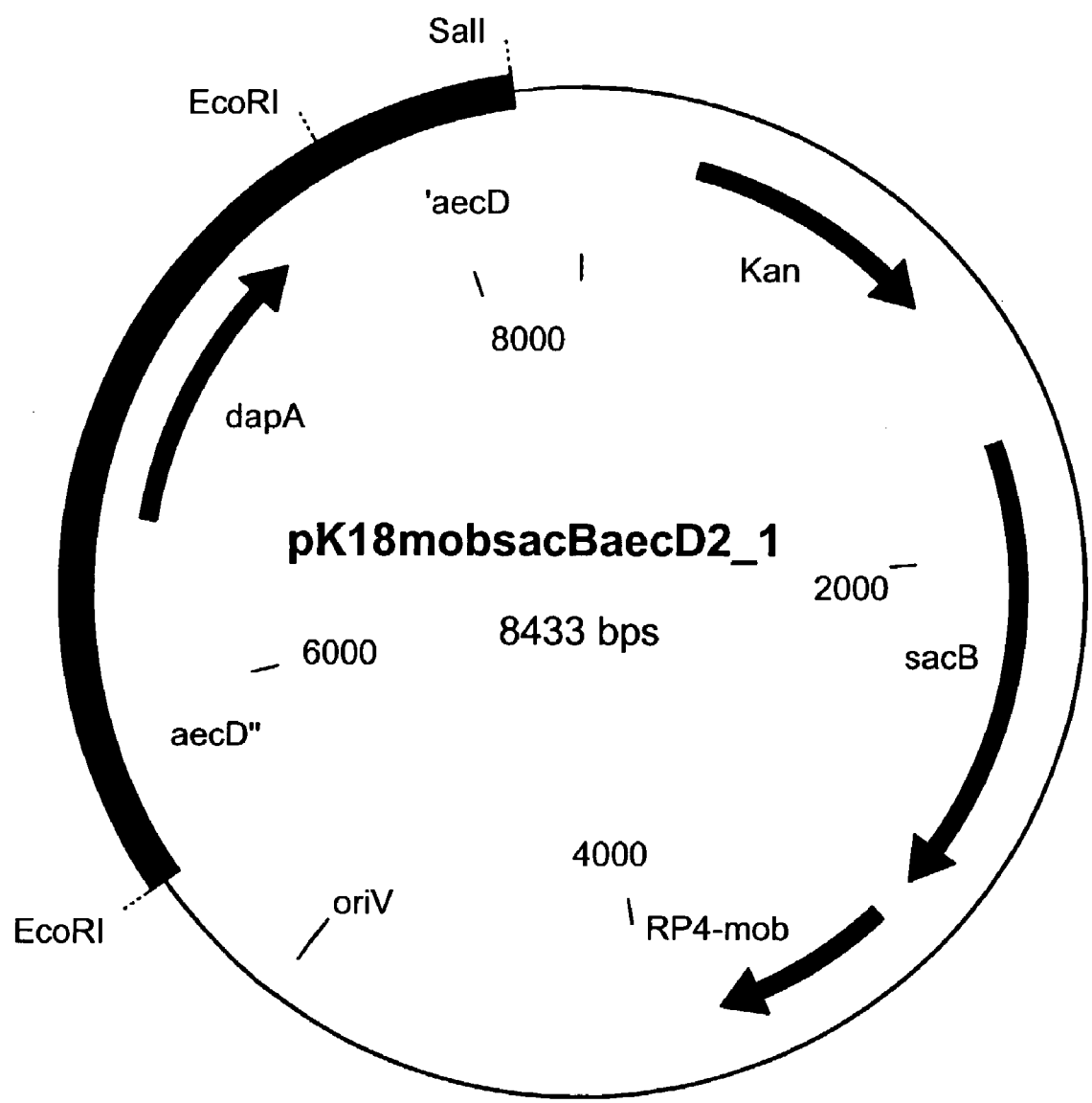

Figure 6: Plasmid pK18mobsacBpck1_3
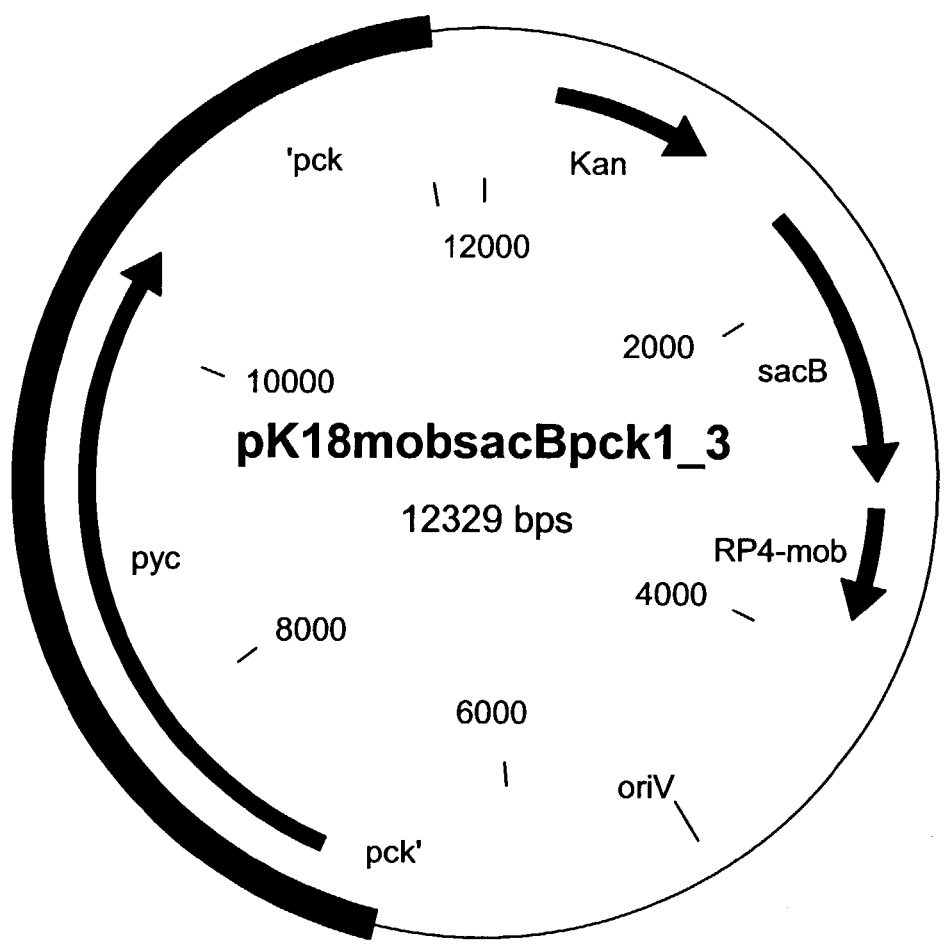

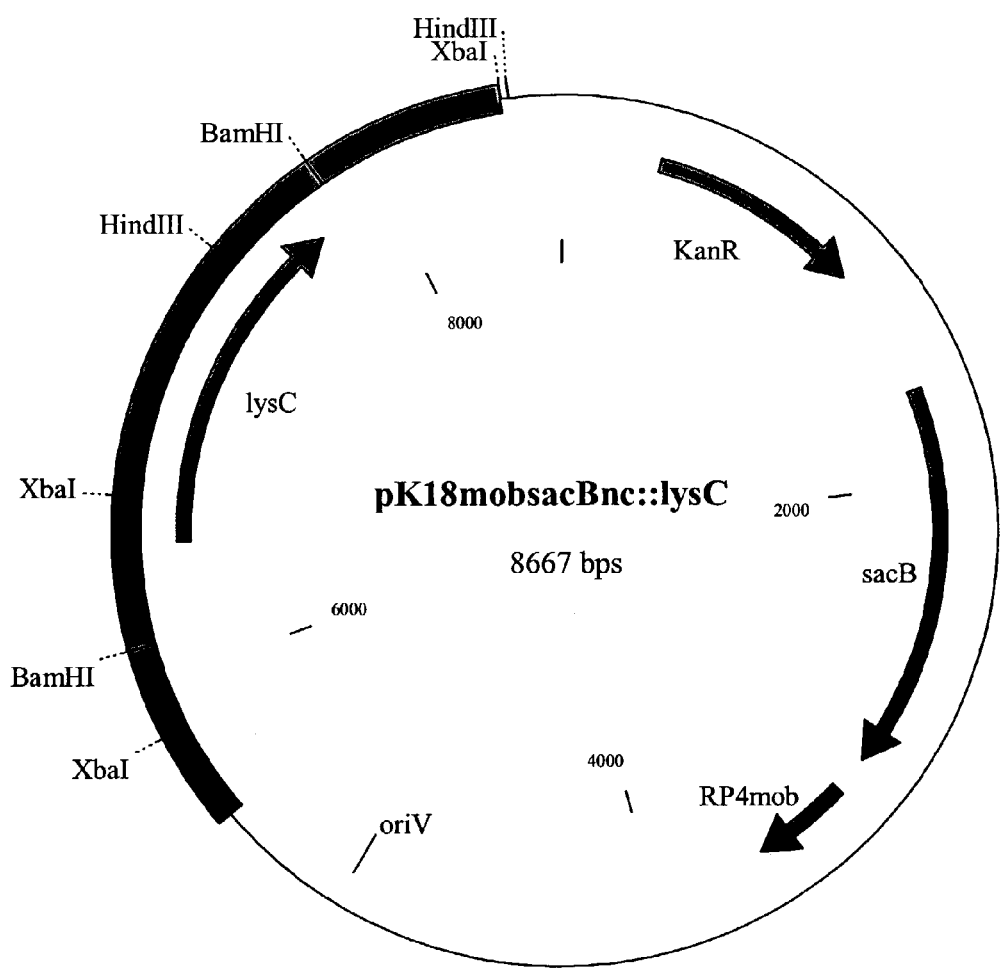
Figure 7: Plasmid pK18mobsacBnc::lysC

```
                        SEQUENCE LISTING

<160> NUMBER OF SEQ ID NOS: 30

<210> SEQ ID NO 1
<211> LENGTH: 1263
<212> TYPE: DNA
<213> ORGANISM: Corynebacterium glutamicum
<220> FEATURE:
<221> NAME/KEY: CDS
<222> LOCATION: (1)..(1263)
<223> OTHER INFORMATION: lysC wild-type gene

<400> SEQUENCE: 1 gtg gcc ctg gtc gta cag aaa tat ggc ggt tcc tcg ctt gag agt gcg       48
Met Ala Leu Val Val Gln Lys Tyr Gly Gly Ser Ser Leu Glu Ser Ala
1               5                   10                  15 gaa cgc att aga aac gtc gct gaa cgg atc gtt gcc acc aag aag gct       96
Glu Arg Ile Arg Asn Val Ala Glu Arg Ile Val Ala Thr Lys Lys Ala
            20                  25                  30 gga aat gat gtc gtg gtt gtc tgc tcc gca atg gga gac acc acg gat      144
Gly Asn Asp Val Val Val Val Cys Ser Ala Met Gly Asp Thr Thr Asp
        35                  40                  45 gaa ctt cta gaa ctt gca gcg gca gtg aat ccc gtt ccg cca gct cgt      192
Glu Leu Leu Glu Leu Ala Ala Ala Val Asn Pro Val Pro Pro Ala Arg
    50                  55                  60 gaa atg gat atg ctc ctg act gct ggt gag cgt att tct aac gct ctc      240
Glu Met Asp Met Leu Leu Thr Ala Gly Glu Arg Ile Ser Asn Ala Leu
65                  70                  75                  80 gtc gcc atg gct att gag tcc ctt ggc gca gaa gcc caa tct ttc acg      288
Val Ala Met Ala Ile Glu Ser Leu Gly Ala Glu Ala Gln Ser Phe Thr
                85                  90                  95 ggc tct cag gct ggt gtg ctc acc acc gag cgc cac gga aac gca cgc      336
Gly Ser Gln Ala Gly Val Leu Thr Thr Glu Arg His Gly Asn Ala Arg
            100                 105                 110 att gtt gat gtc act cca ggt cgt gtg cgt gaa gca ctc gat gag ggc      384
Ile Val Asp Val Thr Pro Gly Arg Val Arg Glu Ala Leu Asp Glu Gly
        115                 120                 125 aag atc tgc att gtt gct ggt ttc cag ggt gtt aat aaa gaa acc cgc      432
Lys Ile Cys Ile Val Ala Gly Phe Gln Gly Val Asn Lys Glu Thr Arg
    130                 135                 140 gat gtc acc acg ttg ggt cgt ggt ggt tct gac acc act gca gtt gcg      480
Asp Val Thr Thr Leu Gly Arg Gly Gly Ser Asp Thr Thr Ala Val Ala
145                 150                 155                 160 ttg gca gct gct ttg aac gct gat gtg tgt gag att tac tcg gac gtt      528
Leu Ala Ala Ala Leu Asn Ala Asp Val Cys Glu Ile Tyr Ser Asp Val
                165                 170                 175 gac ggt gtg tat acc gct gac ccg cgc atc gtt cct aat gca cag aag      576
Asp Gly Val Tyr Thr Ala Asp Pro Arg Ile Val Pro Asn Ala Gln Lys
            180                 185                 190
```

```
ctg gaa aag ctc agc ttc gaa gaa atg ctg gaa ctt gct gct gtt ggc      624
Leu Glu Lys Leu Ser Phe Glu Glu Met Leu Glu Leu Ala Ala Val Gly
        195                 200                 205 tcc aag att ttg gtg ctg cgc agt gtt gaa tac gct cgt gca ttc aat      672
Ser Lys Ile Leu Val Leu Arg Ser Val Glu Tyr Ala Arg Ala Phe Asn
    210                 215                 220 gtg cca ctt cgc gta cgc tcg tct tat agt aat gat ccc ggc act ttg      720
Val Pro Leu Arg Val Arg Ser Ser Tyr Ser Asn Asp Pro Gly Thr Leu
225                 230                 235                 240 att gcc ggc tct atg gag gat att cct gtg gaa gaa gca gtc ctt acc      768
Ile Ala Gly Ser Met Glu Asp Ile Pro Val Glu Glu Ala Val Leu Thr
                245                 250                 255 ggt gtc gca acc gac aag tcc gaa gcc aaa gta acc gtt ctg ggt att      816
Gly Val Ala Thr Asp Lys Ser Glu Ala Lys Val Thr Val Leu Gly Ile
            260                 265                 270 tcc gat aag cca ggc gag gct gcg aag gtt ttc cgt gcg ttg gct gat      864
Ser Asp Lys Pro Gly Glu Ala Ala Lys Val Phe Arg Ala Leu Ala Asp
        275                 280                 285 gca gaa atc aac att gac atg gtt ctg cag aac gtc tct tct gta gaa      912
Ala Glu Ile Asn Ile Asp Met Val Leu Gln Asn Val Ser Ser Val Glu
    290                 295                 300 gac ggc acc acc gac atc acc ttc acc tgc cct cgt tcc gac ggc cgc      960
Asp Gly Thr Thr Asp Ile Thr Phe Thr Cys Pro Arg Ser Asp Gly Arg
305                 310                 315                 320 cgc gcg atg gag atc ttg aag aag ctt cag gtt cag ggc aac tgg acc     1008
Arg Ala Met Glu Ile Leu Lys Lys Leu Gln Val Gln Gly Asn Trp Thr
                325                 330                 335 aat gtg ctt tac gac gac cag gtc ggc aaa gtc tcc ctc gtg ggt gct     1056
Asn Val Leu Tyr Asp Asp Gln Val Gly Lys Val Ser Leu Val Gly Ala
            340                 345                 350 ggc atg aag tct cac cca ggt gtt acc gca gag ttc atg gaa gct ctg     1104
Gly Met Lys Ser His Pro Gly Val Thr Ala Glu Phe Met Glu Ala Leu
        355                 360                 365 cgc gat gtc aac gtg aac atc gaa ttg att tcc acc tct gag att cgt     1152
Arg Asp Val Asn Val Asn Ile Glu Leu Ile Ser Thr Ser Glu Ile Arg
    370                 375                 380 att tcc gtg ctg atc cgt gaa gat gat ctg gat gct gct gca cgt gca     1200
Ile Ser Val Leu Ile Arg Glu Asp Asp Leu Asp Ala Ala Ala Arg Ala
385                 390                 395                 400 ttg cat gag cag ttc cag ctg ggc ggc gaa gac gaa gcc gtc gtt tat     1248
Leu His Glu Gln Phe Gln Leu Gly Gly Glu Asp Glu Ala Val Val Tyr
                405                 410                 415 gca ggc acc gga cgc                                                  1263
Ala Gly Thr Gly Arg
            420

<210> SEQ ID NO 2
<211> LENGTH: 421
<212> TYPE: PRT
<213> ORGANISM: Corynebacterium glutamicum

<400> SEQUENCE: 2

Met Ala Leu Val Val Gln Lys Tyr Gly Gly Ser Ser Leu Glu Ser Ala
1               5                   10                  15

Glu Arg Ile Arg Asn Val Ala Glu Arg Ile Val Ala Thr Lys Lys Ala
            20                  25                  30

Gly Asn Asp Val Val Val Val Cys Ser Ala Met Gly Asp Thr Thr Asp
        35                  40                  45

Glu Leu Leu Glu Leu Ala Ala Ala Val Asn Pro Val Pro Pro Ala Arg
```

```
                       50                  55                  60
Glu Met Asp Met Leu Leu Thr Ala Gly Glu Arg Ile Ser Asn Ala Leu
 65                  70                  75                  80

Val Ala Met Ala Ile Glu Ser Leu Gly Ala Glu Ala Gln Ser Phe Thr
                 85                  90                  95

Gly Ser Gln Ala Gly Val Leu Thr Thr Glu Arg His Gly Asn Ala Arg
            100                 105                 110

Ile Val Asp Val Thr Pro Gly Arg Val Arg Glu Ala Leu Asp Glu Gly
            115                 120                 125

Lys Ile Cys Ile Val Ala Gly Phe Gln Gly Val Asn Lys Glu Thr Arg
130                 135                 140

Asp Val Thr Thr Leu Gly Arg Gly Gly Ser Asp Thr Thr Ala Val Ala
145                 150                 155                 160

Leu Ala Ala Ala Leu Asn Ala Asp Val Cys Glu Ile Tyr Ser Asp Val
                165                 170                 175

Asp Gly Val Tyr Thr Ala Asp Pro Arg Ile Val Pro Asn Ala Gln Lys
            180                 185                 190

Leu Glu Lys Leu Ser Phe Glu Glu Met Leu Glu Leu Ala Ala Val Gly
            195                 200                 205

Ser Lys Ile Leu Val Leu Arg Ser Val Glu Tyr Ala Arg Ala Phe Asn
210                 215                 220

Val Pro Leu Arg Val Arg Ser Ser Tyr Ser Asn Asp Pro Gly Thr Leu
225                 230                 235                 240

Ile Ala Gly Ser Met Glu Asp Ile Pro Val Glu Glu Ala Val Leu Thr
                245                 250                 255

Gly Val Ala Thr Asp Lys Ser Glu Ala Lys Val Thr Val Leu Gly Ile
            260                 265                 270

Ser Asp Lys Pro Gly Glu Ala Ala Lys Val Phe Arg Ala Leu Ala Asp
            275                 280                 285

Ala Glu Ile Asn Ile Asp Met Val Leu Gln Asn Val Ser Ser Val Glu
290                 295                 300

Asp Gly Thr Thr Asp Ile Thr Phe Thr Cys Pro Arg Ser Asp Gly Arg
305                 310                 315                 320

Arg Ala Met Glu Ile Leu Lys Lys Leu Gln Val Gln Gly Asn Trp Thr
                325                 330                 335

Asn Val Leu Tyr Asp Asp Gln Val Gly Lys Val Ser Leu Val Gly Ala
            340                 345                 350

Gly Met Lys Ser His Pro Gly Val Thr Ala Glu Phe Met Glu Ala Leu
            355                 360                 365

Arg Asp Val Asn Val Asn Ile Glu Leu Ile Ser Thr Ser Glu Ile Arg
370                 375                 380

Ile Ser Val Leu Ile Arg Glu Asp Asp Leu Asp Ala Ala Ala Arg Ala
385                 390                 395                 400

Leu His Glu Gln Phe Gln Leu Gly Gly Glu Asp Glu Ala Val Val Tyr
                405                 410                 415

Ala Gly Thr Gly Arg
            420

<210> SEQ ID NO 3
<211> LENGTH: 1263
<212> TYPE: DNA
<213> ORGANISM: Corynebacterium glutamicum
<220> FEATURE:
<221> NAME/KEY: CDS
<222> LOCATION: (1)..(1263)
```

-continued

<223> OTHER INFORMATION: lysC-fbr allele lysC T311I

<400> SEQUENCE: 3

```
gtg gcc ctg gtc gta cag aaa tat ggc ggt tcc tcg ctt gag agt gcg      48
Met Ala Leu Val Val Gln Lys Tyr Gly Gly Ser Ser Leu Glu Ser Ala
1               5                  10                  15 gaa cgc att aga aac gtc gct gaa cgg atc gtt gcc acc aag aag gct      96
Glu Arg Ile Arg Asn Val Ala Glu Arg Ile Val Ala Thr Lys Lys Ala
            20                  25                  30 gga aat gat gtc gtg gtt gtc tgc tcc gca atg gga gac acc acg gat     144
Gly Asn Asp Val Val Val Val Cys Ser Ala Met Gly Asp Thr Thr Asp
        35                  40                  45 gaa ctt cta gaa ctt gca gcg gca gtg aat ccc gtt ccg cca gct cgt     192
Glu Leu Leu Glu Leu Ala Ala Ala Val Asn Pro Val Pro Pro Ala Arg
50                  55                  60 gaa atg gat atg ctc ctg act gct ggt gag cgt att tct aac gct ctc     240
Glu Met Asp Met Leu Leu Thr Ala Gly Glu Arg Ile Ser Asn Ala Leu
65                  70                  75                  80 gtc gcc atg gct att gag tcc ctt ggc gca gaa gcc caa tct ttc acg     288
Val Ala Met Ala Ile Glu Ser Leu Gly Ala Glu Ala Gln Ser Phe Thr
                85                  90                  95 ggc tct cag gct ggt gtg ctc acc acc gag cgc cac gga aac gca cgc     336
Gly Ser Gln Ala Gly Val Leu Thr Thr Glu Arg His Gly Asn Ala Arg
            100                 105                 110 att gtt gat gtc act cca ggt cgt gtg cgt gaa gca ctc gat gag ggc     384
Ile Val Asp Val Thr Pro Gly Arg Val Arg Glu Ala Leu Asp Glu Gly
        115                 120                 125 aag atc tgc att gtt gct ggt ttc cag ggt gtt aat aaa gaa acc cgc     432
Lys Ile Cys Ile Val Ala Gly Phe Gln Gly Val Asn Lys Glu Thr Arg
    130                 135                 140 gat gtc acc acg ttg ggt cgt ggt ggt tct gac acc act gca gtt gcg     480
Asp Val Thr Thr Leu Gly Arg Gly Gly Ser Asp Thr Thr Ala Val Ala
145                 150                 155                 160 ttg gca gct gct ttg aac gct gat gtg tgt gag att tac tcg gac gtt     528
Leu Ala Ala Ala Leu Asn Ala Asp Val Cys Glu Ile Tyr Ser Asp Val
                165                 170                 175 gac ggt gtg tat acc gct gac ccg cgc atc gtt cct aat gca cag aag     576
Asp Gly Val Tyr Thr Ala Asp Pro Arg Ile Val Pro Asn Ala Gln Lys
            180                 185                 190 ctg gaa aag ctc agc ttc gaa gaa atg ctg gaa ctt gct gct gtt ggc     624
Leu Glu Lys Leu Ser Phe Glu Glu Met Leu Glu Leu Ala Ala Val Gly
        195                 200                 205 tcc aag att ttg gtg ctg cgc agt gtt gaa tac gct cgt gca ttc aat     672
Ser Lys Ile Leu Val Leu Arg Ser Val Glu Tyr Ala Arg Ala Phe Asn
    210                 215                 220 gtg cca ctt cgc gta cgc tcg tct tat agt aat gat ccc ggc act ttg     720
Val Pro Leu Arg Val Arg Ser Ser Tyr Ser Asn Asp Pro Gly Thr Leu
225                 230                 235                 240 att gcc ggc tct atg gag gat att cct gtg gaa gaa gca gtc ctt acc     768
Ile Ala Gly Ser Met Glu Asp Ile Pro Val Glu Glu Ala Val Leu Thr
                245                 250                 255 ggt gtc gca acc gac aag tcc gaa gcc aaa gta acc gtt ctg ggt att     816
Gly Val Ala Thr Asp Lys Ser Glu Ala Lys Val Thr Val Leu Gly Ile
            260                 265                 270 tcc gat aag cca ggc gag gct gcg aag gtt ttc cgt gcg ttg gct gat     864
Ser Asp Lys Pro Gly Glu Ala Ala Lys Val Phe Arg Ala Leu Ala Asp
        275                 280                 285 gca gaa atc aac att gac atg gtt ctg cag aac gtc tct tct gta gaa     912
Ala Glu Ile Asn Ile Asp Met Val Leu Gln Asn Val Ser Ser Val Glu
    290                 295                 300
```

```
gac ggc acc acc gac atc atc ttc acc tgc cct cgt tcc gac ggc cgc      960
Asp Gly Thr Thr Asp Ile Ile Phe Thr Cys Pro Arg Ser Asp Gly Arg
305                 310                 315                 320 cgc gcg atg gag atc ttg aag aag ctt cag gtt cag ggc aac tgg acc     1008
Arg Ala Met Glu Ile Leu Lys Lys Leu Gln Val Gln Gly Asn Trp Thr
                325                 330                 335 aat gtg ctt tac gac gac cag gtc ggc aaa gtc tcc ctc gtg ggt gct     1056
Asn Val Leu Tyr Asp Asp Gln Val Gly Lys Val Ser Leu Val Gly Ala
            340                 345                 350 ggc atg aag tct cac cca ggt gtt acc gca gag ttc atg gaa gct ctg     1104
Gly Met Lys Ser His Pro Gly Val Thr Ala Glu Phe Met Glu Ala Leu
        355                 360                 365 cgc gat gtc aac gtg aac atc gaa ttg att tcc acc tct gag att cgt     1152
Arg Asp Val Asn Val Asn Ile Glu Leu Ile Ser Thr Ser Glu Ile Arg
    370                 375                 380 att tcc gtg ctg atc cgt gaa gat gat ctg gat gct gct gca cgt gca     1200
Ile Ser Val Leu Ile Arg Glu Asp Asp Leu Asp Ala Ala Ala Arg Ala
385                 390                 395                 400 ttg cat gag cag ttc cag ctg ggc ggc gaa gac gaa gcc gtc gtt tat     1248
Leu His Glu Gln Phe Gln Leu Gly Gly Glu Asp Glu Ala Val Val Tyr
                405                 410                 415 gca ggc acc gga cgc                                                  1263
Ala Gly Thr Gly Arg
            420
```

<210> SEQ ID NO 4
<211> LENGTH: 421
<212> TYPE: PRT
<213> ORGANISM: Corynebacterium glutamicum

<400> SEQUENCE: 4

```
Met Ala Leu Val Val Gln Lys Tyr Gly Gly Ser Ser Leu Glu Ser Ala
1               5                   10                  15

Glu Arg Ile Arg Asn Val Ala Glu Arg Ile Val Ala Thr Lys Lys Ala
            20                  25                  30

Gly Asn Asp Val Val Val Val Cys Ser Ala Met Gly Asp Thr Thr Asp
        35                  40                  45

Glu Leu Leu Glu Leu Ala Ala Ala Val Asn Pro Val Pro Pro Ala Arg
    50                  55                  60

Glu Met Asp Met Leu Leu Thr Ala Gly Glu Arg Ile Ser Asn Ala Leu
65                  70                  75                  80

Val Ala Met Ala Ile Glu Ser Leu Gly Ala Glu Ala Gln Ser Phe Thr
                85                  90                  95

Gly Ser Gln Ala Gly Val Leu Thr Thr Glu Arg His Gly Asn Ala Arg
            100                 105                 110

Ile Val Asp Val Thr Pro Gly Arg Val Arg Glu Ala Leu Asp Glu Gly
        115                 120                 125

Lys Ile Cys Ile Val Ala Gly Phe Gln Gly Val Asn Lys Glu Thr Arg
    130                 135                 140

Asp Val Thr Thr Leu Gly Arg Gly Gly Ser Asp Thr Thr Ala Val Ala
145                 150                 155                 160

Leu Ala Ala Ala Leu Asn Ala Asp Val Cys Glu Ile Tyr Ser Asp Val
                165                 170                 175

Asp Gly Val Tyr Thr Ala Asp Pro Arg Ile Val Pro Asn Ala Gln Lys
            180                 185                 190

Leu Glu Lys Leu Ser Phe Glu Glu Met Leu Glu Leu Ala Ala Val Gly
        195                 200                 205
```

-continued

```
Ser Lys Ile Leu Val Leu Arg Ser Val Glu Tyr Ala Arg Ala Phe Asn
    210                 215                 220
Val Pro Leu Arg Val Arg Ser Ser Tyr Ser Asn Asp Pro Gly Thr Leu
225                 230                 235                 240
Ile Ala Gly Ser Met Glu Asp Ile Pro Val Glu Ala Val Leu Thr
                245                 250                 255
Gly Val Ala Thr Asp Lys Ser Glu Ala Lys Val Thr Val Leu Gly Ile
                260                 265                 270
Ser Asp Lys Pro Gly Glu Ala Ala Lys Val Phe Arg Ala Leu Ala Asp
            275                 280                 285
Ala Glu Ile Asn Ile Asp Met Val Leu Gln Asn Val Ser Ser Val Glu
        290                 295                 300
Asp Gly Thr Thr Asp Ile Ile Phe Thr Cys Pro Arg Ser Asp Gly Arg
305                 310                 315                 320
Arg Ala Met Glu Ile Leu Lys Lys Leu Gln Val Gln Gly Asn Trp Thr
                325                 330                 335
Asn Val Leu Tyr Asp Asp Gln Val Gly Lys Val Ser Leu Val Gly Ala
                340                 345                 350
Gly Met Lys Ser His Pro Gly Val Thr Ala Glu Phe Met Glu Ala Leu
            355                 360                 365
Arg Asp Val Asn Val Asn Ile Glu Leu Ile Ser Thr Ser Glu Ile Arg
        370                 375                 380
Ile Ser Val Leu Ile Arg Glu Asp Asp Leu Asp Ala Ala Ala Arg Ala
385                 390                 395                 400
Leu His Glu Gln Phe Gln Leu Gly Gly Glu Asp Glu Ala Val Val Tyr
                405                 410                 415
Ala Gly Thr Gly Arg
            420

<210> SEQ ID NO 5
<211> LENGTH: 28
<212> TYPE: DNA
<213> ORGANISM: Artificial sequence
<220> FEATURE:
<221> NAME/KEY: misc_feature
<222> LOCATION: (1)..(28)
<223> OTHER INFORMATION: Primer lysC1beg

<400> SEQUENCE: 5
taggatcctc cggtgtctga ccacggtg                                      28

<210> SEQ ID NO 6
<211> LENGTH: 29
<212> TYPE: DNA
<213> ORGANISM: Artificial sequence
<220> FEATURE:
<221> NAME/KEY: misc_feature
<222> LOCATION: (1)..(29)
<223> OTHER INFORMATION: Primer lysC2end

<400> SEQUENCE: 6
acggatccgc tgggaaattg cgctcttcc                                     29

<210> SEQ ID NO 7
<211> LENGTH: 28
<212> TYPE: DNA
<213> ORGANISM: Artificial sequence
<220> FEATURE:
<221> NAME/KEY: misc_feature
<222> LOCATION: (1)..(28)
```

```
<223> OTHER INFORMATION: Primer gluBgl1

<400> SEQUENCE: 7
taagatctgt gttggacgtc atggcaag                                    28

<210> SEQ ID NO 8
<211> LENGTH: 28
<212> TYPE: DNA
<213> ORGANISM: Artificial sequence
<220> FEATURE:
<221> NAME/KEY: misc_feature
<222> LOCATION: (1)..(28)
<223> OTHER INFORMATION: Primer gluBgl2

<400> SEQUENCE: 8
acagatcttg aagccaagta cggccaag                                    28

<210> SEQ ID NO 9
<211> LENGTH: 27
<212> TYPE: DNA
<213> ORGANISM: Artificial sequence
<220> FEATURE:
<221> NAME/KEY: misc_feature
<222> LOCATION: (1)..(27)
<223> OTHER INFORMATION: Primer pck_beg

<400> SEQUENCE: 9
taagatctgc cggcatgact tcagttt                                     27

<210> SEQ ID NO 10
<211> LENGTH: 30
<212> TYPE: DNA
<213> ORGANISM: Artificial sequence
<220> FEATURE:
<221> NAME/KEY: misc_feature
<222> LOCATION: (1)..(30)
<223> OTHER INFORMATION: Primer pck_end

<400> SEQUENCE: 10
acagatctgg tgggagcctt tcttgttatt                                  30

<210> SEQ ID NO 11
<211> LENGTH: 20
<212> TYPE: DNA
<213> ORGANISM: Corynebacterium glutamicum
<220> FEATURE:
<221> NAME/KEY: misc_feature
<222> LOCATION: (1)..(20)
<223> OTHER INFORMATION: Primer aecD_beg

<400> SEQUENCE: 11
gaacttacgc caagctgttc                                             20

<210> SEQ ID NO 12
<211> LENGTH: 20
<212> TYPE: DNA
<213> ORGANISM: Corynebacterium glutamicum
<220> FEATURE:
<221> NAME/KEY: misc_feature
<222> LOCATION: (1)..(20)
<223> OTHER INFORMATION: Primer aecD_end

<400> SEQUENCE: 12
agcaccacaa tcaacgtgag                                             20

<210> SEQ ID NO 13
<211> LENGTH: 20
```

```
<212> TYPE: DNA
<213> ORGANISM: Corynebacterium glutamicum
<220> FEATURE:
<221> NAME/KEY: misc_feature
<222> LOCATION: (1)..(20)
<223> OTHER INFORMATION: Primer gluA_beg

<400> SEQUENCE: 13
cacggttgct cattgtatcc                                              20

<210> SEQ ID NO 14
<211> LENGTH: 20
<212> TYPE: DNA
<213> ORGANISM: Corynebacterium glutamicum
<220> FEATURE:
<221> NAME/KEY: misc_feature
<222> LOCATION: (1)..(20)
<223> OTHER INFORMATION: Primer gluD_end

<400> SEQUENCE: 14
cgaggcgaat cagacttctt                                              20

<210> SEQ ID NO 15
<211> LENGTH: 20
<212> TYPE: DNA
<213> ORGANISM: Corynebacterium glutamicum
<220> FEATURE:
<221> NAME/KEY: misc_feature
<222> LOCATION: (1)..(20)
<223> OTHER INFORMATION: Primer ddh_beg

<400> SEQUENCE: 15
ctgaatcaaa ggcggacatg                                              20

<210> SEQ ID NO 16
<211> LENGTH: 20
<212> TYPE: DNA
<213> ORGANISM: Corynebacterium glutamicum
<220> FEATURE:
<221> NAME/KEY: misc_feature
<222> LOCATION: (1)..(20)
<223> OTHER INFORMATION: Primer ddh_end

<400> SEQUENCE: 16
tcgagctaaa ttagacgtcg                                              20

<210> SEQ ID NO 17
<211> LENGTH: 20
<212> TYPE: DNA
<213> ORGANISM: Corynebacterium glutamicum
<220> FEATURE:
<221> NAME/KEY: misc_feature
<222> LOCATION: (1)..(20)
<223> OTHER INFORMATION: Primer dapA_beg

<400> SEQUENCE: 17
cgagccagtg aacatgcaga                                              20

<210> SEQ ID NO 18
<211> LENGTH: 20
<212> TYPE: DNA
<213> ORGANISM: Corynebacterium glutamicum
<220> FEATURE:
<221> NAME/KEY: misc_feature
<222> LOCATION: (1)..(20)
<223> OTHER INFORMATION: Primer dapA_end

<400> SEQUENCE: 18
```
cttgagcacc ttgcgcagca                                         20

<210> SEQ ID NO 19
<211> LENGTH: 28
<212> TYPE: DNA
<213> ORGANISM: Artificial sequence
<220> FEATURE:
<221> NAME/KEY: misc_feature
<222> LOCATION: (1)..(28)
<223> OTHER INFORMATION: Primer pyc_beg

<400> SEQUENCE: 19
tcacgcgtct tgaagtcgtg caggtcag                                28

<210> SEQ ID NO 20
<211> LENGTH: 28
<212> TYPE: DNA
<213> ORGANISM: Artificial sequence
<220> FEATURE:
<221> NAME/KEY: misc_feature
<222> LOCATION: (1)..(28)
<223> OTHER INFORMATION: Primer pyc_end

<400> SEQUENCE: 20
tcacgcgtcg cctcctccat gaggaaga                                28

<210> SEQ ID NO 21
<211> LENGTH: 39
<212> TYPE: DNA
<213> ORGANISM: Corynebacterium glutamicum
<220> FEATURE:
<221> NAME/KEY: misc_feature
<222> LOCATION: (1)..(39)
<223> OTHER INFORMATION: Primer P458S-1

<400> SEQUENCE: 21
ggattcattg ccgatcactc gcacctcctt caggctcca                    39

<210> SEQ ID NO 22
<211> LENGTH: 39
<212> TYPE: DNA
<213> ORGANISM: Corynebacterium glutamicum
<220> FEATURE:
<221> NAME/KEY: misc_feature
<222> LOCATION: (1)..(39)
<223> OTHER INFORMATION: Primer P458S-2

<400> SEQUENCE: 22
gtggaggaag tccgaggtcg agtgatcggc aatgaatcc                    39

<210> SEQ ID NO 23
<211> LENGTH: 1310
<212> TYPE: DNA
<213> ORGANISM: Corynebacterium glutamicum
<220> FEATURE:
<221> NAME/KEY: misc_feature
<222> LOCATION: (1)..(1310)
<223> OTHER INFORMATION: Intergenic region ncode1

<400> SEQUENCE: 23
aagctctatt gtcccctacg tgctcgtttc tggcctttta gtaagcacca ggaataagcg    60
ccgatgaaga cacaatcata ccgacaatta atcgtgccga tatgagctct taaaagacag   120
cataaaacga gttttttcaaa agcctattaa gtgtcaatta cgacgtgcat taatagatac   180
tcaatcacct taaattgttg acacactcca ctaaaacagg tctattaaaa gacaattgaa   240
ttacgcccta gtagtacttg tttcaggcca ccacttagaa ggcttttaag tatccactat   300

```
gtatcaatta tctagaacct ttagtgactt tgaaacggca gtactctatt ggctcttaat      360
ggtcaattac ataacaatta tattgagcct ttgaaacaac tcactctgct gcatattaaa      420
aggtcgatta actaacgatt gaattgatcc ttaaaaagcc tttatctatc gcattatgaa      480
taaatattta atcgaccttt aatagtgacc taaaagcctt ttaaaagcca acgcattcag      540 tgactttaa aaggctatta agtgtcaatt gaattgcctt gttactggct tttaaaggc       600 tattaaagaa cactcccta ttgtctttta atcgtcactt aatcgacctc taaaaggtaa      660
ctaattgact cttgagtgac acatatttaa ttgaccttta agtaacgatt ataaggcaat      720
taatgtgacc aaataaagac acgtaactga ctaatcttta tctgactatt acaaggcttt      780
aaaagagcac ttatgtgtcg attaagtgtc tacgcaataa ctgtgcttta agaggcttta     840
aaaactacaa ttgaatcgac cactaatcgt tacttaaatg actattaaca aaagtcactt     900
ttagagcacc gcaaaagcct tttaatggtc acgcaataag cctttaagta acaattaaat    960
aagtggcttt aaaatcacta ctgcagcacg attgaaaggt aattagcggt cgattaagtg    1020
tcaattaatt aatagtgatt caaaatctca ttaaagcgca attcaattga cagctaataa   1080
gcccttaagt aacaaatact ttatccgtac tttaagggca cgctaaaagc ctttttaatcg  1140 acatctaatt gtcataacgc ttcgatgcgc ccatgggaat acacttagcg gtcgattaaa   1200
tggatactaa gtagcaatta gccagagtcg cgtgacagag ttgtggcgca cagtagcaca   1260 tcaccctac ccccgtgcat ctcttaatta gcactaaaac aacatttatc                1310
```

<210> SEQ ID NO 24
<211> LENGTH: 28
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(28)
<223> OTHER INFORMATION: Primer ncode 1

<400> SEQUENCE: 24
gaagatctaa gctctattgt cccctacg                                        28

<210> SEQ ID NO 25
<211> LENGTH: 25
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(25)
<223> OTHER INFORMATION: Primer ncode 2

<400> SEQUENCE: 25 gatccttta aaagccagta acaag                                            25

<210> SEQ ID NO 26
<211> LENGTH: 47
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(47)
<223> OTHER INFORMATION: Primer ncode 3

```
<400> SEQUENCE: 26
cttgttactg gcttttaaaa ggatcctatt aaagaacact cccctat          47

<210> SEQ ID NO 27
<211> LENGTH: 28
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(28)
<223> OTHER INFORMATION: Primer ncode 4

<400> SEQUENCE: 27
gaagatctcg actctggcta attgctac                               28

<210> SEQ ID NO 28
<211> LENGTH: 1249
<212> TYPE: DNA
<213> ORGANISM: Artificial Sequence
<220> FEATURE:
<223> OTHER INFORMATION: PCR-Produkt
<220> FEATURE:
<221> NAME/KEY: misc_feature
<222> LOCATION: (1)..(1249)
<223> OTHER INFORMATION: Intergenic region ncode1 after PCR

<400> SEQUENCE: 28
gaagatctaa gctctattgt cccctacgtg ctcgtttctg gccttttagt aagcaccagg      60
aataagcgcc gatgaagaca caatcatacc gacaattaat cgtgccgata tgagctctta     120
aaagacagca taaacgagt ttttcaaaag cctattaagt gtcaattacg acgtgcatta      180
atagatactc aatcaccta aattgttgac acactccact aaaacaggtc tattaaaaga     240
caattgaatt acgccctagt agtacttgtt tcaggccacc acttagaagg cttttaagta     300
tccactatgt atcaattatc tagaaccttt agtgactttg aaacggcagt actctattgg     360
ctcttaatgg tcaattacat aacaattata ttgagccttt gaaacaactc actctgctgc     420
atattaaaag gtcgattaac taacgattga attgatcctt aaaaagcctt tatctatcgc     480
attatgaata aatatttaat cgacctttaa tagtgaccta aaagcctttt aaaagccaac     540
gcattcagtg acttttaaaa ggctattaag tgtcaattga attgccttgt tactggcttt     600 taaaggatc ctattaaaga acactccct attgtctttt aatcgtcact taatcgacct      660 ctaaaggta actaattgac tcttgagtga cacatattta attgacctttt aagtaacgat     720 tataaggcaa ttaatgtgac caaataaaga cacgtaactg actaatcttt atctgactat     780
tacaaggctt taaagagca cttatgtgtc gattaagtgt ctacgcaata actgtgcttt      840
aagaggcttt aaaaactaca attgaatcga ccactaatcg ttacttaaat gactattaac     900
aaaagtcact tttagagcac cgcaaaagcc ttttaatggt cacgcaataa gcctttaagt     960
aacaattaaa taagtggctt taaaatcact actgcagcac gattgaaagg taattagcgg    1020
tcgattaagt gtcaattaat taatagtgat tcaaaatctc attaaagcgc aattcaattg    1080
acagctaata agcccttaag taacaaatac tttatccgta ctttaagggc acgctaaaag    1140
ccttttaatc gacatctaat tgtcataacg cttcgatgcg cccatgggaa tacacttagc    1200
ggtcgattaa atggatacta agtagcaatt agccagagtc gagatctag               1249

<210> SEQ ID NO 29
<211> LENGTH: 20
```

```
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(20)
<223> OTHER INFORMATION: Primer 3371V

<400> SEQUENCE: 29
tatcatgcgg tgagctgtga                                          20

<210> SEQ ID NO 30
<211> LENGTH: 20
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(20)
<223> OTHER INFORMATION: Primer 3372N

<400> SEQUENCE: 30
taggggtgat gtgctactgt                                          20
```

CORYNEFORM BACTERIA WHICH PRODUCE CHEMICAL COMPOUNDS I

This is a continuation-in-part application of International Patent Appl. No. PCT/EP02/08464 filed on Jul. 30, 2002 which claims priority to U.S. Prov. Appl. No. 60/309,878, filed Aug. 6, 2001.

BACKGROUND

Chemical compounds, which means, in particular, L-amino acids, vitamins, nucleosides and nucleotides and D-amino acids, are used in human medicine, in the pharmaceuticals industry, in cosmetics, in the foodstuffs industry and in animal nutrition.

Numerous of these compounds are prepared by fermentation from strains of coryneform bacteria, in particular *Corynebacterium glutamicum*. Because of their great importance, work is constantly being undertaken to improve the preparation processes. Improvements to the process can relate to fermentation measures, such as, for example, stirring and supply of oxygen, or the composition of the nutrient media, such as, for example, the sugar concentration during the fermentation, or the working up to the product form by, for example, ion exchange chromatography, or the intrinsic output properties of the microorganism itself.

Methods of mutagenesis, selection and mutant selection are used to improve the output properties of these microorganisms. Strains which are resistant to antimetabolites or are auxotrophic for metabolites of regulatory importance and which produce the particular compounds are obtained in this manner.

Methods of the recombinant DNA technique have also been employed for some years for improving the strain of *Corynebacterium* strains, by amplifying individual biosynthesis genes and investigating the effect on production.

A common method comprises amplification of certain biosynthesis genes in the particular microorganism by means of episomally replicating plasmids. This procedure has the disadvantage that during the fermentation, which in industrial processes is in general associated with numerous generations, the plasmids are lost spontaneously (segregational instability).

Another method comprises duplicating certain biosynthesis genes by means of plasmids which do not replicate in the particular microorganism. In this method, the plasmid, including the cloned biosynthesis gene, is integrated into the chromosomal biosynthesis gene of the microorganism (Reinscheid et al., Applied and Environmental Microbiology 60(1), 126–132 (1994); Jetten et al., Applied Microbiology and Biotechnology 43(1):76–82 (1995)). A disadvantage of this method is that the nucleotide sequences of the plasmid and of the antibiotic resistance gene necessary for the selection remain in the microorganism. This is a disadvantage, for example, for the disposal and utilization of the biomass. Moreover, the expert expects such strains to be unstable as a result of disintegration by "Campbell type cross over" in a corresponding number of generations such as are usual in industrial fermentations.

OBJECT OF THE INVENTION

The inventors had the object of providing new measures for improved fermentative preparation chemical compounds using coryneform bacteria.

SUMMARY OF THE INVENTION

Coryneform bacteria which produce chemical compounds, characterised in that these have, in addition to at least one copy, present at the natural site (locus), of an open reading frame (ORF), gene or allele which codes for the synthesis of a protein or an RNA, a second, optionally third or fourth copy of the open reading frame (ORF), gene or allele in question at a second, optionally third or fourth site in a form integrated into the chromosome, no nucleotide sequence which is capable of/enables episomal replication or transposition in microorganisms and no nucleotide sequence(s) which impart(s) resistance to antibiotics being present at the second, optionally third or fourth site, and the second, optionally third or fourth site not relating to open reading frames (ORF), genes or alleles which are essential for the growth of the bacteria and the production of the desired compound.

The invention also provides processes for the preparation of one or more chemical compounds, in which the following steps are carried out:
a) fermentation of coryneform bacteria,
a1) which have, in addition to at least one copy, present at the natural site (locus), of an open reading frame (ORF), gene or allele which codes for the synthesis of a protein or an RNA, a second, optionally third or fourth copy of this open reading frame (ORF), gene or allele at a second, optionally third or fourth site in a form integrated into the chromosome, no nucleotide sequence which is capable of/enables episomal replication or transposition in microorganisms and no nucleotide sequence(s) which impart(s) resistance to antibiotics being present at the second, optionally third or fourth site, and the second, optionally third or fourth site not relating to open reading frames (ORF), genes or alleles which are essential for the growth of the bacteria and the production of the desired compound, and
a2) in which the intracellular activity of the corresponding protein is increased, in particular the nucleotide sequence which codes for this protein is over-expressed,
b) concentration of the chemical compound(s) in the fermentation broth and/or in the cells of the bacteria,
c) isolation of the chemical compound(s), optionally
d) with constituents from the fermentation broth and/or the biomass to the extent of > (greater than) 0 to 100 wt. %.

The invention also provides processes for the preparation of one or more chemical compounds, which comprise the following steps:
a) fermentation of coryneform bacteria, in particular of the genus *Corynebacterium*, which have, in addition to the copy of an open reading frame (ORF), gene or allele present at the natural site (locus), in each case a second, optionally third or fourth copy of the open reading frame (ORF), gene or allele in question at in each case a second, optionally third or fourth site in integrated form, no nucleotide sequence which is capable of/enables episomal replication in microorganisms, no nucleotide sequence which is capable of/enables transposition and no nucleotide sequence which imparts resistance to antibiotics being present at the particular second, optionally third or fourth site,
under conditions which allow expression of the said open reading frames (ORF), genes or alleles
b) concentration of the chemical compound(s) in the fermentation broth and/or in the cells of the bacteria, c) isolation of the chemical compound(s), optionally
d) with constituents from the fermentation broth and/or the biomass to the extent of > (greater than) 0 to 100%.

DETAILED DESCRIPTION OF THE INVENTION

Chemical compounds are to be understood, in particular, as meaning amino acids, vitamins, nucleosides and nucleotides. The biosynthesis pathways of these compounds are known and are available in the prior art.

Amino acids mean, preferably, L-amino acids, in particular the proteinogenic L-amino acids, chosen from the group consisting of L-aspartic acid, L-asparagine, L-threonine, L-serine, L-glutamic acid, L-glutamine, glycine, L-alanine, L-cysteine, L-valine, L-methionine, L-isoleucine, L-leucine, L-tyrosine, L-phenylalanine, L-histidine, L-lysine, L-tryptophan, L-proline and L-arginine and salts thereof, in particular L-lysine, L-methionine and L-threonine. L-Lysine is very particularly preferred.

Proteinogenic amino acids are understood as meaning the amino acids which occur in natural proteins, that is to say in proteins of microorganisms, plants, animals and humans.

Vitamins mean, in particular, vitamin B1 (thiamine), vitamin B2 (riboflavin), vitamin B5 (pantothenic acid), vitamin B6 (pyridoxines), vitamin B12 (cyanocobalamin), nicotinic acid/nicotinamide, vitamin M (folic acid) and vitamin E (tocopherol) and salts thereof, pantothenic acid being preferred.

Nucleosides and nucleotides mean, inter alia, S-adenosylmethionine, inosine-5'-monophosphoric acid and guanosine-5'-monophosphoric acid and salts thereof.

The coryneform bacteria are, in particular, those of the genus *Corynebacterium*. Of the genus *Corynebacterium*, the species *Corynebacterium glutamicum*, *Corynebacterium ammoniagenes* and *Corynebacterium thermoaminogenes* are preferred. Information on the taxonomic classification of strains of this group of bacteria is to be found, inter alia, in Kämpfer and Kroppenstedt (Canadian Journal of Microbiology 42, 989–1005 (1996)) and in U.S. Pat. No. 5,250,434.

Suitable strains of the species *Corynebacterium glutamicum* (*C. glutamicum*) are, in particular, the known wild-type strains Corynebacterium glutamicum ATCC13032
Corynebacterium acetoglutamicum ATCC15806
Corynebacterium acetoacidophilum ATCC13870
Corynebacterium lilium ATCC15990
Corynebacterium melassecola ATCC17965
Corynebacterium herculis ATCC13868
Arthrobacter sp. ATCC243
Brevibacterium chang-fua ATCC14017
Brevibacterium flavum ATCC14067
Brevibacterium lactofermentum ATCC13869
Brevibacterium divaricatum ATCC14020
Brevibacterium taipei ATCC13744 and
Microbacterium ammoniaphilum ATCC21645 and mutants or strains, such as are known from the prior art, produced therefrom which produce chemical compounds.

Suitable strains of the species *Corynebacterium ammoniagenes* (*C. ammoniagenes*) are, in particular, the known wild-type strains Brevibacterium ammoniagenes ATCC6871
Brevibacterium ammoniagenes ATCC15137 and
Corynebacterium sp. ATCC21084 and mutants or strains, such as are known from the prior art, produced therefrom which produce chemical compounds.

Suitable strains of the species *Corynebacterium thermoaminogenes* (*C. thermoaminogenes*) are, in particular, the known wild-type strains Corynebacterium thermoaminogenes FERM BP-1539
Corynebacterium thermoaminogenes FERM BP-1540
Corynebacterium thermoaminogenes FERM BP-1541 and
Corynebacterium thermoaminogenes FERM BP-1542 and mutants or strains, such as are known from the prior art, produced therefrom which produce chemical compounds.

Strains with the designation "ATCC" can be obtained from the American Type Culture Collection (Manassas, Va., USA). Strains with the designation "FERM" can be obtained from the National Institute of Advanced Industrial Science and Technology (AIST Tsukuba Central 6, 1-1-1 Higashi, Tsukuba Ibaraki, Japan). The strains of *Corynebacterium thermoaminogenes* mentioned (FERM BP-1539, FERM BP-1540, FERM BP-1541 and FERM BP-1542) are described in U.S. Pat. No. 5,250,434.

Open reading frame (ORF) describes a section of a nucleotide sequence which codes or can code for a protein or polypeptide or ribonucleic acid to which no function can be assigned according to the prior art.

After assignment of a function to the nucleotide sequence section in question, it is in general referred to as a gene.

Alleles are in general understood as meaning alternative forms of a given gene. The forms are distinguished by differences in the nucleotide sequence.

In the context of the present invention, endogenous, that is to say species-characteristic, open reading frames, genes or alleles are preferably used. These are understood as meaning the open reading frames, genes or alleles or nucleotide sequences thereof present in the population of a species, such as, for example, *Corynebacterium glutamicum*.

"A copy of an open reading frame (ORF), a gene or allele present at the natural site (locus)" in the context of this invention is understood as meaning the position or situation of the ORF or gene or allele in relation to the adjacent ORFs or genes or alleles such as exists in the corresponding wild-type or corresponding parent organism or starting organism.

Thus, for example, the natural site of the lysC gene or of an lysC$^{FBR}$ allele, which codes for a "feed back" resistant aspartate kinase from *Corynebacterium glutamicum* is the lysC site or lysC locus or lysC gene site with the directly adjacent genes or open reading frames orfX and leuA on one flank and the asd gene on the other flank.

"Feed back" resistant aspartate kinase is understood as meaning aspartate kinases which, compared with the wild-type form, have a lower sensitivity to inhibition by mixtures of lysine and threonine or mixtures of AEC (aminoethylcysteine) and threonine or lysine by itself or AEC by itself. Strains which produce L-lysine typically contain such "feed back" resistant or desensitized aspartate kinases.

The nucleotide sequence of the chromosome of *Corynebacterium glutamicum* is known and can be found in Patent Application EP-A-1108790 and Access Number (Accession No.) AX114121 of the nucleotide sequence databank of the European Molecular Biologies Laboratories (EMBL, Heidelberg, Germany and Cambridge, UK). The nucleotide sequences of orfX, the leuA gene and the asd gene have the Access Numbers AX120364 (orfX), AX123517 (leuA) and AX123519 (asd).

Other datenbanks e. g. the National Center for Biotechnology Information (NCBI) of the National Library of Medicin (Bethesda, Md., USA) may be also be used.

Further databanks, such as, for example, that of the National Center for Biotechnology Information (NCBI, Bethesda, Md., USA) or that of the Swiss Institute of Bioinformatics (Swissprot, Geneva, Switzerland) or that of the Protein Information Resource Database (PIR, Washington, D.C., USA) can also be used.

"In each case a second, optionally third or fourth site" is understood as meaning a site which differs from the "natural site". It is also called a "target site" or "target sequence" in the following. It can also be called an "integration site" or "transformation site". This second, optionally third or fourth site, or the nucleotide sequence present at the corresponding sites, is preferably in the chromosome and is in general not essential for growth and for production of the desired chemical compounds.

To produce the coryneform bacteria according to the invention, the nucleotide sequence of the desired ORF, gene or allele, optionally including expression and/or regulation signals, is isolated and provided with nucleotide sequences of the target site at the ends, these are then transferred into the desired coryneform bacterium, preferably with the aid of vectors which do not replicate or replicate to only a limited extent in coryneform bacteria, and those bacteria in which the desired ORF, gene or allele is incorporated at the target site are isolated, no nucleotide sequence which is capable of/enables episomal replication in microorganisms, no nucleotide sequence which is capable of/enables transposition and no nucleotide sequence which imparts resistance to antibiotics remaining at the target site.

The invention accordingly also provides a process for the production of coryneform bacteria which produce one or more chemical compounds, which comprises
 a) isolating the nucleotide sequence of at least one desired ORF, gene or allele, optionally including the expression and/or regulation signals,
 b) providing the 5' and the 3' end of the ORF, gene or allele with nucleotide sequences of the target site,
 c) preferably incorporating the nucleotide sequence of the desired ORF, gene or allele provided with nucleotide sequences of the target site into a vector which does not replicate or replicates to only a limited extent in coryneform bacteria,
 d) transferring the nucleotide sequence according to b) or c) into coryneform bacteria, and
 e) isolating coryneform bacteria in which the nucleotide sequence according to a) is incorporated at the target site, no nucleotide sequence which is capable of/enables episomal replication in microorganisms, no nucleotide sequence which is capable of/enables transposition and no nucleotide sequence which imparts resistance to antibiotics remaining at the target site.

Preferably, also, no residues of sequences of the vectors used or species-foreign DNA, such as, for example, restriction cleavage sites, remain at the target site. A maximum of 24, preferably a maximum of 12, particularly preferably a maximum of 6 nucleotides of such DNA upstream or downstream of the ORF, gene or allele incorporated optionally remain at the target site.

By the measures according to the invention, the productivity of the coryneform bacteria or of the fermentative processes for the preparation of chemical compounds is improved in respect of one or more of the features chosen from the group consisting of concentration (chemical compound formed, based on the unit volume), yield (chemical compound formed, based on the source of carbon consumed) and product formation rate (chemical compound formed, based on the time) by at least 0.5–1.0% or at least 1.0 to 1.5% or at least 1.5–2.0%.

Instructions on conventional genetic engineering methods, such as, for example, isolation of chromosomal DNA, plasmid DNA, handling of restriction enzymes etc., are found in Sambrook et al. (Molecular Cloning—A Laboratory Manual (1989) Cold Spring Harbor Laboratory Press). Instructions on transformation and conjugation in coryneform bacteria are found, inter alia, in Thierbach et al. (Applied Microbiology and Biotechnology 29, 356–362 (1988)), in Schäfer et al. (Journal of Bacteriology 172, 1663–1666 (1990) and Gene 145, 69–73 (1994)) and in Schwarzer and Pühler (Bio/Technology 9, 84–87 (1991)).

Vectors which replicate to only a limited extent are understood as meaning plasmid vectors which, as a function of the conditions under which the host or carrier is cultured, replicate or do not replicate. Thus, a temperature-sensitive plasmid for coryneform bacteria which can replicate only at temperatures below 31° C. has been described by Nakamura et al. (U.S. Pat. No. 6,303,383).

The invention furthermore provides coryneform bacteria, in particular of the genus *Corynebacterium*, which produce L-lysine, characterized in that these have, in addition to at least one of the copy of an open reading frame (ORF), gene or allele of lysine production present at the natural site (locus), in each case a second, optionally third or fourth copy of the open reading frame (ORF), gene or allele in question at in each case a second, optionally third or fourth site in integrated form, no nucleotide sequence which is capable of/enables episomal replication in microorganisms, no nucleotide sequence which is capable of/enables transposition and no nucleotide sequence which imparts resistance to antibiotics being present at the particular second, optionally third or fourth site.

The invention also furthermore provides a process for the preparation of L-lysine, which comprises the following steps:
 a) fermentation of coryneform bacteria, in particular *Corynebacterium glutamicum*, characterized in that these have, in addition to at least one of the copy of an open reading frame (ORF), gene or allele of lysine production present at the natural site (locus), in each case a second, optionally third or fourth copy of the open reading frame (ORF), gene or allele in question at in each case a second, optionally third or fourth site in integrated form, no nucleotide sequence which is capable of/enables episomal replication in microorganisms, no nucleotide sequence which is capable of/enables transposition and no nucleotide sequence which imparts resistance to antibiotics being present at the particular second, optionally third or fourth site,
 under conditions which allow expression of the said open reading frames (ORF), genes or alleles,
 b) concentration of the L-lysine in the fermentation broth,
 c) isolation of the L-lysine from the fermentation broth, optionally
 d) with constituents from the fermentation broth and/or the biomass to the extent of > (greater than) 0 to 100%.

A "copy of an open reading frame (ORF), gene or allele of lysine production" is to be understood as meaning all the, preferably endogenous, open reading frames, genes or alleles of which enhancement/over-expression can have the effect of improving lysine production. Enhancement is understood as meaning an increase in the intracellular concentration or activity of the particular gene product, protein or enzyme.

These include, inter alia, the following open reading frames, genes or alleles: accBC, accDA, cstA, cysD, cysE, cysH, cysK, cysN, cysQ, dapA, dapB, dapC, dapD, dapE, dapF, ddh, dps, eno, gap, gap2, gdh, gnd, lysC, lysC$^{FBR}$, lysE, msiK, opcA, oxyR, ppc, ppc$^{FBR}$, pgk, pknA, pknB, pknD, pknG, ppsA, ptsH, ptsI, ptsM, pyc, pyc P458S, sigC, sigD, sigE, sigH, sigM, tal, thyA, tkt, tpi, zwa1, zwf and zwf A213T. These are summarized and explained in Table 1.

These include, in particular, the lysC$^{FBR}$ alleles which code for a "feed back" resistant aspartate kinase. Various lysC$^{FBR}$ alleles are summarized and explained in Table 2.

The following lysC$^{FBR}$ alleles are preferred: lysC A279T (replacement of alanine at position 279 of the aspartate kinase protein coded, according to SEQ ID NO: 2, by threonine), lysC A279V (replacement of alanine at position 279 of the aspartate kinase protein coded, according to SEQ ID NO: 2, by valine), lysC S301F (replacement of serine at position 301 of the aspartate kinase protein coded, according to SEQ ID NO: 2, by phenylalanine), lysC T308I (replacement of threonine at position 308 of the aspartate kinase protein coded, according to SEQ ID NO: 2, by isoleucine), lysC S301Y (replacement of serine at position 308 of the aspartate kinase protein coded, according to SEQ ID NO: 2, by tyrosine), lysC G345D (replacement of glycine at position 345 of the aspartate kinase protein coded, according to SEQ ID NO: 2, by aspartic acid), lysC R320G (replacement of arginine at position 320 of the aspartate kinase protein coded, according to SEQ ID NO: 2, by glycine), lysC T311I (replacement of threonine at position 311 of the aspartate kinase protein coded, according to SEQ ID NO: 2, by isoleucine), lysC S381F (replacement of serine at position 381 of the aspartate kinase protein coded, according to SEQ ID NO: 2, by phenylalanine).

The lysC$^{FBR}$ allele lysC T311I (replacement of threonine at position 311 of the aspartate kinase protein coded, according to SEQ ID NO: 2, by isoleucine), the nucleotide sequence of which is shown as SEQ ID NO:3, is particularly preferred; the amino acid sequence of the aspartate kinase protein coded is shown as SEQ ID NO:4.

The second, optionally third or fourth copy of the open reading frame (ORF), gene or allele of lysine production in question can be integrated at in each case a second, optionally third or fourth site. The following open reading frames, genes or nucleotide sequences, inter alia, can be used for this: aecD, ccpA1, ccpA2, citA, citB, citE, fda, gluA, gluB, gluC, gluD, luxR, luxS, lysR1, lysR2, lysR3, menE, mqo, pck, pgi, poxB and zwa2, in particular the genes aecD, gluA, gluB, gluC, gluD and pck. These are summarized and explained in Table 3.

The sites mentioned include, of course, not only the coding regions of the open reading frames or genes mentioned, but also the regions or nucleotide sequences lying upstream which are responsible for expression and regulation, such as, for example, ribosome binding sites, promoters, binding sites for regulatory proteins, binding sites for regulatory ribonucleic acids and attenuators. These regions in general lie in a range of 1–800, 1–600, 1–400, 1–200, 1–100 or 1–50 nucleotides upstream of the coding region. In the same way, regions lying downstream, such as, for example, transcription terminators, are also included. These regions in general lie in a range of 1–400, 1–200, 1–100, 1–50 or 1–25 nucleotides downstream of the coding region.

Intergenic regions in the chromosome, that is to say nucleotide sequences without a coding function, can furthermore be used. Finally, prophages or defective phages contained in the chromosome can be used for this.

A prophage is understood as meaning a bacteriophage, in particular the genome thereof, where this is replicated together with the genome of the host and the formation of infectious particles does not take place. A defective phage is understood as meaning a prophage, in particular the genome thereof, which, as a result of various mutations, has lost the ability to form so-called infectious particles. Defective phages are also called cryptic. Prophages and defective phages are often present in integrated form in the chromosome of their host. Further details exist in the prior art, for example in the textbook by Edward A. Birge (Bacterial and Bacteriophage Genetics, 3$^{rd}$ ed., Springer-Verlag, New York, USA, 1994) or in the textbook by S. Klaus et al. (Bakterienviren, Gustav Fischer Verlag, Jena, Germany, 1992).

Examples of regions of the *Corynebacterium glutamicum* chromosome representing intergenic regions, prophages, defective phages or phage components are shown in tables 12 and 13. The positions of the DNA regions refer to the genome map of *Corynebacterium glutamicum* ATCC 13032 as presented in EP-A-1108790 or in the databank of the European Molecular Biologies Laboratories (EMBL, Heidelberg, Germany and Cambridge, UK).

TABLE 1

Open reading frames, genes and alleles of lysine production

| Name | Description of the coded enzyme or protein | Reference | Access Number |
|---|---|---|---|
| accBC | Acyl-CoA Carboxylase EC 6.3.4.14 (acyl-CoA carboxylase) | Jäger et al. Archives of Microbiology (1996) 166:76–82 EP1108790; WO0100805 | U35023 AX123524 AX066441 |
| accDA | Acetyl-CoA Carboxylase EC 6.4.1.2 (acetyl-CoA carboxylase) | EP1055725 EP1108790 WO0100805 | AX121013 AX066443 |
| cstA | Carbon Starvation Protein A (carbon starvation protein A) | EP1108790 WO0100804 | AX120811 AX066109 |
| cysD | Sulfate Adenylyltransferase sub-unit II EC 2.7.7.4 | EP1108790 | AX123177 |

TABLE 1-continued

Open reading frames, genes and alleles of lysine production

| Name | Description of the coded enzyme or protein | Reference | Access Number |
|---|---|---|---|
| | (sulfate adenylyltransferase small chain) | | |
| cysE | Serine Acetyltransferase EC 2.3.1.30 (serine acetyltransferase) | EP1108790 WO0100843 | AX122902 AX063961 |
| cysH | 3'-Phosphoadenyl Sulfate Reductase EC 1.8.99.4 (3'-phosphoadenosine 5'-phosphosulfate reductase) | EP1108790 WO0100842 | AX123178 AX066001 |
| cysK | Cysteine Synthase EC 4.2.99.8 (cysteine synthase) | EP1108790 WO0100843 | AX122901 AX063963 |
| cysN | Sulfate Adenylyltransferase sub-unit I EC 2.7.7.4 (sulfate adenylyltransferase) | EP1108790 | AX123176 AX127152 |
| cysQ | Transport Protein CysQ (transporter cysQ) | EP1108790 WO0100805 | AX127145 AX066423 |
| dapA | Dihydrodipicolinate Synthase EC 4.2.1.52 (dihydrodipicolinate synthase) | Bonnassie et al. Nucleic Acids Research 18:6421 (1990) Pisabarro et al., Journal of Bacteriology 175:2743–2749 (1993) EP1108790 WO0100805 EP0435132 EP1067192 EP1067193 | X53993 Z21502 AX123560 AX063773 |
| dapB | Dihydrodipicolinate Reductase EC 1.3.1.26 (dihydrodipicolinate reductase) | EP1108790 WO0100843 EP1067192 EP1067193 Pisabarro et al., Journal of Bacteriology 175:2743–2749 (1993) JP1998215883 JP1997322774 JP1997070291 JP1995075578 | AX127149 AX063753 AX137723 AX137602 X67737 Z21502 E16749 E14520 E12773 E08900 |
| dapC | N-Succinyl Aminoketopimelate Transaminase EC 2.6.1.17 (N-succinyl diaminopimelate transaminase) | EP1108790 WO0100843 EP1136559 | AX127146 AX064219 |
| dapD | Tetrahydrodipicolinate Succinylase EC 2.3.1.117 (tetrahydrodipicolinate succinylase) | EP1108790 WO0100843 Wehrmann et al. Journal of Bacteriology 180:3159–3165 (1998) | AX127146 AX063757 AJ004934 |
| dapE | N-Succinyl Diaminopimelate Desuccinylase EC 3.5.1.18 (N-succinyl diaminopimelate desuccinylase) | EP1108790 WO0100843 Wehrmann et al. Microbiology 140:3349–3356 (1994) | AX127146 AX063749 X81379 |
| dapF | Diaminopimelate Epimerase EC 5.1.1.7 (diaminopimelate epimerase) | EP1108790 WO0100843 EP1085094 | AX127149 AX063719 AX137620 |
| ddh | Diaminopimelate Dehydrogenase EC 1.4.1.16 (diaminopimelate dehydrogenase) | EP1108790 WO0100843 Ishino et al., Nucleic Acids Research 15:3917–3917 (1987) JP1997322774 | AX127152 AX063759 Y00151 E14511 |

TABLE 1-continued

Open reading frames, genes and alleles of lysine production

| Name | Description of the coded enzyme or protein | Reference | Access Number |
|---|---|---|---|
| | | JP1993284970 | E05776 |
| | | Kim et al., Journal of Microbiology and Biotechnology 5:250–256(1995) | D87976 |
| dps | DNA Protection Protein (protection during starvation protein) | EP1108790 | AX127153 |
| eno | Enolase EC 4.2.1.11 (enolase) | EP1108790 WO0100844 EP1090998 Hermann et al., Electrophoresis 19:3217–3221 (1998) | AX127146 AX064945 AX136862 |
| gap | Glyceraldehyde 3-Phosphate Dehydrogenase EC 1.2.1.12 (glyceraldehyde 3-phosphate dehydrogenase) | EP1108790 WO0100844 Eikmanns et al., Journal of Bacteriology 174:6076–6086 (1992) | AX127148 AX064941 X59403 |
| gap2 | Glyceraldehyde 3-Phosphate Dehydrogenase EC 1.2.1.12 (glyceraldehyde 3-phosphate dehydrogenase 2) | EP1108790 WO0100844 | AX127146 AX064939 |
| gdh | Glutamate Dehydrogenase EC 1.4.1.4 (glutamate dehydrogenase) | EP1108790 WO0100844 Boermann et al., Molecular Microbiology 6:317–326 (1992) Guyonvarch et al., NCBI | AX127150 AX063811 X59404 X72855 |
| gnd | 6-Phosphogluconate Dehydrogenase EC 1.1.1.44 (6-phosphogluconate dehydrogenase) | EP1108790 WO0100844 | AX127147 AX121689 AX065125 |
| lysC | Aspartate Kinase EC 2.7.2.4 (aspartate kinase) | EP1108790 WO0100844 Kalinowski et al., Molecular Microbiology 5:1197–204 (1991) | AX120365 AX063743 X57226 |
| lysC$^{FBR}$ | Aspartate Kinase feedback resistant (fbr) EC 2.7.2.4 (aspartate kinase fbr) | see Table 2 | |
| lysE | Lysine Exporter (lysine exporter protein) | EP1108790 WO0100843 Vrljić et al., Molecular Microbiology 22:815–826 (1996) | AX123539 AX123539 X96471 |
| msiK | Sugar Importer (multiple sugar import protein) | EP1108790 | AX120892 |
| opcA | Glucose 6-phosphate Dehydrogenase (subunit of glucose 6-phosphate dehydrogenase) | WO0104325 | AX076272 |
| oxyR | Transcription Regulator (transcriptional regulator) | EP1108790 | AX122198 AX127149 |
| ppc$^{FBR}$ | Phosphoenol Pyruvate Carboxylase feedback resistant EC 4.1.1.31 (phosphoenol pyruvate carboxylase) feedback resistant) | EP0723011 WO0100852 | |
| ppc | Phosphoenol Pyruvate Carboxylase EC 4.1.1.31 (phosphoenol pyruvate carboxylase) | EP1108790 O'Reagan et | AX127148 AX123554 M25819 |

TABLE 1-continued

Open reading frames, genes and alleles of lysine production

| Name | Description of the coded enzyme or protein | Reference | Access Number |
|---|---|---|---|
| | | al., Gene 77(2):237–251 (1989) | |
| pgk | Phosphoglycerate Kinase EC 2.7.2.3 (phosphoglycerate kinase) | EP1108790 WO0100844 Eikmanns, Journal of Bacteriology 174:6076–6086 (1992) | AX121838 AX127148 AX064943 X59403 |
| pknA | Protein Kinase A (protein kinase A) | EP1108790 | AX120131 AX120085 |
| pknB | Protein Kinase B (protein kinase B) | EP1108790 | AX120130 AX120085 |
| pknD | Protein Kinase D (protein kinase D) | EP1108790 | AX127150 AX122469 AX122468 |
| pknG | Protein Kinase G (protein kinase G) | EP1108790 | AX127152 AX123109 |
| ppsA | Phosphoenol Pyruvate Synthase EC 2.7.9.2 (phosphoenol pyruvate synthase) | EP1108790 | AX127144 AX120700 AX122469 |
| ptsH | Phosphotransferase System Protein H EC 2.7.1.69 (phosphotransferase system component H) | EP1108790 WO0100844 | AX122210 AX127149 AX069154 |
| ptsI | Phosphotransferase System Enzyme I EC 2.7.3.9 (phosphotransferase system enzyme I) | EP1108790 | AX122206 AX127149 |
| ptsM | Glukose-specific Phosphotransferase System Enzyme II EC 2.7.1.69 (glucose phosphotransferase system enzyme II) | Lee et al., FEMS Microbiology Letters 119 (1–2):137–145 (1994) | L18874 |
| pyc | Pyruvate Carboxylase EC 6.4.1.1 (pyruvate carboxylase) | WO9918228 Peters-Wendisch et al., Microbiology 144:915–927 (1998) | A97276 Y09548 |
| pyc P458S | Pyruvate Carboxylase EC 6.4.1.1 (pyruvate carboxylase) amino acid exchange P458S | EP1108790 | |
| sigC | Sigma Factor C EC 2.7.7.6 (extracytoplasmic function alternative sigma factor C) | EP1108790 | AX120368 AX120085 |
| sigD | RNA Polymerase Sigma Factor D EC 2.7.7.6 (RNA polymerase sigma factor) | EP1108790 | AX120753 AX127144 |
| sigE | Sigma Factor E EC 2.7.7.6 (extracytoplasmic function alternative sigma factor E) | EP1108790 | AX127146 AX121325 |
| sigH | Sigma Factor H EC 2.7.7.6 (sigma factor SigH) | EP1108790 | AX127145 AX120939 |
| sigM | Sigma Factor M EC 2.7.7.6 (sigma factor SigM) | EP1108790 | AX123500 AX127145 |
| tal | Transaldolase EC 2.2.1.2 (transaldolase) | WO0104325 | AX076272 |
| thyA | Thymidylate Synthase EC 2.1.1.45 (thymidylate synthase) | EP1108790 | AX121026 AX127145 |
| tkt | Transketolase EC 2.2.1.1 (transketolase) | Ikeda et al., NCBI | AB023377 |
| tpi | Triose Phosphate Isomerase | Eikmanns, | X59403 |

TABLE 1-continued

Open reading frames, genes and alleles of lysine production

| Name | Description of the coded enzyme or protein | Reference | Access Number |
|---|---|---|---|
| | EC 5.3.1.1 (triose phosphate isomerase) | Journal of Bacteriology 174:6076–6086 (1992) | |
| zwa1 | Cell Growth Factor 1 (growth factor 1) | EP1111062 | AX133781 |
| zwf | Glucose 6-phosphate 1-Dehydrogenase EC 1.1.1.49 (glucose 6-phosphate 1-dehydrogenase) | EP1108790 WO0104325 | AX127148 AX121827 AX076272 |
| zwf A213T | Glucose 6-phosphate 1-Dehydrogenase EC 1.1.1.49 (glucose 6-phosphate 1-dehydrogenase) amino acid exchange A213T | EP1108790 | |

TABLE 2 lysC$^{FBR}$ alleles which code for feed back resistant aspartate kinases

| Name of the allele | Further information | Reference | Access Number |
|---|---|---|---|
| lysC$^{FBR}$-E05108 | | JP 1993184366-A (sequence 1) | E05108 |
| lysC$^{FBR}$-E06825 | lysC A279T | JP 1994062866-A (sequence 1) | E06825 |
| lysC$^{FBR}$-E06826 | lysC A279T | JP 1994062866-A (sequence 2) | E06826 |
| lysC$^{FBR}$-E06827 | | JP 1994062866-A (sequence 3) | E06827 |
| lysC$^{FBR}$-E08177 | | JP 1994261766-A (sequence 1) | E08177 |
| lysC$^{FBR}$E08178 | lysC A279T | JP 1994261766-A (sequence 2) | E08178 |
| lysC$^{FBR}$-E08179 | lysC A279V | JP 1994261766-A (sequence 3) | E08179 |
| lysC$^{FBR}$-E08180 | lysC S301F | JP 1994261766-A (sequence 4) | E08180 |
| lysC$^{FBR}$-E08181 | lysC T308I | JP 1994261766-A (sequence 5) | E08181 |
| lysC$^{FBR}$-E08182 | | JP 1994261766-A (sequence 6) | E08182 |
| lysC$^{FBR}$-E12770 | | JP 1997070291-A (sequence 13) | E12770 |
| lysC$^{FBR}$-E14514 | | JP 1997322774-A (sequence 9) | E14514 |
| lysC$^{FBR}$-E16352 | | JP 1998165180-A (sequence 3) | E16352 |
| lysC$^{FBR}$-E16745 | | JP 1998215883-A (sequence 3) | E16745 |
| lysC$^{FBR}$-E16746 | | JP 1998215883-A (sequence 4) | E16746 |
| lysC$_{FBR}$-I74588 | | US 5688671-A (sequence 1) | I74588 |
| lysC$^{FBR}$-I74589 | lysC A279T | US 5688671-A (sequence 2) | I74589 |
| lysC$^{FBR}$-I74590 | | US 5688671-A (sequence 7) | I74590 |
| lysC$^{FBR}$-I74591 | lysC A279T | US 5688671-A (sequence 8) | I74591 |
| lysC$_{FBR}$-I74592 | | US 5688671-A (sequence 9) | I74592 |
| lysC$^{FBR}$-I74593 | lysC A279T | US 5688671-A (sequence 10) | I74593 |
| lysC$^{FBR}$-I74594 | | US 5688671-A (sequence 11) | I74594 |
| lysC$^{FBR}$-I74595 | lysC A279T | US 5688671-A (sequence 12) | I74595 |
| lysC$^{FBR}$-I74596 | | US 5688671-A (sequence 13) | I74596 |
| lysC$^{FBR}$-I74597 | lysC A279T | US 5688671-A (sequence 14) | I74597 |
| lysC$^{FBR}$-X57226 | lysC S301Y | EP0387527 Kalinowski et al., Molecular and General Genetics 224:317–324 (1990) | X57226 |
| lysC$^{FBR}$-L16848 | lysC G345D | Follettie and Sinskey NCBI Nucleotide Database (1990) | L16848 |
| lysC$^{FBR}$-L27125 | lysC R320G lysC G345D | Jetten et al., Applied Microbiology Biotechnology 43:76–82 (1995) | L27125 |
| lysC$^{FBR}$ | lysC T311I | WO0063388 (sequence 17) | |
| lysC$^{FBR}$ | lysC S301F | US3732144 | |
| lysC$^{FBR}$ | lysC S381F | | |
| lysC$^{FBR}$ | | JP6261766 (sequence 1) | |
| lysC$^{FBR}$ | lysC A279T | JP6261766 (sequence 2) | |
| lysC$^{FBR}$ | lysC A279V | JP6261766 (sequence 3) | |
| lysC$^{FBR}$ | lysC S301F | JP6261766 (sequence 4) | |
| lysC$^{FBR}$ | lysC T308I | JP6261766 (sequence 5) | |

TABLE 3

Target sites for integration of open reading frames, genes and alleles of lysine production

| Gene name | Description of the coded enzyme or protein | Reference | Access Number |
|---|---|---|---|
| aecD | beta C-S Lyase EC 2.6.1.1 | Rossol et al., Journal of | M89931 |

TABLE 3-continued

Target sites for integration of open reading frames, genes and alleles of lysine production

| Gene name | Description of the coded enzyme or protein | Reference | Access Number |
|---|---|---|---|
| | (beta C-S lyase) | Bacteriology 174(9):2968–77 (1992) | |
| ccpA1 | Catabolite Control Protein (catabolite control protein A1) | WO0100844 EP1108790 | AX065267 AX127147 |
| ccpA2 | Catabolite Control Protein (catabolite control protein A2) | WO0100844 EP1108790 | AX065267 AX121594 |
| citA | Sensor Kinase CitA (sensor kinase CitA) | EP1108790 | AX120161 |
| citB | Transcription Regulator CitB (transcription regulator CitB) | EP1108790 | AX120163 |
| citE | Citrate Lyase EC 4.1.3.6 (citrate lyase) | WO0100844 EP1108790 | AX065421 AX127146 |
| fda | Fructose Bisphosphate Aldolase EC 4.1.2.13 (fructose 1,6-bisphosphate aldolase) | von der Osten et al., Molecular Microbiology 3(11):1625–37 (1989) | X17313 |
| gluA | Glutamate Transport ATP-binding Protein (glutamate transport ATP-binding protein) | Kronemeyer et al., Journal of Bacteriology 177(5):1152–8 (1995) | X81191 |
| gluB | Glutamate-binding Protein (glutamate-binding protein) | Kronemeyer et al., Journal of Bacteriology 177(5):1152–8 (1995) | X81191 |
| gluC | Glutamate Transport Permease (glutamate transport system permease) | Kronemeyer et al., Journal of Bacteriology 177(5):1152–8 (1995) | X81191 |
| gluD | Glutamate Transport Permease (glutamate transport system permease) | Kronemeyer et al., Journal of Bacteriology 177(5):1152–8 (1995) | X81191 |
| luxR | Transcription Regulator LuxR (transcription regulator LuxR) | WO0100842 EP1108790 | AX065953 AX123320 |
| luxS | Histidine Kinase LuxS (histidine kinase LuxS) | EP1108790 | AX123323 AX127145 |
| lysR1 | Transcription Regulator LysR1 (transcription regulator LysR1) | EP1108790 | AX064673 AX127144 |
| lysR2 | Transcription Activator LysR2 (transcription regulator LysR2) | EP1108790 | AX123312 |
| lysR3 | Transcription Regulator LysR3 (transcription regulator LysR3) | WO0100842 EP1108790 | AX065957 AX127150 |
| menE | O-Succinylbenzoic Acid CoA Ligase EC 6.2.1.26 (O-succinylbenzoate CoA ligase) | WO0100843 EP1108790 | AX064599 AX064193 AX127144 |
| mqo | Malate-Quinone Oxidoreductase (malate-quinone-oxidoreductase) | Molenaar et al., Eur. Journal of Biochemistry 1;254 (2):395–403 (1998) | AJ224946 |
| pck | Phosphoenol Pyruvate Carboxykinase (phosphoenol pyruvate carboxykinase) | WO0100844 | AJ269506 AX065053 |
| pgi | Glucose 6-phosphate Isomerase EC 5.3.1.9 (glucose 6-phosphate isomerase) | EP1087015 EP1108790 | AX136015 AX127146 |
| poxB | Pyruvate Oxidase EC 1.2.3.3 (pyruvate oxidase) | WO0100844 EP1096013 | AX064959 AX137665 |
| zwa2 | Cell Growth Factor 2 (growth factor 2) | EP1106693 EP1108790 | AX113822 AX127146 |

The invention accordingly also provides a process for the production of coryneform bacteria which produce L-lysine, which comprises a) isolating the nucleotide sequence of at least one desired ORF, gene or allele of lysine production, optionally including the expression and/or regulation signals, b) providing the 5' and the 3' end of the ORF, gene or allele of lysine production with nucleotide sequences of the target site, c) preferably incorporating the nucleotide sequence of the desired ORF, gene or allele provided with nucleotide sequences of the target site into a vector which does not replicate or replicates to only a limited extent in coryneform bacteria, d) transferring the nucleotide sequence according to b) or c) into coryneform bacteria, and e) isolating coryneform bacteria in which the nucleotide sequence according to a) is incorporated at the target site, no nucleotide sequence which is capable of/enables episomal replication in microorganisms, no nucleotide sequence which is capable of/enables transposition and no nucleotide sequence which imparts resistance to antibiotics remaining at the target site.

The invention furthermore provides coryneform bacteria, in particular of the genus *Corynebacterium*, which produce L-methionine and/or L-threonine, characterized in that these have, in addition to at least one of the copy of an open reading frame (ORF), gene or allele of methionine production or threonine production present at the natural site (locus), in each case a second, optionally third or fourth copy of the open reading frame (ORF), gene or allele in question at in each case a second, optionally third or fourth site in integrated form, no nucleotide sequence which is capable of/enables episomal replication in microorganisms, no nucleotide sequence which is capable of/enables transposition and no nucleotide sequence which imparts resistance to antibiotics being present at the particular second, optionally third or fourth site.

The invention also furthermore provides a process for the preparation of L-methionine and/or L-threonine, which comprises the following steps:

a) fermentation of coryneform bacteria, in particular *Corynebacterium glutamicum*, characterized in that these have, in addition to at least one of the copy of an open reading frame (ORF), gene or allele of methionine production or threonine production present at the natural site (locus), in each case a second, optionally third or fourth copy of the open reading frame (ORF), gene or allele in question at in each case a second, optionally third or fourth site in integrated form, no nucleotide sequence which is capable of/enables episomal replication in microorganisms, no nucleotide sequence which is capable of/enables transposition and no nucleotide sequence which imparts resistance to antibiotics being present at the particular second, optionally third or fourth site,
under conditions which allow expression of the said open reading frames (ORF), genes or alleles,
b) concentration of the L-methionine and/or L-threonine in the fermentation broth,
c) isolation of the L-methionine and/or L-threonine from the fermentation broth, optionally
d) with constituents from the fermentation broth and/or the biomass to the extent of > (greater than) 0 to 100%.

A "copy of an open reading frame (ORF), gene or allele of methionine production" is to be understood as meaning all the, preferably endogenous, open reading frames, genes or alleles of which enhancement/over-expression can have the effect of improving methionine production.

These include, inter alia, the following open reading frames, genes or alleles: accBC, accDA, aecD, cstA, cysD, cysE, cysH, cysK, cysN, cysQ, dps, eno, fda, gap, gap2, gdh, gnd, glyA, hom, hom$^{FBR}$, lysC, lysC$^{FBR}$, metA, metB, metE, metH, metY, msiK, opcA, oxyR, ppc, ppc$^{FBR}$, pgk, pknA, pknB, pknD, pknG, ppsA, ptsH, ptsI, ptsM, pyc, pyc P458S, sigC, sigD, sigE, sigH, sigM, tal, thyA, tkt, tpi, zwa1, zwf and zwf A213T. These are summarized and explained in Table 4. These include, in particular, the lysC$^{FBR}$ alleles which code for a "feed back" resistant aspartate kinase (see Table 2) and the hom$^{FBR}$ alleles which code for a "feed back" resistant homoserine dehydrogenase.

The second, optionally third or fourth copy of the open reading frame (ORF), gene or allele of methionine production in question can be integrated at in each case a second, optionally third or fourth site. The following open reading frames, genes or nucleotide sequences, inter alia, can be used for this: brnE, brnF, brnQ, ccpA1, ccpA2, citA, citB, citE, ddh, gluA, gluB, gluC, gluD, luxR, luxS, lysR1, lysR2, lysR3, menE, metD, metK, pck, pgi, poxB and zwa2. These are summarized and explained in Table 5.

The sites mentioned include, of course, not only the coding regions of the open reading frames or genes mentioned, but also the regions or nucleotide sequences lying upstream which are responsible for expression and regulation, such as, for example, ribosome binding sites, promoters, binding sites for regulatory proteins, binding sites for regulatory ribonucleic acids and attenuators. These regions in general lie in a range of 1–800, 1–600, 1–400, 1–200, 1–100 or 1–50 nucleotides upstream of the coding region. In the same way, regions lying downstream, such as, for example, transcription terminators, are also included. These regions in general lie in a range of 1–400, 1–200, 1–100, 1–50 or 1–25 nucleotides downstream of the coding region.

Intergenic regions in the chromosome, that is to say nucleotide sequences without a coding function, can furthermore be used. Finally, prophages or defective phages contained in the chromosome can be used for this.

Examples of regions of the *Corynebacterium glutamicum* chromosome representing intergenic regions, prophages, defective phages or phage components are shown in tables 12 and 13. The positions of the DNA regions refer to the genome map of *Corynebacterium glutamicum* ATCC 13032 as presented in EP-A-1108790 or in the databank of the European Molecular Biologies Laboratories (EMBL, Heidelberg, Germany and Cambridge, UK).

TABLE 4

Open reading frames, genes and alleles of methionine production

| Name | Description of the coded enzyme or protein | Reference | Access Number |
|---|---|---|---|
| AccBC | Acyl-CoA Carboxylase EC 6.3.4.14 (acyl-CoA carboxylase) | Jäger et al. Archives of Microbiology (1996) 166:76–82 EP1108790; WO0100805 | U35023 AX123524 AX066441 |
| AccDA | Acetyl-CoA Carboxylase EC 6.4.1.2 (acetyl-CoA carboxylase) | EP1055725 EP1108790 WO0100805 | AX121013 AX066443 |
| AecD | Cystathionine beta-Lyase EC 4.4.1.8 (cystathionine beta-lyase) | Rossol et al., Journal of Bacteriology 174:2968–2977 (1992) | M89931 |
| CstA | Carbon Starvation Protein A (carbon starvation protein A) | EP1108790 WO0100804 | AX120811 AX066109 |
| CysD | Sulfate Adenylyltransferase sub-unit II EC 2.7.7.4 (sulfate adenylyltransferase small chain) | EP1108790 | AX123177 |
| CysE | Serine Acetyltransferase EC 2.3.1.30 (serine acetyltransferase) | EP1108790 WO0100843 | AX122902 AX063961 |
| CysH | 3'-Phosphoadenyl Sulfate Reductase EC 1.8.99.4 (3'-phosphoadenosine 5'-phosphosulfate reductase) | EP1108790 WO0100842 | AX123178 AX066001 |

TABLE 4-continued

Open reading frames, genes and alleles of methionine production

| Name | Description of the coded enzyme or protein | Reference | Access Number |
|---|---|---|---|
| CysK | Cysteine Synthase<br>EC 4.2.99.8<br>(cysteine synthase) | EP1108790<br>WO0100843 | AX122901<br>AX063963 |
| CysN | Sulfate Adenylyltransferase sub-unit I<br>EC 2.7.7.4<br>(sulfate adenylyltransferase) | EP1108790 | AX123176<br>AX127152 |
| CysQ | Transport protein CysQ<br>(transporter cysQ) | EP1108790<br>WO0100505 | AX127145<br>AX066423 |
| Dps | DNA Protection Protein<br>(protection during starvation protein) | EP1108790 | AX127153 |
| Eno | Enolase<br>EC 4.2.1.11<br>(enolase) | EP1108790<br>WO0100844<br>EP1090998<br>Hermann et al.,<br>Electrophoresis<br>19:3217–3221<br>(1998) | AX127146<br>AX064945<br>AX136862 |
| Fda | Fructose Bisphosphate Aldolase<br>EC 4.1.2.13<br>(fructose bisphosphate aldolase) | van der Osten et al., Molecular Microbiology 3:1625–1637 (1989) | X17313 |
| Gap | Glyceraldehyde 3-Phosphate Dehydrogenase<br>EC 1.2.1.12<br>(glyceraldehyde 3-phosphate dehydrogenase) | EP1108790<br>WO0100844<br>Eikmanns et al., Journal of Bacteriology 174:6076–6086(1992) | AX127148<br>AX064941<br>X59403 |
| gap2 | Glyceraldehyde 3-Phosphate Dehydrogenase<br>EC 1.2.1.12<br>(glyceraldehyde 3-phosphate dehydrogenase 2) | EP1108790<br>WO0100844 | AX127146<br>AX064939 |
| Gdh | Glutamate Dehydrogenase<br>EC 1.4.1.4<br>(glutamate dehydrogenase) | EP1108790<br>WO0100844<br>Boermann et al., Molecular Microbiology 6:317–326 (1992);<br>Guyonvarch et al., NCBI | AX127150<br>AX063811<br>X59404<br><br>X72855 |
| GlyA | Glycine/Serine Hydroxymethyltransferase<br>EC 2.1.2.1<br>(glycine/serine hydroxymethyltransferase) | EP1108790 | AX127146<br>AX121194 |
| Gnd | 6-Phosphogluconate Dehydrogenase<br>EC 1.1.1.44<br>(6-phosphogluconate dehydrogenase) | EP1108790<br><br>WO0100844 | AX127147<br>AX121689<br>AX065125 |
| Hom | Homoserine Dehydrogenase<br>EC 1.1.1.3<br>(homoserine dehydrogenase) | Peoples et al., Molecular Microbiology 2:63–72 (1988) | Y00546 |
| hom$^{FBR}$ | Homoserine Dehydrogenase feedback resistant (fbr)<br>EC 1.1.1.3<br>(homoserine dehydrogenase fbr) | Reinscheid et al., Journal of Bacteriology 173:3228–30 (1991) | |
| LysC | Aspartate Kinase<br>EC 2.7.2.4<br>(aspartate kinase) | EP1108790<br>WO0100844<br>Kalinowski et al., Molecular Microbiology 5:1197–204 (1991) | AX120365<br>AX063743<br>X57226 |
| lysC$^{FBR}$ | Aspartate Kinase feedback resistant (fbr)<br>EC 2.7.2.4<br>(aspartate kinase fbr) | see Table 2 | |

TABLE 4-continued

Open reading frames, genes and alleles of methionine production

| Name | Description of the coded enzyme or protein | Reference | Access Number |
|---|---|---|---|
| MetA | Homoserine Acetyltransferase EC 2.3.1.31 (homoserine acetyltransferase) | Park et al., Molecular Cells 8:286–94 (1998) | AF052652 |
| MetB | Cystathionine γ-Lyase EC 4.4.1.1 (cystathionine gamma-synthase) | Hwang et al., Molecular Cells 9:300–308 (1999) | AF126953 |
| MetE | Homocysteine Methyltransferase EC 2.1.1.14 (homocysteine methyltransferase) | EP1108790 | AX127146 AX121345 |
| MetH | Homocysteine Methyltransferase (Vitamin B12-dependent) EC 2.1.1.14 (homocysteine methyltransferase) | EP1108790 | AX127148 AX121747 |
| MetY | Acetylhomoserine Sulfhydrolase (acetylhomoserine sulfhydrolase) | EP1108790 | AX120810 AX127145 |
| MsiK | Sugar Importer (multiple sugar import protein) | EP1108790 | AX120892 |
| OpcA | Glucose 6-phosphate Dehydrogenase (subunit of glucose 6-phosphate dehydrogenase) | WO0104325 | AX076272 |
| OxyR | Transcription Regulator (transcriptional regulator) | EP1108790 | AX122198 AX127149 |
| ppc$^{FBR}$ | Phosphoenol Pyruvate Carboxylase feedback resistent EC 4.1.1.31 (phosphoenol pyruvate carboxylase feedback resistant) | EP0723011 WO0100852 | |
| Ppc | Phosphoenol Pyruvate Carboxylase EC 4.1.1.31 (phosphoenol pyruvate carboxylase) | EP1108790 O'Reagan et al., Gene 77(2):237–251 (1989) | AX127148 AX123554 M25819 |
| Pgk | Phosphoglycerate Kinase EC 2.7.2.3 (phosphoglycerate kinase) | EP1108790 WO0100844 Eikmanns, Journal of Bacteriology 174:6076–6086 (1992) | AX121838 AX127148 AX064943 X59403 |
| PknA | Protein Kinase A (protein kinase A) | EP1108790 | AX120131 AX120085 |
| PknB | Protein Kinase B (protein kinase B) | EP1108790 | AX120130 AX120085 |
| PknD | Protein Kinase D (protein Kinase D) | EP1108790 | AX127150 AX122469 AX122468 |
| PknG | Protein Kinase G (protein kinase G) | EP1108790 | AX127152 AX123109 |
| PpsA | Phosphoenol Pyruvate Synthase EC 2.7.9.2 (phosphoenol pyruvate synthase) | EP1108790 | AX127144 AX120700 AX122469 |
| PtsH | Phosphotransferase System Protein H EC 2.7.1.69 (phosphotransferase system component H) | EP1108790 WO0100844 | AX122210 AX127149 AX069154 |
| PtsI | Phosphotransferase System Enzyme I EC 2.7.3.9 (phosphotransferase system enzyme I) | EP1108790 | AX122206 AX127149 |
| PtsM | Glucose-specific Phosphotransferase System Enzyme II EC 2.7.1.69 (glucose phosphotransferase system enzyme II) | Lee et al., FEMS Microbiology Letters 119 (1–2):137–145 (1994) | L18874 |
| Pyc | Pyruvate Carboxylase EC 6.4.1.1 (pyruvate carboxylase) | WO9918228 Peters-Wendisch et al., Microbiology 144:915–927 (1998) | A97276 Y09548 |

TABLE 4-continued

Open reading frames, genes and alleles of methionine production

| Name | Description of the coded enzyme or protein | Reference | Access Number |
|---|---|---|---|
| Pyc P458s | Pyruvate Carboxylase EC 6.4.1.1 (pyruvate carboxylase) amino acid exchange P458S | EP1108790 | |
| SigC | Sigma Factor C EC 2.7.7.6 (extracytoplasmic function alternative sigma factor C) | EP1108790 | AX120368 AX120085 |
| SigD | RNA Polymerase Sigma Factor D EC 2.7.7.6 (RNA polymerase sigma factor) | EP1108790 | AX120753 AX127144 |
| SigE | Sigma Factor E EC 2.7.7.6 (extracytoplasmic function alternative sigma factor E) | EP1108790 | AX127146 AX121325 |
| SigH | Sigma Factor H EC 2.7.7.6 (sigma factor SigH) | EP1108790 | AX127145 AX120939 |
| SigM | Sigma Factor M EC 2.7.7.6 (sigma factor SigM) | EP1108790 | AX123500 AX127153 |
| Tal | Transaldolase EC 2.2.1.2 (transaldolase) | WO0104325 | AX076272 |
| ThyA | Thymidylate Synthase EC 2.1.1.45 (thymidylate synthase) | EP1108790 | AX121026 AX127145 |
| Tkt | Transketolase EC 2.2.1.1 (transktolase) | Ikeda et al., NCBI | AB023377 |
| Tpi | Triose Phosphate Isomerase EC 5.3.1.1 (triose phosphate isomerase) | Eikmanns, Journal of Bacteriology 174:6076–6086 (1992) | X59403 |
| zwa1 | Cell Growth Factor 1 (growth factor 1) | EP1111062 | AX133781 |
| Zwf | Glucose 6-phosphate 1-Dehydrogenase EC 1.1.1.49 (glucose 6-phosphate 1-dehydrogenase) | EP1108790 WO0104325 | AX127148 AX121827 AX076272 |
| Zwf A213T | Glucose 6-phosphate 1-Dehydrogenase EC 1.1.1.49 (glucose 6-phosphate 1-dehydrogenase) amino acid exchange A213T | EP1108790 | |

TABLE 5

Target sites for integration of open reading frames, genes and alleles of methionine production

| Gene name | Description of the coded enzyme or protein | Reference | Access Number |
|---|---|---|---|
| BrnE | Transporter of branched-chain amino acids (branched-chain amino acid transporter) | EP1096010 | AX137709 AX137714 |
| BrnF | Transporter of branched-chain amino acids (branched-chain amino acid transporter) | EP1096010 | AX137709 AX137714 |
| BrnQ | Carrier protein of branched-chain amino acids (branched-chain amino acid transport system carrier protein) | Tauch et al., Archives of Microbiology 169(4):303–12 (1998) | M89931 AX066841 AX127150 WO0100805 EP1108790 |
| ccpA1 | Catabolite Control Protein (catabolite control protein A1) | WO0100844 EP1108790 | AX065267 AX127147 |
| ccpA2 | Catabolite Control Protein (catabolite control protein A2) | WO0100844 EP1108790 | AX065267 AX121594 |
| citA | Sensor Kinase CitA (sensor kinase CitA) | EP1108790 | AX120161 |

TABLE 5-continued

Target sites for integration of open reading frames, genes and alleles of methionine production

| Gene name | Description of the coded enzyme or protein | Reference | Access Number |
|---|---|---|---|
| citB | Transcription Regulator CitB (transcription regulator CitB) | EP1108790 | AX120163 |
| citE | Citrate Lyase EC 4.1.3.6 (citrate lyase) | WO0100844 EP1108790 | AX065421 AX127146 |
| ddh | Diaminopimelate Dehydrogenase EC 1.4.1.16 (diaminopimelate dehydrogenase) | Ishino et al., Nucleic Acids Research 15:3917 (1987) EP1108790 | S07384 AX127152 |
| gluA | Glutamate Transport ATP-binding Protein (glutamate transport ATP-binding protein) | Kronemeyer et al., Journal of Bacteriology 177(5):1152–8 (1995) | X81191 |
| gluB | Glutamate-binding Protein (glutamate-binding protein) | Kronemeyer et al., Journal of Bacteriology 177(5):1152–8 (1995) | X81191 |
| gluC | Glutamate Transport Permease (glutamate transport system permease) | Kronemeyer et al., Journal of Bacteriology 177(5):1152–8 (1995) | X81191 |
| gluD | Glutamate Transport Permease (glutamate transport system permease) | Kronemeyer et al., Journal of Bacteriology 177(5):1152–8 (1995) | X81191 |
| luxR | Transcription Regulator LuxR (transcription regulator LuxR) | WO0100842 EP1108790 | AX065953 AX123320 |
| luxS | Histidine Kinase LuxS (histidine kinase LuxS) | EP1108790 | AX123323 AX127145 |
| lysR1 | Transcription Regulator LysR1 (transcription regulator LysR1) | EP1108790 | AX064673 AX127144 |
| lysR2 | Transcription Activator LysR2 (transcription regulator LysR2) | EP1108790 | AX123312 |
| lysR3 | Transcription Regulator LysR3 (transcription regulator LysR3) | WO0100842 EP1108790 | AX065957 AX127150 |
| menE | O-Succinylbenzoic Acid CoA Ligase EC 6.2.1.26 (O-succinylbenzoate CoA ligase) | WO0100843 EP1108790 | AX064599 AX064193 AX127144 |
| metD | Transcription Regulator MetD (transcription regulator MetD) | EP1108790 | AX123327 AX127153 |
| metK | Methionine Adenosyl Transferase EC 2.5.1.6 (S-adenosylmethionine synthetase) | WO0100843 EP1108790 | AX063959 AX127148 |
| pck | Phosphoenol Pyruvate Carboxykinase (phosphoenol pyruvate carboxykinase) | WO0100844 | AJ269506 AX065053 |
| pgi | Glucose 6-Phosphate Isomerase EC 5.3.1.9 (glucose-6-phosphate isomerase) | EP1087015 EP1108790 | AX136015 AX127146 |
| poxB | Pyruvate Oxidase EC 1.2.3.3 (pyruvate oxidase) | WO0100844 EP1096013 | AX064959 AX137665 |
| zwa2 | Cell Growth Factor 2 (growth factor 2) | EP1106693 EP1108790 | AX113822 AX127146 |

A "copy of an open reading frame (ORF), gene or allele of threonine production" is to be understood as meaning all the open reading frames, genes or alleles of which enhancement/over-expression can have the effect of improving threonine production.

These include, inter alia, the following open reading frames, genes or alleles: accBC, accDA, cstA, cysD, cysE, cysH, cysI, cysN, cysQ, dps, eno, fda, gap, gap2, gdh, gnd, hom, hom$^{FBR}$, lysC, lysC$^{FBR}$, msiK, opcA, oxyR, ppc, ppc$^{FBR}$, pgk, pknA, pknB, pknD, pknG, ppsA, ptsH, ptsI, ptsM, pyc, pyc P458S, sigC, sigD, sigE, sigH, sigM, tal, thyA, tkt, tpi, thrB, thrC, thrE, zwa1, zwf and zwf A213T. These are summarized and explained in Table 6. These include, in particular, the lysC$^{FBR}$ alleles which code for a "feed back" resistant aspartate kinase (See Table 2) and the hom$^{FBR}$ alleles which code for a "feed back" resistant homoserine dehydrogenase.

The second, optionally third or fourth copy of the open reading frame (ORF), gene or allele of threonine production in question can be integrated at in each case a second, optionally third or fourth site. The following open reading frames, genes or nucleotide sequences, inter alia, can be used for this: ccpA1, ccpA2, citA, citB, citE, ddh, gluA, gluB, gluC, gluD, glyA, ilvA, ilvBN, ilvC, ilvD, luxR, luxS, lysR1, lysR2, lysR3, mdh, menE, metA, metD, pck, poxB, sigB and zwa2. These are summarized and explained in Table 7.

The sites mentioned include, of course, not only the coding regions of the open reading frames or genes mentioned, but also the regions or nucleotide sequences lying upstream which are responsible for expression and regulation, such as, for example, ribosome binding sites, promoters, binding sites for regulatory proteins, binding sites for regulatory ribonucleic acids and attenuators. These regions in general lie in a range of 1–800, 1–600, 1–400, 1–200, 1–100 or 1–50 nucleotides upstream of the coding region. In the same way, regions lying downstream, such as, for example, transcription terminators, are also included. These regions in general lie in a range of 1–400, 1–200, 1–100, 1–50 or 1–25 nucleotides downstream of the coding region.

Intergenic regions in the chromosome, that is to say nucleotide sequences without a coding function, can furthermore be used. Finally, prophages or defective phages contained in the chromosome can be used for this.

Examples of regions of the *Corynebacterium glutamicum* chromosome representing intergenic regions, prophages, defective phages or phage components are shown in tables 12 and 13. The positions of the DNA regions refer to the genome map of *Corynebacterium glutamicum* ATCC 13032 as presented in EP-A-1108790 or in the databank of the European Molecular Biologies Laboratories (EMBL, Heidelberg, Germany and Cambridge, UK).

TABLE 6

Open reading frames, genes and alleles of threonine production

| Name | Description of the coded enzyme or protein | Reference | Access Number |
|---|---|---|---|
| accBC | Acyl-CoA Carboxylase EC 6.3.4.14 (acyl-CoA carboxylase) | Jäger et al. Archives of Microbiology 166:76–82(1996) EP1108790 WO0100805 | U35023 AX123524 AX066441 |
| accDA | Acetyl-CoA Carboxylase EC 6.4.1.2 (acetyl-CoA carboxylase) | EP1055725 EP1108790 WO0100805 | AX121013 AX066443 |
| cstA | Carbon Starvation Protein A (carbon starvation protein A) | EP1108790 WO0100804 | AX120811 AX066109 |
| cysD | Sulfate Adenylyltransferase sub-unit II EC 2.7.7.4 (sulfate adenylyltransferase small chain) | EP1108790 | AX123177 |
| cysE | Serine Acetyltransferase EC 2.3.1.30 (serine acetyltransferase) | EP1108790 WO0100843 | AX122902 AX063961 |
| cysH | 3'-Phosphoadenyl Sulfate Reductase EC 1.8.99.4 (3'-phosphoadenosine 5'-phosphosulfate reductase) | EP1108790 WO0100842 | AX123178 AX066001 |
| cysK | Cysteine Synthase EC 4.2.99.8 (cysteine synthase) | EP1108790 WO0100843 | AX122901 AX063963 |
| cysN | Sulfate Adenylyltransferase sub-unit I EC 2.7.7.4 (sulfate adenylyltransferase) | EP1108790 | AX123176 AX127152 |
| cysQ | Transport protein CysQ (transporter cysQ) | EP1108790 WO0100805 | AX127145 AX066423 |
| dps | DNA Protection Protein (protection during starvation protein) | EP1108790 | AX127153 |
| eno | Enolase EC 4.2.1.11 (enolase) | EP1108790 WO0100844 EP1090998 Hermann et al., Electrophoresis 19:3217–3221 (1998) | AX127146 AX064945 AX136862 |
| fda | Fructose Bisphosphate Aldolase EC 4.1.2.13 (fructose bisphosphate aldolase) | van der Osten et al., Molecular Microbiology 3:1625–1637 (1989) | X17313 |
| gap | Glyceraldehyde 3-Phosphate Dehydrogenase EC 1.2.1.12 (glyceraldehyde 3-phosphate dehydrogenase) | EP1108790 WO0100844 Eikmanns et al., Journal of Bacteriology 174:6076–6086 (1992) | AX127148 AX064941 X59403 |
| gap2 | Glyceraldehyde 3-Phosphate Dehydrogenase EC 1.2.1.12 (glyceraldehyde 3-phosphate dehydrogenase 2) | EP1108790 WO0100844 | AX127146 AX064939 |
| gdh | Glutamate Dehydrogenase EC 1.4.1.4 (glutamate dehydrogenase) | EP1108790 WO0100844 Boermann et al., Molecular Microbiology 6:317–326 (1992) Guyonvarch et al., NCBI | AX127150 AX063811 X59404 X72855 |
| gnd | 6-Phosphogluconate Dehydrogenase EC 1.1.1.44 (6-phosphogluconate dehydrogenase) | EP1108790 WO0100844 | AX127147 AX121689 AX065125 |

TABLE 6-continued

Open reading frames, genes and alleles of threonine production

| Name | Description of the coded enzyme or protein | Reference | Access Number |
|---|---|---|---|
| hom | Homoserine Dehydrogenase<br>EC 1.1.1.3<br>(homoserine dehydrogenase) | Peoples et al., Molecular Microbiology 2:63–72 (1988) | Y00546 |
| hom$^{FBR}$ | Homoserine Dehydrogenase feedback resistant (fbr)<br>EC 1.1.1.3<br>(homoserine dehydrogenase fbr) | Reinscheid et al., Journal of Bacteriology 173:3228–30 (1991) | |
| lysC | Aspartate Kinase<br>EC 2.7.2.4<br>(aspartate kinase) | EP1108790<br>WO0100844<br>Kalinowski et al., Molecular Microbiology 5:1197–204 (1991) | AX120365<br>AX063743<br>X57226 |
| lysC$^{FBR}$ | Aspartate Kinase feedback resistent (fbr)<br>EC 2.7.2.4<br>(aspartate kinase fbr) | see Table 2 | |
| msiK | Sugar Importer<br>(multiple sugar import protein) | EP1108790 | AX120892 |
| opcA | Glucose 6-Phosphate Dehydrogenase<br>(subunit of glucose 6-phosphate dehydrogenase) | WO0104325 | AX076272 |
| oxyR | Transcription Regulator<br>(transcriptional regulator) | EP1108790 | AX122198<br>AX127149 |
| ppc$^{FBR}$ | Phosphoenol Pyruvate Carboxylase feedback resistent<br>EC 4.1.1.31<br>(phosphoenol pyruvate carboxylase feedback resistant) | EP0723011<br>WO0100852 | |
| ppc | Phosphoenol Pyruvate Carboxylase<br>EC 4.1.1.31<br>(phosphoenol pyruvate carboxylase) | EP1108790<br>O'Reagan et al., Gene 77(2):237–251 (1989) | AX127148<br>AX123554<br>M25819 |
| pgk | Phosphoglycerate Kinase<br>EC 2.7.2.3<br>(phosphoglycerate kinase) | EP1108790<br>WO0100844<br>Eikmanns, Journal of Bacteriology 174:6076–6086 (1992) | AX121838<br>AX127148<br>AX064943<br>X59403 |
| pknA | Protein Kinase A<br>(protein kinase A) | EP1108790 | AX120131<br>AX120085 |
| pknB | Protein Kinase B<br>(protein kinase B) | EP1108790 | AX120130<br>AX120085 |
| pknD | Protein Kinase D<br>(protein kinase D) | EP1108790 | AX127150<br>AX122469<br>AX122468 |
| pknG | Protein Kinase G<br>(protein kinase G) | EP1108790 | AX127152<br>AX123109 |
| ppsA | Phosphoenol Pyruvate Synthase<br>EC 2.7.9.2<br>(phosphoenol pyruvate synthase) | EP1108790 | AX127144<br>AX120700<br>AX122469 |
| ptsH | Phosphotransferase System Protein H<br>EC 2.7.1.69<br>(phosphotransferase system component H) | EP1108790<br>WO0100844 | AX122210<br>AX127149<br>AX069154 |
| ptsI | Phosphotransferase System Enzyme I<br>EC 2.7.3.9<br>(phosphotransferase system enzyme I) | EP1108790 | AX122206<br>AX127149 |
| ptsM | Glucose-specific Phosphotransferase System Enzyme II<br>EC 2.7.1.69<br>(glucose phosphotransferase-system enzyme II) | Lee et al., FEMS Microbiology Letters 119 (1–2):137–145 (1994) | L18874 |

TABLE 6-continued

Open reading frames, genes and alleles of threonine production

| Name | Description of the coded enzyme or protein | Reference | Access Number |
|---|---|---|---|
| pyc | Pyruvate Carboxylase EC 6.4.1.1 (pyruvate carboxylase) | WO9918228 Peters-Wendisch et al., Microbiology 144:915–927 (1998) | A97276 Y09548 |
| pyc P458S | Pyruvate Carboxylase EC 6.4.1.1 (pyruvate carboxylase) amino acid exchange P458S | EP1108790 | |
| sigC | Sigma Factor C EC 2.7.7.6 (extracytoplasmic function alternative sigma factor C) | EP1108790 | AX120368 AX120085 |
| sigD | RNA Polymerase Sigma Factor D EC 2.7.7.6 (RNA polymerase sigma factor) | EP1108790 | AX120753 AX127144 |
| sigE | Sigma Factor E EC 2.7.7.6 (extracytoplasmic function alternative sigma factor E) | EP1108790 | AX127146 AX121325 |
| sigH | Sigma Factor H EC 2.7.7.6 (sigma factor SigH) | EP1108790 | AX127145 AX120939 |
| sigM | Sigma Factor M EC 2.7.7.6 (sigma factor SigM) | EP1108790 | AX123500 AX127153 |
| tal | Transaldolase EC 2.2.1.2 (transaldolase) | WO0104325 | AX076272 |
| thrB | Homoserine Kinase EC 2.7.1.39 (homoserine kinase) | Peoples et al., Molecular Microbiology 2:63–72 (1988) | Y00546 |
| thrC | Threonine Synthase EC 4.2.99.2 (threonine synthase) | Han et al., Molecular Microbiology 4:1693–1702 (1990) | X56037 |
| thrE | Threonine Exporter (threonine export carrier) | EP1085091 | AX137526 |
| thyA | Thymidylate Synthase EC 2.1.1.45 (thymidylate synthase) | EP1108790 | AX121026 AX127145 |
| tkt | Transketolase EC 2.2.1.1 (transketolase) | Ikeda et al., NCBI | AB023377 |
| tpi | Triose phosphate Isomerase EC 5.3.1.1 (triose phosphate isomerase) | Eikmanns, Journal of Bacteriology 174:6076–6086 (1992) | X59403 |
| zwa1 | Cell Growth Factor 1 (growth factor 1) | EP1111062 | AX133781 |
| zwf | Glucose 6-Phosphate 1-Dehydrogenase EC 1.1.1.49 (glucose 6-phosphate 1-dehydrogenase) | EP1108790 WO0104325 | AX127148 AX121827 AX076272 |
| zwf A213T | Glucose 6-Phosphate 1-Dehydrogenase EC 1.1.1.49 (glucose 6-phosphate 1-dehydrogenase) amino acid exchange A213T | EP1108790 | |

TABLE 7

Target sites for integration of open reading frames, genes and alleles of threonine production

| Gene name | Description of the coded enzyme or protein | Reference | Access Number |
|---|---|---|---|
| ccpA1 | Catabolite Control Protein (catabolite control protein A1) | WO0100844 EP1108790 | AX065267 AX127147 |
| ccpA2 | Catabolite Control Protein (catabolite control protein A2) | WO0100844 EP1108790 | AX065267 AX121594 |
| citA | Sensor Kinase CitA (sensor kinase CitA) | EP1108790 | AX120161 |
| citB | Transcription Regulator CitB (transcription regulator CitB) | EP1108790 | AX120163 |
| citE | Citrate Lyase EC 4.1.3.6 (citrate lyase) | WO0100844 EP1108790 | AX065421 AX127146 |
| ddh | Diaminopimelate Dehydrogenase EC 1.4.1.16 (diaminopimelate dehydrogenase) | Ishino et al., Nucleic Acids Research 15:3917 (1987) EP1108790 | S07384 AX127152 |
| gluA | Glutamate Transport ATP-binding Protein (glutamate transport ATP-binding protein) | Kronemeyer et al., Journal of Bacteriology 177(5):1152–8 (1995) | X81191 |
| gluB | Glutamate-binding Protein (glutamate-binding protein) | Kronemeyer et al., Journal of Bacteriology 177(5):1152–8 (1995) | X81191 |
| gluC | Glutamate Transport Permease (glutamate transport system permease) | Kronemeyer et al., Journal of Bacteriology 177(5):1152–8 (1995) | X81191 |
| gluD | Glutamate Transport Permease (glutamate transport system permease) | Kronemeyer et al., Journal of Bacteriology 177(5):1152–8 (1995) | X81191 |
| glyA | Glycine Hydroxymethyltransferase EC 2.1.2.1 (glycine hydroxymethyltransferase) | WO0100843 | AX063861 AF327063 |
| ilvA | Threonine Dehydratase EC 4.2.1.16 (threonine dehydratase) | Möckel et al., Journal of Bacteriology 174 (24), 8065–8072 (1992) EP1108790 | A47044 L01508 AX127150 |
| ilvBN | Acetolactate Synthase EC 4.1.3.18 (acetolactate synthase) | Keilhauer et al., Journal of Bacteriology 175(17):5595–603 (1993) EP1108790 | L09232 AX127147 |
| ilvC | Reductoisomerase EC 1.1.1.86 (ketol-acid reductoisomerase) | Keilhauer et al., Journal of Bacteriology 175(17):5595–603 (1993) EP1108790 | C48648 AX127147 |
| ilvD | Dihydroxy-acid Dehydratase EC 4.2.1.9 (dihydroxy-acid dehydratase) | EP1006189 | AX136925 |
| luxR | Transcription Regulator LuxR (transcription regulator LuxR) | WO0100842 EP1108790 | AX065953 AX123320 |
| luxS | Histidine Kinase LuxS (histidine kinase LuXS) | EP1108790 | AX123323 AX127153 |
| lysR1 | Transcription Regulator LysR1 (transcription regulator LysR1) | EP1108790 | AX064673 AX127144 |
| lysR2 | Transcription Activator LysR2 (transcription regulator LysR2) | EP1108790 | AX123312 |
| lysR3 | Transcription Regulator LysR3 (transcription regulator LysR3) | WO0100842 EP1108790 | AX065957 AX127150 |
| mdh | Malate Dehydrogenase EC 1.1.1.37 (malate dehydrogenase) | WO0100844 | AX064895 |
| menE | O-Succinylbenzoic Acid CoA Ligase EC 6.2.1.26 (O-succinylbenzoate CoA ligase) | WO0100843 EP1108790 | AX064599 AX064193 AX127144 |
| metA | Homoserine O-Acetyltransferase EC 2.3.1.31 (homoserine O-acetyltransferase) | Park et al., Molecular Cells 30;8(3):286–94 (1998) WO0100843 EP1108790 | AX063895 AX127145 |
| metD | Transcription Regulator MetD (transcription regulator MetD) | EP1108790 | AX123327 AX127153 |
| pck | Phosphoenol Pyruvate Carboxykinase (phosphoenol pyruvate carboxykinase) | WO0100844 | AJ269506 AX065053 |
| poxB | Pyruvate Oxidase EC 1.2.3.3 (pyruvate oxidase) | WO0100844 EP1096013 | AX064959 AX137665 |
| sigB | RNA Polymerase Transcription Factor (RNA polymerase transcription factor) | EP1108790 | AX127149 |
| zwa2 | Cell Growth Factor 2 (growth factor 2) | EP1106693 EP1108790 | AX113822 AX127146 |

The invention accordingly also provides a process for the production of coryneform bacteria which produce L-methionine and/or L-threonine, which comprises a) isolating the nucleotide sequence of at least one desired ORF, gene or allele of methionine production or threonine production, optionally including the expression and/or regulation signals, b) providing the 5' and the 3' end of the ORF, gene or allele with nucleotide sequences of the target site, c) preferably incorporating the nucleotide sequence of the desired ORF, gene or allele provided with nucleotide sequences of the target site into a vector which does not replicate or replicates to only a limited extent in coryneform bacteria, d) transferring the nucleotide sequence according to b) or c) into coryneform bacteria, and e) isolating coryneform bacteria in which the nucleotide sequence according to a) is incorporated at the target site, no nucleotide sequence which is capable of/enables episomal replication in microorganisms, no nucleotide sequence which is capable of/enables transposition and no nucleotide sequence which imparts resistance to antibiotics remaining at the target site.

The invention furthermore provides coryneform bacteria, in particular of the genus *Corynebacterium*, which produce L-valine, wherein these have, in addition to at least one of the copy of an open reading frame (ORF), gene or allele of valine production present at the natural site (locus), in each case a second, optionally third or fourth copy of the open reading frame (ORF), gene or allele in question at in each case a second, optionally third or fourth site in integrated form, no nucleotide sequence which is capable of/enables episomal replication in microorganisms, no nucleotide sequence which is capable of/enables transposition and no nucleotide sequence which imparts resistance to antibiotics being present at the particular second, optionally third or fourth site.

The invention also furthermore provides a process for the preparation of L-valine, which comprises the following steps:
a) fermentation of coryneform bacteria, in particular *Corynebacterium glutamicum*, characterized in that these have, in addition to at least one of the copy of an open reading frame (ORF), gene or allele of valine production present at the natural site (locus), in each case a second, optionally third or fourth copy of the open reading frame (ORF), gene or allele in question at in each case a second, optionally third or fourth site in integrated form, no nucleotide sequence which is capable of/enables episomal replication in microorganisms, no nucleotide sequence which is capable of/enables transposition and no nucleotide sequence which imparts resistance to antibiotics being present at the particular second, optionally third or fourth site,
under conditions which allow expression of the said open reading frames (ORF), genes or alleles,
b) concentration of the L-valine in the fermentation broth,
c) isolation of the L-valine from the fermentation broth, optionally
d) with constituents from the fermentation broth and/or the biomass to the extent of > (greater than) 0 to 100%.

A "copy of an open reading frame (ORF), gene or allele of valine production" is to be understood as meaning all the open reading frames, genes or alleles of which enhancement/over-expression can have the effect of improving valine production.

These include, inter alia, the following open reading frames, genes or alleles: brnE, brnF, brnEF, cstA, cysD, dps, eno, fda, gap, gap2, gdh, ilvB, ilvN, ilvBN, ilvC, ilvD, ilvE msiK, pgk, ptsH, ptsI, ptsM, sigC, sigD, sigE, sigH, sigM, tpi, zwa1. These are summarized and explained in Table 8. These include in particular the ilvBN alleles which code for a valine-resistant acetolactate synthase.

The second, optionally third or fourth copy of the open reading frame (ORF), gene or allele of valine production in question can be integrated at in each case a second, optionally third or fourth site. The following open reading frames, genes or nucleotide sequences, inter alia, can be used for this: aecD, ccpA1, ccpA2, citA, citB, citE, ddh, gluA, gluB, gluC, gluD, glyA, ilvA, luxR, lysR1, lysR2, lysR3, panB, panC, poxB and zwa2. These are summarized and explained in Table 9.

The sites mentioned include, of course, not only the coding regions of the open reading frames or genes mentioned, but also the regions or nucleotide sequences lying upstream which are responsible for expression and regulation, such as, for example, ribosome binding sites, promoters, binding sites for regulatory proteins, binding sites for regulatory ribonucleic acids and attenuators. These regions in general lie in a range of 1–800, 1–600, 1–400, 1–200, 1–100 or 1–50 nucleotides upstream of the coding region. In the same way, regions lying downstream, such as, for example, transcription terminators, are also included. These regions in general lie in a range of 1–400, 1–200, 1–100, 1–50 or 1–25 nucleotides downstream of the coding region.

Intergenic regions in the chromosome, that is to say nucleotide sequences without a coding function, can furthermore be used. Finally, prophages or defective phages contained in the chromosome can be used for this.

Examples of regions of the *Corynebacterium glutamicum* chromosome representing intergenic regions, prophages, defective phages or phage components are shown in tables 12 and 13. The positions of the DNA regions refer to the genome map of *Corynebacterium glutamicum* ATCC 13032 as presented in EP-A-1108790 or in the databank of the European Molecular Biologies Laboratories (EMBL, Heidelberg, Germany and Cambridge, UK).

TABLE 8

Open reading frames, genes and alleles of valine production

| Name | Description of the coded enzyme or protein | Reference | Access Number |
|---|---|---|---|
| brnEF | Export of branched-chain amino acids | EP1096010 | |
| | (branched chain amino acid export) | Kennerknecht et al., NCBI | AF454053 |
| cstA | Carbon Starvation Protein A | EP1108790 | AX120811 |
| | (carbon starvation protein A) | WO0100804 | AX066109 |
| dps | DNA Protection Protein (protection during starvation protein) | EP1108790 | AX127153 |
| eno | Enolase | EP1108790 | AX127146 |
| | EC 4.2.1.11 | WO0100844 | AX064945 |
| | (enolase) | EP1090998 | AX136862 |
| | | Hermann et al., Electrophoresis 19:3217–3221 (1998) | |
| fda | Fructose Bisphosphate Aldolase | van der Osten et | X17313 |

TABLE 8-continued

Open reading frames, genes and alleles of valine production

| Name | Description of the coded enzyme or protein | Reference | Access Number |
|---|---|---|---|
| | EC 4.1.2.13 (fructose bisphosphate aldolase) | al., Molecular Microbiology 3:1625–1637 (1989) | |
| gap | Glyceraldehyde 3-Phosphate Dehydrogenase EC 1.2.1.12 (glyceraldehyde 3-phosphate dehydrogenase) | EP1108790 WO0100844 Eikmanns et al., Journal of Bacteriology 174:6076–6086 (1992) | AX127148 AX064941 X59403 |
| gap2 | Glyceraldehyde 3-Phosphate Dehydrogenase EC 1.2.1.12 (glyceraldehyde 3-phosphate dehydrogenase 2) | EP1108790 WO0100844 | AX127146 AX064939 |
| gdh | Glutamate Dehydrogenase EC 1.4.1.4 (glutamate dehydrogenase) | EP1108790 WO0100844 Boermann et al., Molecular Microbiology 6:317–326 (1992); Guyonvarch et al., NCBI | AX127150 AX063811 X59404 X72855 |
| ilvBN | Acetolactate Synthase EC 4.1.3.18 (acetolactate synthase) | Keilhauer et al., Journal of Bacteriology 175(17):5595–603 (1993) EP1108790 | L09232 AX127147 |
| ilvC | Isomeroreductase EC 1.1.1.86 (acetohydroxy acid isomeroreductase) | Keilhauer et al., Journal of Bacteriology 175(17):5595–603 (1993) EP1108790 | C48648 AX127147 |
| ilvD | Dihydroxy-acid Dehydratase EC 4.2.1.9 (dihydroxy acid dehydratase) | EP1006189 | AX136925 |
| ilvE | Transaminase B EC 2.6.1.42 (transaminase B) | EP1108790 | AX127150 AX122498 |
| msiK | Sugar Importer (multiple sugar import protein) | EP1108790 | AX120892 |
| pgk | Phosphoglycerate Kinase EC 2.7.2.3 (phosphoglycerate kinase) | EP1108790 WO0100844 Eikmanns, Journal of Bacteriology 174:6076–6086 (1992) | AX121838 AX127148 AX064943 X59403 |
| ptsH | Phosphotransferase System Protein H EC 2.7.1.69 (phosphotransferase system component H) | EP1108790 WO0100844 | AX122210 AX127149 AX069154 |
| ptsI | Phosphotransferase System Enzyme I EC 2.7.3.9 (phosphotransferase system enzyme I) | EP1108790 | AX122206 AX127149 |
| ptsM | Glucose-specific Phosphotransferase System Enzyme II EC 2.7.1.69 (glucose phosphotransferase-system enzyme II) | Lee et al., FEMS Microbiology Letters 119 (1–2):137–145 (1994) | L18874 |
| sigC | Sigma Factor C EC 2.7.7.6 (extracytoplasmic function alternative sigma factor C) | EP1108790 | AX120368 AX120085 |
| sigD | RNA Polymerase Sigma Factor D EC 2.7.7.6 (RNA polymerase sigma factor) | EP1108790 | AX120753 AX127144 |
| sigE | Sigma Factor E | EP1108790 | AX127146 |

TABLE 8-continued

Open reading frames, genes and alleles of valine production

| Name | Description of the coded enzyme or protein | Reference | Access Number |
|---|---|---|---|
| | EC 2.7.7.6 (extracytoplasmic function alternative sigma factor E) | | AX121325 |
| sigH | Sigma Factor H EC 2.7.7.6 (sigma factor SigH) | EP1108790 | AX127145 AX120939 |
| sigM | Sigma Factor M EC 2.7.7.6 (sigma factor SigM) | EP1108790 | AX123500 AX127153 |
| tpi | Triose Phosphate Isomerase EC 5.3.1.1 (triose phosphate isomerase) | Eikmanns, Journal of Bacteriology 174:6076–6086 (1992) | X59403 |
| zwa1 | Cell Growth Factor 1 (growth factor 1) | EP1111062 | AX133781 |

TABLE 9

Target sites for integration of open reading frames, genes and alleles of valine production

| Gene name | Description of the coded enzyme or protein | Reference | Access Number |
|---|---|---|---|
| aecD | beta C-S Lyase EC 2.6.1.1 (beta C-S lyase) | Rossol et al., Journal of Bacteriology 174(9):2968–77 (1992) | M89931 |
| ccpA1 | Catabolite Control Protein (catabolite control protein A1) | WO0100844 EP1108790 | AX065267 AX127147 |
| ccpA2 | Catabolite Control Protein (catabolite control protein A2) | WO0100844 EP1108790 | AX065267 AX121594 |
| citA | Sensor Kinase CitA (sensor kinase CitA) | EP1108790 | AX120161 |
| citB | Transcription Regulator CitB (transcription regulator CitB) | EP1108790 | AX120163 |
| citE | Citrate Lyase EC 4.1.3.6 (citrate lyase) | WO0100844 EP1108790 | AX065421 AX127146 |
| ddh | Diaminopimelate Dehydrogenase EC 1.4.1.16 (diaminopimelate dehydrogenase) | Ishino et al., Nucleic Acids Research 15:3917 (1987) EP1108790 | S07384 AX127152 |
| gluA | Glutamate Transport ATP-binding Protein (glutamate transport ATP-binding protein) | Kronemeyer et al., Journal of Bacteriology 177(5):1152–8 (1995) | X81191 |
| gluB | Glutamate-binding Protein (glutamate-binding protein) | Kronemeyer et al., Journal of Bacteriology 177(5):1152–8 (1995) | X81191 |
| gluC | Glutamate Transport Permease (glutamate transport system permease) | Kronemeyer et al., Journal of Bacteriology 177(5):1152–8 (1995) | X81191 |
| gluD | Glutamate Transport Permease (glutamate transport system permease) | Kronemeyer et al., Journal of Bacteriology 177(5):1152–8 (1995) | X81191 |
| glyA | Glycine Hydroxymethyltransferase EC 2.1.2.1 (glycine hydroxymethyltransferase) | WO0100843 | AX063861 AF327063 |
| ilvA | Threonine Dehydratase EC 42.1.16 (threonine dehydratase) | Möckel et al., Journal of Bacteriology 174 (24), 8065–8072 (1992) EP1108790 | A47044 L01508 AX127150 |
| luxR | Transcription Regulator LuxR (transcription regulator LuxR) | WO0100842 EP1108790 | AX065953 AX123320 |
| lysR1 | Transcription Regulator LysR1 (transcription regulator LysR1) | EP1108790 | AX064673 AX127144 |
| lysR2 | Transcription Activator LysR2 (transcription regulator LysR2) | EP1108790 | AX123312 |
| lysR3 | Transcription Regulator LysR3 (transcription regulator LysR3) | WO0100842 EP1108790 | AX065957 AX127150 |
| panB | Ketopantoate Hydroxymethyltransferase EC 2.1.2.11 (ketopantoate hydroxymethyltransferase) | US6177264 | X96580 |
| panC | Pantothenate Synthetase EC 6.3.2.1 (pantothenate synthetase) | US6177264 | X96580 |
| poxB | Pyruvate Oxidase EC 1.2.3.3 (pyruvate oxidase) | WO0100844 EP1096013 | AX064959 AX137665 |
| zwa2 | Cell Growth Factor 2 (growth factor 2) | EP1106693 EP1108790 | AX113822 AX127146 |

The invention accordingly also provides a process for the production of coryneform bacteria which produce L-valine, which comprises
a) isolating the nucleotide sequence of at least one desired ORF, gene or allele of valine production, optionally including the expression and/or regulation signals,
b) providing the 5' and the 3' end of the ORF, gene or allele with nucleotide sequences of the target site,
c) preferably incorporating the nucleotide sequence of the desired ORF, gene or allele provided with nucleotide sequences of the target site into a vector which does not replicate or replicates to only a limited extent in coryneform bacteria,
d) transferring the nucleotide sequence according to b) or c) into coryneform bacteria, and
e) isolating coryneform bacteria in which the nucleotide sequence according to a) is incorporated at the target site, no nucleotide sequence which is capable of/enables episomal replication in microorganisms, no nucleotide sequence which is capable of/enables transposition and no nucleotide sequence which imparts resistance to antibiotics remaining at the target site.

The invention also furthermore provides a process for the preparation of L-tryptophane, which comprises the following steps:
a) fermentation of coryneform bacteria, in particular *Corynebacterium glutamicum*, characterized in that these have, in addition to at least one of the copy of an open reading frame (ORF), gene or allele of tryptophane production present at the natural site (locus), in each case a second, optionally third or fourth copy of the open reading frame (ORF), gene or allele in question at in each case a second, optionally third or fourth site in integrated form, no nucleotide sequence which is capable of/enables episomal replication in microorganisms, no nucleotide sequence which is capable of/enables transposition and no nucleotide sequence which imparts resistance to antibiotics being present at the particular second, optionally third or fourth site,
under conditions which allow expression of the said open reading frames (ORF), genes or alleles,
b) concentration of the tryptophane in the fermentation broth,
c) isolation of the tryptophane from the fermentation broth, optionally
d) with constituents from the fermentation broth and/or the biomass to the extent of > (greater than) 0 to 100%.

A "copy of an open reading frame (ORF), gene or allele of tryptophane production" is to be understood as meaning all the open reading frames, genes or alleles of which enhancement/over-expression can have the effect of improving tryptophane production.

These include, inter alia, the following open reading frames, genes or alleles: aroA, aroB, aroC, aroD, aroE, aroG, aroK, cstA, eno, gap, gap2, gnd, ppsA, rpe, serA, serB, serC, tal, thyA, tkt, tpi, trpA, trpB, trpC, trpD optionally comprising at least one of the amino acid exchanges selected from the group consisting of A215T (exchange of alanine at position 215 against threonine), D138A (exchange of aspartic acid at position 138 against alanine), S149F (exchange of serine at position 149 against phenylalanine) and A162E (exchange of alanine at position 162 against glutamic acid), trpE, trpE$^{FBR}$ comprising e.g. the amino acid exchange S38R (exchange of serine at position 38 against arginine), trpG, trpL optionally comprising the mutation W14*, zwa1, zwf optionally comprising the amino acid exchange A213T (exchange of alanine at position 213 against threonine). These are summarized and explained in Table 10. These include in particular the tryptophane operon comprising trpE, trpG, trpD, trpC and trpA and optionally trpL. Furthermore these include in particular a trpE$^{FBR}$ allele which codes for a tryptophane-resistant anthranilate synthase.

The second, optionally third or fourth copy of the open reading frame (ORF), gene or allele of tryptophane production in question can be integrated at in each case a second, optionally third or fourth site. The following open reading frames, genes or nucleotide sequences, inter alia, can be used for this: ccpA1, ccpA2, citA, citB, citE, cysE, gluA, gluB, gluC, gluD, glyA, luxR, luxS, lysR1, lysR2, lysR3, menE, pgi, pheA, poxB and zwa2. These are summarized and explained in Table 11.

The sites mentioned include, of course, not only the coding regions of the open reading frames or genes mentioned, but also the regions or nucleotide sequences lying upstream which are responsible for expression and regulation, such as, for example, ribosome binding sites, promoters, binding sites for regulatory proteins, binding sites for regulatory ribonucleic acids and attenuators. These regions in general lie in a range of 1–800, 1–600, 1–400, 1–200, 1–100 or 1–50 nucleotides upstream of the coding region. In the same way, regions lying downstream, such as, for example, transcription terminators, are also included. These regions in general lie in a range of 1–400, 1–200, 1–100, 1–50 or 1–25 nucleotides downstream of the coding region.

Intergenic regions in the chromosome, that is to say nucleotide sequences without a coding function, can furthermore be used. Finally, prophages or defective phages contained in the chromosome can be used for this.

Examples of regions of the *Corynebacterium glutamicum* chromosome representing intergenic regions, prophages, defective phages or phage components are shown in tables 12 and 13. The positions of the DNA regions refer to the genome map of *Corynebacterium glutamicum* ATCC 13032 as presented in EP-A-1108790 or in the databank of the European Molecular Biologies Laboratories (EMBL, Heidelberg, Germany and Cambridge, UK).

TABLE 10

Open reading frames, genes and alleles of tryptophane production

| Gene name | Description of the coded enzyme or protein | Reference | Access-Number |
| --- | --- | --- | --- |
| aroA | Enolpyruvylshikimate Phosphate Synthase EC 2.5.1.19 | O'Donohue et al., NCBI | AF114233 |

TABLE 10-continued

Open reading frames, genes and alleles of tryptophane production

| Gene name | Description of the coded enzyme or protein | Reference | Access-Number |
|---|---|---|---|
| | (enolpyruvylshikimate 3-phosphate synthase) | | |
| aroB | Dehydroquinate Synthetase EC 4.6.1.3 (dehydroquinate synthetase) | Burke et al., NCBI | AF124600 |
| aroC | Chorismate Synthase EC 4.6.1.4 (chorismate synthase) | Burke et al., NCBI | AF124600 |
| aroD | Dehydroquinate Dehydratase EC 4.2.1.10 (dehydroquinate dehydratase) | Joy et al., NCBI | AF124518 |
| aroE | Shikimate Dehydrogenase EC 1.1.1.25 (shikimate dehydrogenase) | Joy et al., NCBI | AF124518 |
| aroG | Dehydro-3-Deoxyphosphoheptonate Aldolase EC4.1.2.15 (dehydro-3-deoxyphosphoheptonate aldolase) | Chen et al., FEMS Microbioliology Letters 107:223–230(1993). | L07603 |
| aroK | Shikimate Kinase EC 2.7.1.71 (shikimate kinase) | Burke et al., NCBI | AF124600 |
| cstA | Carbon Starvation Protein A (carbon starvation protein A) | EP1108790 WO0100804 | AX120811 AX066109 |
| eno | Enolase EC 4.2.1.11 (enolase) | EP1108790 WO0100844 EP1090998 Hermann et al., Electrophoresis 19:3217–3221 (1998) | AX127146 AX064945 AX136862 |
| gap | Glyceraldehyde-3-Phosphate Dehydrogenase EC 1.2.1.12 (glyceraldehyde-3-phosphate dehydrogenase) | EP1108790 WO0100844 Eikmanns et al., Journal of Bacteriology 174:6076–6086 (1992) | AX127148 AX064941 X59403 |
| gap2 | Glyceraldehyde-3-Phosphate Dehydrogenase EC 1.2.1.12 (glyceraldehyde-3-phosphate dehydrogenase 2) | EP1108790 WO0100844 | AX127146 AX064939 |
| gnd | 6-Phosphogluconate Dehydrogenase EC 1.1.1.44 (6-phosphogluconate dehydrogenase) | EP1108790 WO0100844 | AX127147 AX121689 AX065125 |
| ppsA | Phosphoenolpyruvate Synthetase Ec 2.7.9.2 (phosphoenolpyruvate-synthase) | EP1108790 | AX127144 AX120700 |
| rpe | Ribulose-Phosphate Epimerase EC 5.1.3.1 (ribulose-phosphate-epimerase) | EP1108790 | AX127148 AX121852 |
| serA | Phosphoglycerate Dehydrogenase EC1.1.1.95 (phosphoglycerate-dehydrogenase) | EP1108790 | AX127147 AX121499 |
| serB | Phosphoserine Phosphatase EC 3.1.3.3 (phosphoserine phosphatase) | EP1108790 | AX127144 AX120551 |
| serC | Phosphoserine Aminotransferase EC 2.6.1.52 (phosphoserine aminotransferase) | EP1108790 | AX127145 AX121012 |
| tal | Transaldolase EC 2.2.1.2 (transaldolase) | WO0104325 | AX076272 |
| thyA | Thymidylate Synthase EC 2.1.1.45 (thymidylate synthase) | EP1108790 | AX121026 AX127145 |
| tkt | Transketolase EC 2.2.1.1 (transketolase) | Ikeda et al., NCBI | AB023377 |
| tpi | Triose-phosphate Isomerase EC 5.3.1.1 | Eikmanns, Journal of | X59403 |

TABLE 10-continued

Open reading frames, genes and alleles of tryptophane production

| Gene name | Description of the coded enzyme or protein | Reference | Access-Number |
|---|---|---|---|
| | (triose-phosphate isomerase) | Bacteriology 174:6076–6086 (1992) | |
| trpA | Tryptophane Synthase (alpha Kette) EC 4.2.1.20 (tryptophan synthase (alpha chain)) | Matsui et al., Nucleic Acids Research 14:10113–10114 (1986) | X04960 |
| trpB | Tryptophane Synthase (beta Kette) EC 4.2.1.20 (tryptophan synthase (beta chain)) | Matsui et al., Nucleic Acids Research 14:10113–10114 (1986) | X04960 |
| trpC | Phosphoribosylanthranilate Isomerase EC 5.3.1.24 (phosphoribosylanthranilate isomerase) | Matsui et al., Nucleic Acids Research 14:10113–10114 (1986) | X04960 |
| trpD | Anthranilate Phosphoribosyltransferase EC 2.4.2.18 (anthranilate phosphoribosyltransferase) | Matsui et al., Nucleic Acids Research 14:10113–10114 (1986) | X04960 |
| trpD A125T, D138A, S149F, A162E | Anthranilate Phosphoribosyltransferase EC 2.4.2.18 anthranilate (phosphoribosyltransferase) amino acid exchanges A125T, D138A, S149F, A162E | O'Gara et al., Applied and Environmental Microbiology 61:4477–4479 (1995) | |
| trpE | Anthranilate Synthase Komponente I EC 4.1.3.27 (anthranilate synthase component I) | Matsui et al., Nucleic Acids Research 14:10113–10114 (1986) | X04960 |
| trpE fbr | Anthranilat Synthase Component I feedback resistent EC 4.1.3.27 (anthranilate synthase component I feedback resistant) | Matsui et al., Journal of Bacteriology 169:5330–5332 (1987) | |
| trpG | Anthranilate Synthase Komponente II EC 4.1.3.24 (anthranilate synthase component II) | Matsui et al., Nucleic Acids Research 14:10113–10114 (1986) | X04960 |
| trpL | Trp Operon Leader Peptide (trp operon leader peptide) | Matsui et al., Nucleic Acids Research 14:10113–10114 (1986) | X04960 |
| trpL W14* | Trp Operon Leaderpeptid (trp operon leader peptide mutation W14*) | Herry et al., Applied and Environmental Microbiology 59:791–799 (1993) | |
| zwa1 | Cell Growth Factor 1 (growth factor 1) | EP1111062 | AX133781 |
| zwf | Glucose-6-phosphat1-1-Dehydrogenase EC 1.1.1.49 (glucose-6-phosphate-1-dehydrogenase) | EP1108790 WO0104325 | AX127148 AX121827 AX076272 |
| zwf A213T | Glucose-6-phosphate-1-Dehydrogenase EC 1.1.1.49 (glucose-6-phosphate-1-dehydrogenase) amino acid exchange A213T | EP1108790 | |

TABLE 11

Target sites for integration of open reading frames, genes and alleles of tryptophane production

| Gene name | Description of the coded enzyme or protein | Reference | Access Number |
|---|---|---|---|
| ccpA1 | Catabolite Control Protein (catabolite control protein A1) | WO0100844 EP1108790 | AX065267 AX127147 |
| ccpA2 | Catabolite Control Protein (catabolite control protein A2) | WO0100844 EP1108790 | AX065267 AX121594 |
| citA | Sensor-Kinase CitA (sensor kinase CitA) | EP1108790 | AX120161 |
| citB | Transcription Regulator CitB (transcription regulator CitB) | EP1108790 | AX120163 |
| citE | Citrate-Lyase EC 4.1.3.6 (citrate lyase) | WO0100844 EP1108790 | AX065421 AX127146 |
| cysE | Serine O-Acetyltransferase EC 2.3.1.30 (serine O-acetyltransferase) | EP1108790 | AX122902 |
| gluA | Glutamate Transport ATP-binding Protein (glutamate transport ATP-binding protein) | Kronemeyer et al., Journal of Bacteriology 177(5):1152–8 (1995) | X81191 |
| gluB | Glutamate-binding Protein (glutamate binding protein) | Kronemeyer et al., Journal of Bacteriology 177(5):1152–8 (1995) | X81191 |
| gluC | Glutamate Transport Permease (glutamate transport system permease) | Kronemeyer et al., Journal of Bacteriology 177(5):1152–8 (1995) | X81191 |
| gluD | Glutamate Transport Permease (glutamate transport system permease) | Kronemeyer et al., Journal of Bacteriology 177(5):1152–8 (1995) | X81191 |
| glyA | glycine hydroxymethyltransferase EC 2.1.2.1 (glycine hydroxymethyltransferase) | JP1997028391 | E12594 |
| luxR | Transkription Regulator LuxR (transcription regulator LuxR) | WO0100842 EP1108790 | AX065953 AX123320 |
| luxS | Histidine Kinase LuxS (histidine kinase LuxS) | EP1108790 | AX123323 AX127153 |
| lysR1 | Transkription Regulator LysR1 (transcription regulator LysR1) | EP1108790 | AX064673 AX127144 |
| lysR2 | Transkription Activator LysR2 (transcription regulator LysR2) | EP1108790 | AX123312 |
| lysR3 | Transkription Regulator LysR3 (transcription regulator LysR3) | WO0100842 EP1108790 | AX065957 AX127150 |
| menE | O-Succinylbenzoic acid-CoA-Ligase EC 6.2.1.26 (O-succinylbenzoate-CoA ligase) | WO0100843 EP1108790 | AX064599 AX064193 AX127144 |
| pgi | Glucose-6-Phosphate-Isomerase EC 5.3.1.9 (glucose-6-phosphate isomerase) | EP1087015 EP1108790 | AX136015 AX127146 |
| pheA | Prephenate Dehydratase EC 4.2.1.51 (prephenate dehydratase) | Follettie et al., Journal of Bacteriology 167:695–702 (1986) | M13774 |
| poxB | Pyruvate-Oxidase EC 1.2.3.3 (pyruvate oxidase) | WO0100844 EP1096013 | AX064959 AX137665 |
| zwa2 | Cell Growth Factor 2 (growth factor 2) | EP1106693 EP1108790 | AX113822 AX127146 |

The invention accordingly also provides a process for the production of coryneform bacteria which produce L-valine, which comprises a) isolating the nucleotide sequence of at least one desired ORF, gene or allele of valine production, optionally including the expression and/or regulation signals, b) providing the 5' and the 3' end of the ORF, gene or allele with nucleotide sequences of the target site, c) preferably incorporating the nucleotide sequence of the desired ORF, gene or allele provided with nucleotide sequences of the target site into a vector which does not replicate or replicates to only a limited extent in coryneform bacteria, d) transferring the nucleotide sequence according to b) or c) into coryneform bacteria, and e) isolating coryneform bacteria in which the nucleotide sequence according to a) is incorporated at the target site, no nucleotide sequence which is capable of/enables episomal replication in microorganisms, no nucleotide sequence which is capable of/enables transposition and no nucleotide sequence which imparts resistance to antibiotics remaining at the target site.

TABLE 12

Intergenic regions as target sites for integration of open reading frames, genes and alleles

| Reference | Access number | Position of sequence start | Position of sequence end |
|---|---|---|---|
| EP1108790 | AX120085 | 192176 | 194501 |
| EP1108790 | AX127145 | 235840 | 237311 |
| EP1108790 | AX127145 | 236096 | 237311 |
| EP1108790 | AX127148 | 322628 | 330877 |
| EP1108790 | AX127148 | 334045 | 336467 |
| EP1108790 | AX127148 | 289565 | 291841 |
| EP1108790 | AX127149 | 154823 | 161111 |
| EP1108790 | AX127149 | 190088 | 193497 |
| EP1108790 | AX127149 | 27398 | 28707 |
| EP1108790 | AX127149 | 61478 | 62944 |
| EP1108790 | AX127149 | 116234 | 117561 |
| EP1108790 | AX127149 | 140847 | 144605 |
| EP1108790 | AX127150 | 113274 | 114324 |
| EP1108790 | AX127152 | 244281 | 246403 |

TABLE 13

Target sites coding for phages or phage components suitable for integration of open reading frames, genes and alleles

| Reference | Access number | Position of sequence start | Position of Sequence end |
|---|---|---|---|
| EP1108790 | AX127149 | 50474 | 51049 |
| EP1108790 | AX127149 | 67886 | 68587 |
| EP1108790 | AX127151 | 72893 | 73480 |
| EP1108790 | AX127149 | 88231 | 89445 |
| EP1108790 | AX127148 | 139781 | 140155 |
| EP1108790 | AX127148 | 140546 | 141001 |
| EP1108790 | AX127149 | 194608 | 195294 |
| EP1108790 | AX127147 | 200185 | 200940 |
| EP1108790 | AX127147 | 208157 | 208450 |
| EP1108790 | AX127149 | 269616 | 269948 |
| EP1108790 | AX127148 | 336468 | 338324 |
| EP1108790 | AX127148 | 342235 | 342681 |
| EP1108790 | AX127148 | 343518 | 345356 |
| EP1108790 | AX127148 | 345872 | 346207 |

During work on the present invention, it was possible to incorporate a second copy of an lysC$^{FBR}$ allele into the gluB gene of *Corynebacterium glutamicum* such that no nucleotide sequence which is capable of/enables episomal replication in microorganisms, no nucleotide sequence which is capable of/enables transposition and no nucleotide sequence which imparts resistance to antibiotics remained at the gluB gene site. This strain, which is called DSM13994glu::lysC, carries the lysC$^{FBR}$ allele lysC T311I at its natural lysC site and a second copy of the lysC$^{FBR}$ allele lysC T311I at a second site (target site), namely the gluB gene. A plasmid with the aid of which the incorporation of the lysC$^{FBR}$ allele into the gluB gene can be achieved is shown in FIG. 1. It carries the name pK18mobsacBglu1_1.

During work on the present invention, it was furthermore possible to incorporate a copy of an lysC$^{FBR}$ allele into the target site of the gluB gene of *Corynebacterium glutamicum* such that no nucleotide sequence which is capable of/enables episomal replication in microorganisms, no nucleotide sequence which is capable of/enables transposition and no nucleotide sequence which imparts resistance to antibiotics remained at the gluB gene site. This strain, which is called DSM12866glu::lysC, carries the wild-type form of the lysC gene at its natural lysC site and a second copy of the lysC gene in the form of the lysC$^{FBR}$ allele lysC T311I at a second site (target site), namely the gluB gene. It has been deposited under number DSM15039 at the Deutsche Sammlung für Mikroorganismen und Zellkulturen (German Collection of Microorganisms and Cell Cultures). A plasmid with the aid of which the incorporation of the lysC$^{FBR}$ allele into the gluB gene can be achieved is shown in FIG. 1. It carries the name pK18mobsacBglu1_1.

During work on the present invention, it was furthermore possible to incorporate a copy of an lysC$^{FBR}$ allele into the target site of the aecD gene of *Corynebacterium glutamicum* such that no nucleotide sequence which is capable of/enables episomal replication in microorganisms, no nucleotide sequence which is capable of/enables transposition and no nucleotide sequence which imparts resistance to antibiotics remained at the aecD gene site. This strain, which is called DSM12866aecD::lysC, carries the wild-type form of the lysC gene at its natural lysC site and a second copy of the lysC gene in the form of the lysC$^{FBR}$ allele lysc T311I at a second site (target site), namely the aecD gene. A plasmid with the aid of which the incorporation of the lysC$^{FBR}$ allele into the aecD gene can be achieved is shown in FIG. 2. It carries the name pK18mobsacBaecD1_1.

During work on the present invention, it was furthermore possible to incorporate a copy of an lysC$^{FBR}$ allele into the target site of the pck gene of *Corynebacterium glutamicum* such that no nucleotide sequence which is capable of/enables episomal replication in microorganisms, no nucleotide sequence which is capable of/enables transposition and no nucleotide sequence which imparts resistance to antibiotics remained at the pck gene site. This strain, which is called DSM12866pck::lysC, carries the wild-type form of the lysC gene at its natural lysC site and a second copy of the lysC gene in the form of the lysC$^{FBR}$ allele lysC T311I at a second site (target site), namely the pck gene. A plasmid with the aid of which the incorporation into the pck gene can be achieved is shown in FIG. 3. It carries the name pK18mobsacBpck1_1.

During work on the present invention, it was furthermore possible to incorporate a copy of the ddh gene into the target site of the gluB gene of *Corynebacterium glutamicum* such that no nucleotide sequence which is capable of/enables episomal replication in microorganisms, no nucleotide sequence which is capable of/enables transposition and no nucleotide sequence which imparts resistance to antibiotics remained at the gluB gene site. This strain, which is called DSM12866glu::ddh, carries a copy of the ddh gene at its natural ddh site and a second copy of the ddh gene at a second site (target site), namely the gluB gene. A plasmid with the aid of which the incorporation of the ddh gene into the gluB gene can be achieved is shown in FIG. 4. It carries the name pK18mobsacBgluB2_1.

During work on the present invention, it was furthermore possible to incorporate a copy of the dapA gene into the target site of the aecD gene of *Corynebacterium glutamicum* such that no nucleotide sequence which is capable of/enables episomal replication in microorganisms, no nucleotide sequence which is capable of/enables transposition and no nucleotide sequence which imparts resistance to antibiotics remained at the aecD gene site. This strain, which is called DSM12866aecD::dapA, carries a copy of the dapA gene at its natural dapA site and a second copy of the dapA gene at a second site (target site), namely the aecD gene. A plasmid with the aid of which the incorporation of the dapA gene into the aecD gene can be achieved is shown in FIG. 5. It carries the name pK18mobsacBaecD2_1.

During work on the present invention, it was furthermore possible to incorporate a copy of a pyc allele into the target site of the pck gene of *Corynebacterium glutamicum* such that no nucleotide sequence which is capable of/enables episomal replication in microorganisms, no nucleotide sequence which is capable of/enables transposition and no nucleotide sequence which imparts resistance to antibiotics remained at the pck gene site. This strain, which is called DSM12866pck::pyc, carries a copy of the wild-type form of the pyc gene at its natural pyc site and a second copy of the pyc gene in the form of the pyc allele pyc P458S at a second site (target site), namely the pck gene. A plasmid with the aid of which the incorporation of the pyc allele into the pck gene can be achieved is shown in FIG. 6. It carries the name pK18mobsacBpck1_3.

The coryneform bacteria produced according to the invention can be cultured continuously or discontinuously in the batch process (batch culture) or in the fed batch (feed process) or repeated fed batch process (repetitive feed process) for the purpose of production of chemical compounds. A summary of known culture methods is described in the textbook by Chmiel (Bioprozesstechnik 1. Einführung in die Bioverfahrenstechnik (Gustav Fischer Verlag, Stuttgart, 1991)) or in the textbook by Storhas (Bioreaktoren und periphere Einrichtungen (Vieweg Verlag, Braunschweig/Wiesbaden, 1994)).

The culture medium to be used must meet the requirements of the particular strains in a suitable manner. Descriptions of culture media for various microorganisms are contained in the handbook "Manual of Methods for General Bacteriology" of the American Society for Bacteriology (Washington D.C., USA, 1981).

Sugars and carbohydrates, such as e.g. glucose, sucrose, lactose, fructose, maltose, molasses, starch and cellulose, oils and fats, such as e.g. soya oil, sunflower oil, groundnut oil and coconut fat, fatty acids, such as e.g. palmitic acid, stearic acid and linoleic acid, alcohols, such as e.g. glycerol and ethanol, and organic acids, such as e.g. acetic acid or lactic acid, can be used as the source of carbon. These substances can be used individually or as a mixture.

Organic nitrogen-containing compounds, such as peptones, yeast extract, meat extract, malt extract, corn steep liquor, soya bean flour and urea, or inorganic compounds, such as ammonium sulfate, ammonium chloride, ammonium phosphate, ammonium carbonate and ammonium nitrate, can be used as the source of nitrogen. The sources of nitrogen can be used individually or as a mixture.

Phosphoric acid, potassium dihydrogen phosphate or dipotassium hydrogen phosphate or the corresponding sodium-containing salts can be used as the source of phosphorus. The culture medium must furthermore comprise salts of metals, such as e.g. magnesium sulfate or iron sulfate, which are necessary for growth. Finally, essential growth substances, such as amino acids and vitamins, can be employed in addition to the above-mentioned substances. Suitable precursors can moreover be added to the culture medium. The starting substances mentioned can be added to the culture in the form of a single batch, or can be fed in during the culture in a suitable manner.

Basic compounds, such as sodium hydroxide, potassium hydroxide, ammonia or aqueous ammonia, or acid compounds, such as phosphoric acid or sulfuric acid, can be employed in a suitable manner to control the pH of the culture. Antifoams, such as e.g. fatty acid polyglycol esters, can be employed to control the development of foam. Suitable substances having a selective action, such as e.g. antibiotics, can be added to the medium to maintain the stability of plasmids. To maintain aerobic conditions, oxygen or oxygen-containing gas mixtures, such as e.g. air, are introduced into the culture. The temperature of the culture is usually 20° C. to 45° C., and preferably 25° C. to 40° C. Culturing is continued until a maximum of the desired chemical compound has formed. This target is usually reached within 10 hours to 160 hours.

It has been found that the coryneform bacteria according to the invention, in particular the coryneform bacteria which produce L-lysine, have an unexpectedly high stability. They were stable for at least 10–20, 20–30, 30–40, 40–50, preferably at least 50–60, 60–70, 70–80 and 80–90 generations or cell division cycles.

The following microorganisms have been deposited:

The strain *Corynebacterium glutamicum* DSM12866glu::lysC was deposited in the form of a pure culture on 5th Jun. 2002 under number DSM15039 at the Deutsche Sammlung für Mikroorganismen und Zellkulturen (DSMZ=German Collection of Microorganisms and Cell Cultures, Braunschweig, Germany) in accordance with the Budapest Treaty.

The plasmid pK18mobsacBglu1_1 was deposited in the form of a pure culture of the strain *E. coli* DH5αmcr/pK18mobsacBglu1_1 (=DH5alphamcr/pK18mobsacBglu1_1) on 20th Apr. 2001 under number DSM14243 at the Deutsche Sammlung für Mikroorganismen und Zellkulturen (DSMZ, Braunschweig, Germany) in accordance with the Budapest Treaty.

The plasmid pK18mobsacBaecD1_1 was deposited in the form of a pure culture of the strain *E. coli* DH5αmcr/pK18mobsacBaecD1_1 (=DH5alphamcr/pK18mobsacBaecD1_1) on 5th Jun. 2002 under number DSM15040 at the Deutsche Sammlung für Mikroorganismen und Zellkulturen (DSMZ, Braunschweig, Germany) in accordance with the Budapest Treaty.

EXAMPLE 1

Incorporation of a second copy of the lysC$^{FBR}$ allele into the chromosome of the strain DSM13994 and of the strain DSM12866

The *Corynebacterium glutamicum* strain DSM13994 was produced by multiple, non-directed mutagenesis, selection and mutant selection from *C. glutamicum* ATCC13032. The strain is resistant to the lysine analogue S-(2-aminoethyl)-L-cysteine and has a feed back-resistant aspartate kinase which is insensitive to inhibition by a mixture of lysine and threonine (in each case 25 mM). The nucleotide sequence of the lysC$^{FBR}$ allele of this strain is shown as SEQ ID NO:3. It is also called lysC T311I in the following. The amino acid sequence of the aspartate kinase protein coded is shown as SEQ ID NO:4. A pure culture of this strain was deposited on 16th Jan. 2001 at the Deutsche Sammlung für Mikroorganismen und Zellkulturen (DSMZ=German Collection of Microorganisms and Cell Cultures, Braunschweig, Germany) in accordance with the Budapest Treaty.

The strain DSM12866 was produced from *C. glutamicum* ATCC13032 by non-directed mutagenesis and selection of the mutants with the best L-lysine accumulation. It is methionine-sensitive. Growth on minimal medium comprising L-methionine can be re-established by addition of threonine. This strain has the wild-type form of the lysC gene shown as SEQ ID NO:1. The corresponding amino acid sequence of the wild-type aspartate kinase protein is shown as SEQ ID NO:2. A pure culture of this strain was deposited on 10th Jun. 1999 at the Deutsche Sammlung für Mikroorganismen und Zellkulturen (DSMZ, Braunschweig, Germany) in accordance with the Budapest Treaty.

1.1 Isolation and Sequencing of the DNA of the lysC Allele of Strain DSM13994

From the strain DSM13994, chromosomal DNA is isolated by the conventional methods (Eikmanns et al., Microbiology 140: 1817–1828 (1994)). With the aid of the polymerase chain reaction, a DNA section which carries the lysC gene or allele is amplified. On the basis of the sequence of the lysC gene known for *C. glutamicum* (Kalinowski et al., Molecular Microbiology, 5 (5), 1197–1204 (1991); Accession Number X57226), the following primer oligonucleotides were chosen for the PCR:

```
lysC1beg:
                                        (SEQ ID No: 5)
5' TA(G GAT CC)T CCG GTG TCT GAC CAC GGT G 3' lysC2end:
                                        (SEQ ID NO: 6)
5' AC(G GAT CC)G CTG GGA AAT TGC GCT CTT CC 3'
```

The primers shown are synthesized by MWG Biotech and the PCR reaction is carried out by the standard PCR method of Innis et al. (PCR Protocols. A Guide to Methods and Applications, 1990, Academic Press). The primers allow amplification of a DNA section of approx. 1.7 kb in length, which carries the lysc gene or allele. The primers moreover contain the sequence for a cleavage site of the restriction endonuclease BamHI, which is marked by parentheses in the nucleotide sequence shown above.

The amplified DNA fragment of approx. 1.7 kb in length which carries the lysC allele of the strain DSM13994 is identified by electrophoresis in a 0.8% agarose gel, isolated from the gel and purified by conventional methods (QIAquick Gel Extraction Kit, Qiagen, Hilden).

Ligation of the fragment is then carried out by means of the Topo TA Cloning Kit (Invitrogen, Leek, The Netherlands, Cat. Number K4600-01) in the vector pCRII-TOPO. The ligation batch is transformed in the *E. coli* strain TOP10 (Invitrogen, Leek, The Netherlands). Selection of plasmid-carrying cells is made by plating out the transformation batch on kanamycin (50 mg/l)-containing LB agar with X-Gal (5-bromo-4-chloro-3-indolyl β-D-galactopyranoside, 64 mg/l).

The plasmid obtained is checked by means of restriction cleavage, after isolation of the DNA, and identified in agarose gel. The resulting plasmid is called pCRIITO-POlysC.

The nucleotide sequence of the amplified DNA fragment or PCR product is determined by the dideoxy chain termination method of Sanger et al. (Proceedings of the National Academy of Sciences USA, 74:5463–5467 (1977)) using the "ABI Prism 377" sequencing apparatus of PE Applied Biosystems (Weiterstadt, Germany). The sequence of the coding region of the PCR product is shown in SEQ ID No:3. The amino acid sequence of the associated aspartate kinase protein is shown in SEQ ID NO:4.

The base thymine is found at position 932 of the nucleotide sequence of the coding region of the lysC$^{FBR}$ allele of strain DSM13994 (SEQ ID NO:3). The base cytosine is found at the corresponding position of the wild-type gene (SEQ ID NO:1).

The amino acid isoleucine is found at position 311 of the amino acid sequence of the aspartate kinase protein of strain DSM13994 (SEQ ID No:4). The amino acid threonine is found at the corresponding position of the wild-type protein (SEQ ID No:2).

The lysC allele, which contains the base thymine at position 932 of the coding region and accordingly codes for an aspartate kinase protein which contains the amino acid isoleucine at position 311 of the amino acid sequence, is called the lysC$^{FBR}$ allele or lysC T311I in the following.

The plasmid pCRIITOPOlysC, which carries the lysC$^{FBR}$ allele lysC T311I, was deposited in the form of a pure culture of the strain *E. coli* TOP 10/pCRIITOPOlysC under number DSM14242 on 20th Apr. 2001 at the Deutsche Sammlung für Mikroorganismen und Zellkulturen (DSMZ, Braunschweig, Germany) in accordance with the Budapest Treaty.

1.2 Construction of the Replacement Vector pK18mobsacBglu1_1

The *Corynebacterium glutamicum* strain ATCC13032 is used as the donor for the chromosomal DNA. From the strain ATCC13032, chromosomal DNA is isolated using the conventional methods (Eikmanns et al., Microbiology 140: 1817–1828 (1994)). With the aid of the polymerase chain reaction, a DNA fragment which carries the gluB gene and surrounding regions is amplified. On the basis of the sequence of the gluABCD gene cluster known for *C. glutamicum* (Kronemeyer et al., Journal of Bacteriology, 177: 1152–1158 (1995)) (Accession Number X81191), the following primer oligonucleotides are chosen for the PCR:

gluBgl1:
(SEQ ID NO: 7)
5' TA(A GAT CT)G TGT TGG ACG TCA TGG CAA G 3' gluBgl2:
(SEQ ID NO: 8)
5' AC(A GAT CT)T GAA GCC AAG TAC GGC CAA G 3'

The primers shown are synthesized by MWG Biotech and the PCR reaction is carried out by the standard PCR method of Innis et al. (PCR Protocols. A Guide to Methods and Applications, 1990, Academic Press). The primers allow amplification of a DNA fragment of approx 1.7 kb in size, which carries the gluB gene and surrounding regions. The surrounding regions are a sequence section approx. 0.33 kb in length upstream of the gluB gene, which represents the 3' end of the gluA gene, and a sequence section approx. 0.44 kb in length downstream of the gluB gene, which represents the 5' end of the gluC gene. The primers moreover contain the sequence for the cleavage site of the restriction endonuclease BglII, which is marked by parentheses in the nucleotide sequence shown above.

The amplified DNA fragment of approx. 1.7 kb in length which carries the gluB gene and surrounding regions is identified by means of electrophoresis in a 0.8% agarose gel and isolated from the gel and purified by conventional methods (QIAquick Gel Extraction Kit, Qiagen, Hilden).

Ligation of the fragment is then carried out by means of the TOPO TA Cloning Kit (Invitrogen, Leek, The Netherlands, Cat. Number K4600-01) in the vector pCRII-TOPO. The ligation batch is transformed in the *E. coli* strain TOP10 (Invitrogen, Leek, The Netherlands). Selection of plasmid-carrying cells is made by plating out the transformation batch on kanamycin (50 mg/l)-containing LB agar with X-Gal (5-bromo-4-chloro-3-indolyl β-D-galactopyranoside, 64 mg/l).

The plasmid obtained is checked by means of restriction cleavage, after isolation of the DNA, and identified in agarose gel. The resulting plasmid is called pCRII-TOPO-glu.

The plasmid pCRII-TOPOglu is cleaved with the restriction enzyme BglII (Amersham-Pharmacia, Freiburg, Germany) and after separation in an agarose gel (0.8%) with the aid of the QIAquick Gel Extraction Kit (Qiagen, Hilden, Germany) the gluB fragment of approx. 1.7 kb is isolated from the agarose gel and employed for ligation with the mobilizable cloning vector pK18mobsacB described by Schäfer et al. (Gene 14: 69–73 (1994)). This is cleaved beforehand with the restriction enzyme BamHI and dephosphorylated with alkaline phosphatase (Alkaline Phosphatase, Boehringer Mannheim), mixed with the gluB fragment of approx. 1.7 kb, and the mixture is treated with T4 DNA Ligase (Amersham-Pharmacia, Freiburg, Germany).

The *E. coli* strain DH5α (Grant et al.; Proceedings of the National Academy of Sciences USA, 87 (1990) 4645–4649) is then transformed with the ligation batch (Hanahan, In. DNA Cloning. A Practical Approach. Vol. 1, ILR-Press, Cold Spring Harbor, N.Y., 1989). Selection of plasmid-carrying cells is made by plating out the transformation batch on LB agar (Sambrook et al., Molecular Cloning: A Laboratory Manual. 2$^{nd}$ Ed., Cold Spring Harbor, N.Y., 1989), which is supplemented with 50 mg/l kanamycin.

Plasmid DNA is isolated from a transformant with the aid of the QIAprep Spin Miniprep Kit from Qiagen and checked by restriction cleavage and subsequent agarose gel electrophoresis. The plasmid is called pK18mobsacBglu1.

Plasmid DNA was isolated from the strain DSM14242 (see Example 1.1), which carries the plasmid pCRIITO-POlysC, and cleaved with the restriction enzyme BamHI (Amersham-Pharmacia, Freiburg, Germany), and after separation in an agarose gel (0.8%) with the aid of the QIAquick Gel Extraction Kit (Qiagen, Hilden, Germany) the lysC$^{FBR}$-containing DNA fragment of approx. 1.7 kb in length was isolated from the agarose gel and employed for ligation with the vector pK18mobsacBglu1 described above. This is cleaved beforehand with the restriction enzyme BamHI, dephosphorylated with alkaline phosphatase (Alkaline Phosphatase, Boehringer Mannheim, Germany), mixed with the lysC$^{FBR}$ fragment of approx. 1.7 kb and the mixture is treated with T4 DNA Ligase (Amersham-Pharmacia, Freiburg, Germany).

The E. coli strain DH5αmcr (Life Technologies GmbH, Karlsruhe, Germany) is then transformed with the ligation batch (Hanahan, In: DNA Cloning. A Practical Approach. Vol. 1, ILR-Press, Cold Spring Harbor, N.Y., 1989). Selection of plasmid-carrying cells is made by plating out the transformation batch on LB agar (Sambrook et al., Molecular Cloning: A Laboratory Manual. 2$^{nd}$ Ed., Cold Spring Harbor, N.Y., 1989), which was supplemented with 50 mg/l kanamycin.

Plasmid DNA is isolated from a transformant with the aid of the QIAprep Spin Miniprep Kit from Qiagen and checked by restriction cleavage and subsequent agarose gel electrophoresis. The plasmid is called pK18mobsacBglu1_1. A map of the plasmid is shown in FIG. 1.

The plasmid pK18mobsacBglu1_1 was deposited in the form of a pure culture of the strain E. coli DH5αmcr/pK18mobsacBglu1_1 (=DH5alphamcr/pK18mobsacBglu1_1) under number DSM14243 on 20.04.2001 at the Deutsche Sammlung für Mikroorganismen und Zellkulturen (DSMZ, Braunschweig, Germany) in accordance with the Budapest Treaty.

1.3 Incorporation of a Second Copy of the lysC$^{FBR}$ Allele lysC T311I into the Chromosome (Target Site: gluB Gene) of the Strain DSM13994 by Means of the Replacement Vector pK18mobsacBglu1_1

The vector pK18mobsacBglu1_1 described in Example 1.2 is transferred by the protocol of Schäfer et al. (Journal of Microbiology 172: 1663–1666 (1990)) into the C. glutamicum strain DSM13994 by conjugation. The vector cannot replicate independently in DSM13994 and is retained in the cell only if it has integrated into the chromosome. Selection of clones or transconjugants with integrated pK18mobsacBglu1_1 is made by plating out the conjugation batch on LB agar (Sambrook et al., Molecular Cloning: A Laboratory Manual. 2$^{nd}$ Ed., Cold Spring Harbor, N.Y., 1989), which is supplemented with 15 mg/l kanamycin and 50 mg/l nalidixic acid. Kanamycin-resistant transconjugants are plated out on LB agar plates with 25 mg/l kanamycin and incubated for 48 hours at 33° C.

For selection of mutants in which excision of the plasmid has taken place as a consequence of a second recombination event, the clones are cultured for 20 hours in LB liquid medium and then plated out on LB agar with 10% sucrose and incubated for 48 hours.

The plasmid pK18mobsacBglu1_1, like the starting plasmid pK18mobsacB, contains, in addition to the kanamycin resistance gene, a copy of the sacB gene which codes for levan sucrase from Bacillus subtilis. The expression which can be induced by sucrose leads to the formation of levan sucrase, which catalyses the synthesis of the product levan, which is toxic to C. glutamicum. Only those clones in which the integrated pK18mobsacBglu1_1 has excised as the consequence of a second recombination event therefore grow on LB agar. Depending on the position of the second recombination event, after the excision the second copy of the lysC$^{FBR}$ allele manifests itself in the chromosome at the gluB locus, or the original gluB locus of the host remains.

Approximately 40 to 50 colonies are tested for the phenotype "growth in the presence of sucrose" and "non-growth in the presence of kanamycin". Approximately 20 colonies which show the phenotype "growth in the presence of sucrose" and "non-growth in the presence of kanamycin" are investigated with the aid of the polymerase chain reaction. A DNA fragment which carries the gluB gene and surrounding regions is amplified here from the chromosomal DNA of the colonies. The same primer oligonucleotides as are described in Example 1.2 for the construction of the integration plasmid are chosen for the PCR.

```
gluBgl1:
                                     (SEQ ID NO: 7)
5' TA(A GAT CT)G TGT TGG ACG TCA TGG CAA G 3' gluBgl2:
                                     (SEQ ID NO: 8)
5' AC(A GAT CT)T GAA GCC AAG TAC GGC CAA G 3'
```

The primers allow amplification of a DNA fragment approx. 1.7 kb in size in control clones with the original gluB locus. In clones with a second copy of the lysC$^{FBR}$ allele in the chromosome at the gluB locus, DNA fragments with a size of approx. 3.4 kb are amplified.

The amplified DNA fragments are identified by means of electrophoresis in a 0.8% agarose gel.

A clone which, in addition to the copy present at the lysC locus, has a second copy of the lysC$^{FBR}$ allele lysC T311I at the gluB locus in the chromosome was identified in this manner. This clone was called strain DSM13994glu::lysC.

1.4 Incorporation of a Second Copy of the lysC Gene in the Form of the lysC$^{FBR}$ Allele lysC T311I into the Chromosome (Target Site: gluB Gene) of the Strain DSM12866 by Means of the Replacement Vector pK18mobsacBglu1_1

As described in Example 1.3, the plasmid pK18mobsacBglu1_1 is transferred into the C. glutamicum strain DSM12866 by conjugation. A clone which, in addition to the copy of the wild-type gene present at the lysC locus, has a second copy of the lysC gene in the form of the lysC$^{FBR}$ allele lysC T311I at the gluB locus in the chromosome was identified in the manner described in 1.3. This clone was called strain DSM12866glu::lysC.

The Corynebacterium glutamicum strain according to the invention which carries a second copy of an lysC$^{FBR}$ allele in the gluB gene was deposited in the form of a pure culture of the strain Corynebacterium glutamicum DSM12866glu::lysC on 5th Jun. 2002 under number DSM15039 at the Deutsche Sammlung für Mikroorganismen und Zellkulturen (DSMZ, Braunschweig, Germany) in accordance with the Budapest Treaty.

1.5 Construction of the Replacement Vector pK18mobsacBpck1_1

The Corynebacterium glutamicum strain ATCC13032 is used as the donor for the chromosomal DNA. From the strain ATCC13032, chromosomal DNA is isolated using the conventional methods (Eikmanns et al., Microbiology 140: 1817–1828 (1994)). With the aid of the polymerase chain reaction, a DNA fragment which carries the pck gene and surrounding regions is amplified. On the basis of the sequence of the pck gene known for *C. glutamicum* (EP1094111 and Riedel et al., Journal of Molecular and Microbiological Biotechnology 3:573–583 (2001)) (Accession Number AJ269506), the following primer oligonucleotides are chosen for the PCR:

```
pck_beg:
                                    (SEQ ID NO: 9)
5' TA(A GAT CT) G CCG GCA TGA CTT CAG TTT 3' pck_end:
                                    (SEQ ID NO: 10)
5' AC(A GAT CT) G GTG GGA GCC TTT CTT GTT ATT 3'
```

The primers shown are synthesized by MWG Biotech and the PCR reaction is carried out by the standard PCR method of Innis et al. (PCR Protocols. A Guide to Methods and Applications, 1990, Academic Press). The primers allow amplification of a DNA fragment of approx 2.9 kb in size, which carries the pck gene and adjacent regions. The primers moreover contain the sequence for the cleavage site of the restriction endonuclease BglII, which is marked by parentheses in the nucleotide sequence shown above.

The amplified DNA fragment of approx. 2.9 kb in length which carries the pck gene and surrounding regions is identified by means of electrophoresis in a 0.8% agarose gel and isolated from the gel and purified by conventional methods (QIAquick Gel Extraction Kit, Qiagen, Hilden).

Ligation of the fragment is then carried out by means of the TOPO TA Cloning Kit (Invitrogen, Leek, The Netherlands, Cat. Number K4600-01) in the vector pCRII-TOPO. The ligation batch is transformed in the *E. coli* strain TOP10 (Invitrogen, Leek, The Netherlands). Selection of plasmid-carrying cells is made by plating out the transformation batch on kanamycin (50 mg/l)-containing LB agar with X-Gal (64 mg/l).

The plasmid obtained is checked by means of restriction cleavage, after isolation of the DNA, and identified in agarose gel. The resulting plasmid is called pCRII-TOPOpck.

The plasmid pCRII-TOPOpck is cleaved with the restriction enzyme BglII (Amersham-Pharmacia, Freiburg, Germany) and after separation in an agarose gel (0.8%) with the aid of the QIAquick Gel Extraction Kit (Qiagen, Hilden, Germany) the pck fragment of approx. 2.9 kb is isolated from the agarose gel and employed for ligation with the mobilizable cloning vector pK18mobsacB described by Schäfer et al. (Gene 14: 69–73 (1994)). This is cleaved beforehand with the restriction enzyme BamHI and dephosphorylated with alkaline phosphatase (Alkaline Phosphatase, Boehringer Mannheim), mixed with the pck fragment of approx. 2.9 kb, and the mixture is treated with T4 DNA Ligase (Amersham-Pharmacia, Freiburg, Germany).

The *E. coli* Strain DH5α (Grant et al.; Proceedings of the National Academy of Sciences USA, 87 (1990) 4645–4649) is then transformed with the ligation batch (Hanahan, In. DNA Cloning. A Practical Approach. Vol. 1, ILR-Press, Cold Spring Harbor, N.Y., 1989) Selection of plasmid-carrying cells is made by plating out the transformation batch on LB agar (Sambrook et al., Molecular Cloning: A Laboratory Manual. 2$^{nd}$ Ed., Cold Spring Harbor, N.Y., 1989), which is supplemented with 50 mg/l kanamycin.

Plasmid DNA is isolated from a transformant with the aid of the QIAprep Spin Miniprep Kit from Qiagen and checked by restriction cleavage and subsequent agarose gel electrophoresis. The plasmid is called pK18mobsacBpck1.

Plasmid DNA was isolated from the strain DSM14242 (see Example 1.1), which carries the plasmid pCRIITO-POlysC, and cleaved with the restriction enzyme BamHI (Amersham-Pharmacia, Freiburg, Germany), and after separation in an agarose gel (0.8%) with the aid of the QIAquick Gel Extraction Kit (Qiagen, Hilden, Germany) the lysC$^{FBR}$-containing DNA fragment approx. 1.7 kb long was isolated from the agarose gel and employed for ligation with the vector pK18mobsacBpck1 described above. This is cleaved beforehand with the restriction enzyme BamHI, dephosphorylated with alkaline phosphatase (Alkaline Phosphatase, Boehringer Mannheim, Germany), mixed with the lysC$^{FBR}$ fragment of approx. 1.7 kb and the mixture is treated with T4 DNA Ligase (Amersham-Pharmacia, Freiburg, Germany).

The *E. coli* strain DH5αmcr (Life Technologies GmbH, Karlsruhe, Germany) is then transformed with the ligation batch (Hanahan, In: DNA Cloning. A Practical Approach. Vol. 1, ILR-Press, Cold Spring Harbor, N.Y., 1989). Selection of plasmid-carrying cells is made by plating out the transformation batch on LB agar (Sambrook et al., Molecular Cloning: A Laboratory Manual. 2$^{nd}$ Ed., Cold Spring Harbor, N.Y., 1989), which was supplemented with 50 mg/l kanamycin.

Plasmid DNA is isolated from a transformant with the aid of the QIAprep Spin Miniprep Kit from Qiagen and checked by restriction cleavage and subsequent agarose gel electrophoresis. The plasmid is called pK18mobdsacBpck1_1. A map of the plasmid is shown in FIG. 3.

1.6 Incorporation of a Second Copy of the lysC Gene in the Form of the lysC$^{FBR}$ Allele lysC T311I into the Chromosome (Target Site: pck Gene) of the Strain DSM12866 by Means of the Replacement Vector pK18mobsacBpck1_1

As described in Example 1.3, the plasmid pK18mobsacBpck1_1 described in Example 1.5 is transferred into the *C. glutamicum* strain DSM12866 by conjugation. Selection is made for targeted recombination events in the chromosome of *C. glutamicum* DSM12866 as described in Example 1.3. Depending on the position of the second recombination event, after the excision the second copy of the lysC$^{FBR}$ allele manifests itself in the chromosome at the pck locus, or the original pck locus of the host remains.

Approximately 40 to 50 colonies are tested for the phenotype "growth in the presence of sucrose" and "non-growth in the presence of kanamycin". Approximately 20 colonies which show the phenotype "growth in the presence of sucrose" and "non-growth in the presence of kanamycin" are investigated with the aid of the polymerase chain reaction. A DNA fragment which carries the pck gene and surrounding regions is amplified here from the chromosomal DNA of the colonies. The same primer oligonucleotides as are described in Example 1.5 for the construction of the integration plasmid are chosen for the PCR.

```
pck_beg:
                                    (SEQ ID NO: 9)
5' TA(A GAT CT) G CCG GCA TGA CTT CAG TTT 3' pck_end:
                                    (SEQ ID NO: 10)
5' AC(A GAT CT) G GTG GGA GCC TTT CTT GTT ATT 3'
```

The primers allow amplification of a DNA fragment approx. 2.9 kb in size in control clones with the original pck locus. In clones with a second copy of the lysC$^{FBR}$ allele in the chromosome at the pck locus, DNA fragments with a size of approx. 4.6 kb are amplified.

The amplified DNA fragments are identified by means of electrophoresis in a 0.8% agarose gel.

A clone which, in addition to the copy of the wild-type gene present at the lysC locus, has a second copy of the lysC gene in the form of the lysC$^{FBR}$ allele lysC T311I at the pck locus in the chromosome was identified in this manner. This clone was called strain DSM12866pck::lysC.

1.7 Construction of the Replacement Vector pK18mobsacBaecD1_1

The *Corynebacterium glutamicum* strain ATCC13032 is used as the donor for the chromosomal DNA. From the strain ATCC13032, chromosomal DNA is isolated using the conventional methods (Eikmanns et al., Microbiology 140: 1817–1828 (1994)). With the aid of the polymerase chain reaction, a DNA fragment which carries the aecD gene and surrounding regions is amplified. On the basis of the sequence of the aecD gene known for *C. glutamicum* (Rossol et al., Journal of Bacteriology 174:2968–2977 (1992)) (Accession Number M89931), the following primer oligonucleotides are chosen for the PCR:

```
aecD_beg:
5' GAA CTT ACG CCA AGC TGT TC 3'   (SEQ ID NO: 11)

aecD_end:
5' AGC ACC ACA ATC AAC GTG AG 3'   (SEQ ID NO: 12)
```

The primers shown are synthesized by MWG Biotech and the PCR reaction is carried out by the standard PCR method of Innis et al. (PCR Protocols. A Guide to Methods and Applications, 1990, Academic Press). The primers allow amplification of a DNA fragment of approx 2.1 kb in size, which carries the aecD gene and adjacent regions.

The amplified DNA fragment of approx. 2.1 kb in length is identified by means of electrophoresis in a 0.8% agarose gel and isolated from the gel and purified by conventional methods (QIAquick Gel Extraction Kit, Qiagen, Hilden).

The DNA fragment purified is cleaved with the restriction enzyme BamHI and EcoRV (Amersham Pharmacia, Freiburg, Germany). The ligation of the fragment in the vector pUC18 then takes place (Norrander et al., Gene 26:101–106 (1983)). This is cleaved beforehand with the restriction enzymes BglII and SmaI, dephosphorylated, mixed with the aecD-carrying fragment of approx. 1.5 kb, and the mixture is treated with T4 DNA Ligase (Amersham-Pharmacia, Freiburg, Germany). The ligation batch is transformed in the *E. coli* strain TOP10 (Invitrogen, Leek, The Netherlands). Selection of plasmid-carrying cells is made by plating out the transformation batch on kanamycin (50 mg/l)-containing LB agar with X-Gal (64 mg/l).

The plasmid obtained is checked by means of restriction cleavage, after isolation of the DNA, and identified in agarose gel. The resulting plasmid is called pUC18aecD.

Plasmid DNA was isolated from the strain DSM14242 (see Example 1.1) which carries the plasmid pCRIITO-POlysC and cleaved with the restriction enzyme BamHI (Amersham-Pharmacia, Freiburg, Germany) and then treated with Klenow polymerase. After separation in an agarose gel (0.8%) with the aid of the QIAquick Gel Extraction Kit (Qiagen, Hilden, Germany) the lysC$^{FBR}$-containing DNA fragment approx. 1.7 kb in length is isolated from the agarose gel and employed for ligation with the vector pUC18aecD described above. This is cleaved beforehand with the restriction enzyme StuI, dephosphorylated with alkaline phosphatase (Alkaline Phosphatase, Boehringer Mannheim, Germany), mixed with the lysC$^{FBR}$ fragment of approx. 1.7 kb and the mixture is treated with T4 DNA Ligase (Amersham-Pharmacia, Freiburg, Germany).

The *E. coli* strain DH5αmcr (Life Technologies GmbH, Karlsruhe, Germany) is then transformed with the ligation batch (Hanahan, In: DNA Cloning. A Practical Approach. Vol. 1, ILR-Press, Cold Spring Harbor, N.Y., 1989). Selection of plasmid-carrying cells is made by plating out the transformation batch on LB agar (Sambrook et al., Molecular Cloning: A Laboratory Manual. 2$^{nd}$ Ed., Cold Spring Harbor, N.Y., 1989), which was supplemented with 50 mg/l kanamycin.

Plasmid DNA is isolated from a transformant with the aid of the QIAprep Spin Miniprep Kit from Qiagen and checked by restriction cleavage and subsequent agarose gel electrophoresis. The plasmid is called pUC18aecD1.

The plasmid pUC18aecD1 is cleaved with the restriction enzyme KpnI and then treated with Klenow polymerase. The plasmid is then cleaved with the restriction enzyme SalI (Amersham-Pharmacia, Freiburg, Germany) and after separation in an agarose gel (0.8%) with the aid of the QIAquick Gel Extraction Kit (Qiagen, Hilden, Germany) the fragment of approx. 3.2 kb which carries aecD and lysC is isolated from the agarose gel and employed for ligation with the mobilizable cloning vector pK18mobsacB described by Schäfer et al. (Gene 14: 69–73 (1994)). This is cleaved beforehand with the restriction enzymes SmaI and SalI and dephosphorylated with alkaline phosphatase (Alkaline Phosphatase, Boehringer Mannheim), mixed with the fragment of approx. 3.2 kb which carries aecD and lysC, and the mixture is treated with T4 DNA Ligase (Amersham-Pharmacia, Freiburg, Germany).

The *E. coli* strain DH5α (Grant et al.; Proceedings of the National Academy of Sciences USA, 87 (1990) 4645–4649) is then transformed with the ligation batch (Hanahan, In. DNA Cloning. A Practical Approach. Vol. 1, ILR-Press, Cold Spring Harbor, N.Y., 1989). Selection of plasmid-carrying cells is made by plating out the transformation batch on LB agar (Sambrook et al., Molecular Cloning: A Laboratory Manual. 2$^{nd}$ Ed., Cold Spring Harbor, N.Y., 1989), which is supplemented with 50 mg/l kanamycin.

Plasmid DNA is isolated from a transformant with the aid of the QIAprep Spin Miniprep Kit from Qiagen and checked by restriction cleavage and subsequent agarose gel electrophoresis. The plasmid is called pK18mobsacBaecD1_1. A map of the plasmid is shown in FIG. 2.

The plasmid pK18mobsacBaecD1_1 was deposited in the form of a pure culture of the strain *E. coli* DH5αmcr/pK18mobsacBaecD1_1 (=DH5alphamcr/pK18mobsacBaecD1_1) on 5th Jun. 2002 under number DSM15040 at the Deutsche Sammlung für Mikroorganismen und Zellkulturen (DSMZ, Braunschweig, Germany) in accordance with the Budapest Treaty.

1.8 Incorporation of a Second Copy of the lysC Gene as the lysC$^{FBR}$ Allele into the Chromosome (Target Site: aecD Gene) of the Strain DSM12866 by Means of the Replacement Vector pK18mobsacBaecD1_1

As described in Example 1.3, the plasmid pK18mobsacBaecD1_1 described in Example 1.4 is transferred into the *C. glutamicum* strain DSM12866 by conjugation. Selection is made for targeted recombination events in the chromosome of *C. glutamicum* DSM12866 as described in Example 1.3. Depending on the position of the second recombination event, after the excision the second copy of the lysC$^{FBR}$ allele manifests itself in the chromosome at the aecD locus, or the original aecD locus of the host remains.

Approximately 40 to 50 colonies are tested for the phenotype "growth in the presence of sucrose" and "non-growth in the presence of kanamycin". Approximately 20 colonies which show the phenotype "growth in the presence of sucrose" and "non-growth in the presence of kanamycin" are investigated with the aid of the polymerase chain reaction. A DNA fragment which carries the aecD gene and surrounding regions is amplified here from the chromosomal DNA of the colonies. The same primer oligonucleotides as are described in Example 1.7 for the construction of the integration plasmid are chosen for the PCR.

```
aecD_beg:
5' GAA CTT ACG CCA AGC TGT TC 3'     (SEQ ID NO: 11)

aecD_end:
5' AGC ACC ACA ATC AAC GTG AG 3'     (SEQ ID NO: 12)
```

The primers allow amplification of a DNA fragment approx. 2.1 kb in size in control clones with the original aecD locus. In clones with a second copy of the lysC$^{FBR}$ allele in the chromosome at the aecD locus, DNA fragments with a size of approx. 3.8 kb are amplified.

The amplified DNA fragments are identified by means of electrophoresis in a 0.8% agarose gel.

A clone which, in addition to the copy of the wild-type gene present at the lysC locus, has a second copy of the lysC gene in the form of the lysC$^{FBR}$ allele lysC T311I at the aecD locus in the chromosome was identified in this manner. This clone was called strain DSM12866aecD::lysC.

EXAMPLE 2

Incorporation of a second copy of the ddh gene into the chromosome (target site: gluB gene) of the strain DSM12866

2.1 Construction of the Replacement Vector pK18mobsacBglu2_1

The *Corynebacterium glutamicum* strain ATCC13032 is used as the donor for the chromosomal DNA. From the strain ATCC13032, chromosomal DNA is isolated using the conventional methods (Eikmanns et al., Microbiology 140: 1817–1828 (1994)). With the aid of the polymerase chain reaction, a DNA fragment which carries the gluB gene and surrounding regions is amplified. On the basis of the sequence of the gluABCD gene cluster known for *C. glutamicum* (Kronemeyer et al., Journal of Bacteriology, 177: 1152–1158 (1995); EP1108790) (Accession Number X81191 and AX127149), the following primer oligonucleotides are chosen for the PCR:

```
gluA_beg:
5' CAC GGT TGC TCA TTG TAT CC 3'     (SEQ ID NO: 13)

gluD_end:
5' CGA GGC GAA TCA GAC TTC TT 3'     (SEQ ID NO: 14)
```

The primers shown are synthesized by MWG Biotech and the PCR reaction is carried out by the standard PCR method of Innis et al. (PCR Protocols. A Guide to Methods and Applications, 1990, Academic Press). The primers allow amplification of a DNA fragment of approx 4.4 kb in size, which carries the gluB gene and surrounding regions.

The amplified DNA fragment is identified by means of electrophoresis in a 0.8% agarose gel and isolated from the gel and purified by conventional methods (QIAquick Gel Extraction Kit, Qiagen, Hilden).

Ligation of the fragment is then carried out by means of the TOPO TA Cloning Kit (Invitrogen, Leek, The Netherlands, Cat. Number K4600-01) in the vector pCRII-TOPO. The ligation batch is transformed in the *E. coli* strain TOP10 (Invitrogen, Leek, The Netherlands). Selection of plasmid-carrying cells is made by plating out the transformation batch on kanamycin (50 mg/l)-containing LB agar with X-Gal (64 mg/l).

The plasmid obtained is checked by means of restriction cleavage, after isolation of the DNA, and identified in agarose gel. The resulting plasmid is called pCRII-TOPO-glu2.

The plasmid pCRII-TOPOglu2 is cleaved with the restriction enzymes EcoRI and SalI (Amersham-Pharmacia, Freiburg, Germany) and after separation in an agarose gel (0.8%) with the aid of the QIAquick Gel Extraction Kit (Qiagen, Hilden, Germany) the gluB fragment of approx. 3.7 kb is isolated from the agarose gel and employed for ligation with the mobilizable cloning vector pK18mobsacB described by Schäfer et al. (Gene 14, 69–73 (1994)). This is cleaved beforehand with the restriction enzymes EcoRI and SalI and dephosphorylated with alkaline phosphatase (Alkaline Phosphatase, Boehringer Mannheim), mixed with the gluB fragment of approx. 3.7 kb, and the mixture is treated with T4 DNA Ligase (Amersham-Pharmacia, Freiburg, Germany).

The *E. coli* Strain DH5α (Grant et al.; Proceedings of the National Academy of Sciences USA, 87 (1990) 4645–4649) is then transformed with the ligation batch (Hanahan, In. DNA Cloning. A Practical Approach. Vol. 1, ILR-Press, Cold Spring Harbor, N.Y., 1989). Selection of plasmid-carrying cells is made by plating out the transformation batch on LB agar (Sambrook et al., Molecular Cloning: A Laboratory Manual. 2$^{nd}$ Ed., Cold Spring Harbor, N.Y., 1989), which is supplemented with 50 mg/l kanamycin.

Plasmid DNA is isolated from a transformant with the aid of the QIAprep Spin Miniprep Kit from Qiagen and checked by restriction cleavage and subsequent agarose gel electrophoresis. The plasmid is called pK18mobsacBglu2.

As described in Example 2.1, a DNA fragment which carries the ddh gene and surrounding regions is also amplified with the aid of the polymerase chain reaction. On the basis of the sequence of the ddh gene cluster known for *C. glutamicum* (Ishino et al., Nucleic Acids Research 15, 3917 (1987)) (Accession Number Y00151), the following primer oligonucleotides are chosen for the PCR:

```
ddh_beg:
5' CTG AAT CAA AGG CGG ACA TG 3'     (SEQ ID NO: 15)

ddh_end:
5' TCG AGC TAA ATT AGA CGT CG 3'     (SEQ ID NO: 16)
```

The primers shown are synthesized by MWG Biotech and the PCR reaction is carried out by the standard PCR method of Innis et al. (PCR Protocols. A Guide to Methods and Applications, 1990, Academic Press). The primers allow amplification of a DNA fragment of approx 1.6 kb in size, which carries the ddh gene.

The amplified DNA fragment of approx. 1.6 kb in length, which the ddh gene, is identified by means of electrophoresis in a 0.8% agarose gel and isolated from the gel and purified by conventional methods (QIAquick Gel Extraction Kit, Qiagen, Hilden).

After purification, the fragment carrying the ddh gene is employed for ligation in the vector pK18mobsacBglu2 described. This is partly cleaved beforehand with the restriction enzyme BamHI. By treatment of the vector with a Klenow polymerase (Amersham-Pharmacia, Freiburg, Germany), the overhangs of the cleaved ends are completed to blunt ends, the vector is then mixed with the DNA fragment of approx. 1.6 kb which carries the ddh gene and the mixture is treated with T4 DNA ligase (Amersham-Pharmacia, Freiburg, Germany). By using Vent Polymerase (New England Biolabs, Frankfurt, Germany) for the PCR reaction, a ddh-carrying DNA fragment which has blunt ends and is suitable for ligation in the pretreated vector pK18mobsacBglu2 is generated.

The *E. coli* strain DH5αmcr (Life Technologies GmbH, Karlsruhe, Germany) is then transformed with the ligation batch (Hanahan, In: DNA Cloning. A Practical Approach. Vol. 1, ILR-Press, Cold Spring Harbor, N.Y., 1989). Selection of plasmid-carrying cells is made by plating out the transformation batch on LB agar (Sambrook et al., Molecular Cloning: A Laboratory Manual. $2^{nd}$ Ed., Cold Spring Harbor, N.Y., 1989), which was supplemented with 50 mg/l kanamycin.

Plasmid DNA is isolated from a transformant with the aid of the QIAprep Spin Miniprep Kit from Qiagen and checked by restriction cleavage and subsequent agarose gel electrophoresis. The plasmid is called pK18mobsacBglu2_1. A map of the plasmid is shown in FIG. 4.

2.2 Incorporation of a Second Copy of the ddh Gene into the Chromosome (Target Site: gluB Gene) of the Strain DSM12866 by Means of the Replacement Vector pK18mobsacBglu2_1

As described in Example 1.3, the plasmid pK18mobsacBglu2_1 described in Example 2.1 is transferred into the *C. glutamicum* strain DSM12866 by conjugation. Selection is made for targeted recombination events in the chromosome of *C. glutamicum* DSM12866 as described in Example 1.3. Depending on the position of the second recombination event, after the excision the second copy of the ddh gene manifests itself in the chromosome at the gluB locus, or the original gluB locus of the host remains.

Approximately 40 to 50 colonies are tested for the phenotype "growth in the presence of sucrose" and "non-growth in the presence of kanamycin". Approximately 20 colonies which show the phenotype "growth in the presence of sucrose" and "non-growth in the presence of kanamycin" are investigated with the aid of the polymerase chain reaction. A DNA fragment which carries the glu region described is amplified here from the chromosomal DNA of the colonies. The same primer oligonucleotides as are described in Example 2.1 for the construction of the replacement plasmid are chosen for the PCR.

```
gluA_beg:
5' CAC GGT TGC TCA TTG TAT CC 3'    (SEQ ID NO: 13)

gluD_end:
5' CGA GGC GAA TCA GAC TTC TT 3'    (SEQ ID NO: 14)
```

The primers allow amplification of a DNA fragment approx. 4.4 kb in size in control clones with the original glu locus. In clones with a second copy of the ddh gene in the chromosome at the gluB locus, DNA fragments with a size of approx. 6 kb are amplified.

The amplified DNA fragments are identified by means of electrophoresis in a 0.8% agarose gel.

A clone which, in addition to the copy present at the ddh locus, has a second copy of the ddh gene at the gluB locus in the chromosome was identified in this manner. This clone was called strain DSM12866glu::ddh.

EXAMPLE 3

Incorporation of a second copy of the dapA gene into the chromosome (target site: aecD gene) of the strain DSM12866

3.1 Construction of the Replacement Vector pK18mobsacBaecD2_1

The *Corynebacterium glutamicum* strain ATCC13032 is used as the donor for the chromosomal DNA. From the strain ATCC13032, chromosomal DNA is isolated using the conventional methods (Eikmanns et al., Microbiology 140: 1817–1828 (1994)). With the aid of the polymerase chain reaction, a DNA fragment which carries the aecD gene and surrounding regions is amplified. On the basis of the sequence of the aecD gene known for *C. glutamicum* (Rossol et al., Journal of Bacteriology 174:2968–2977 (1992)) (Accession Number M89931), the following primer oligonucleotides are chosen for the PCR:

```
aecD_beg:
5' GAA CTT ACG CCA AGC TGT TC 3'    (SEQ ID NO: 11)

aecD_end:
5' AGC ACC ACA ATC AAC GTG AG 3'    (SEQ ID NO: 12)
```

The primers shown are synthesized by MWG Biotech and the PCR reaction is carried out by the standard PCR method of Innis et al. (PCR Protocols. A Guide to Methods and Applications, 1990, Academic Press). The primers allow amplification of a DNA fragment of approx 2.1 kb in size, which carries the aecD gene and adjacent regions.

The amplified DNA fragment of approx. 2.1 kb in length is identified by means of electrophoresis in a 0.8% agarose gel and isolated from the gel and purified by conventional methods (QIAquick Gel Extraction Kit, Qiagen, Hilden).

The DNA fragment purified is cleaved with the restriction enzyme BglII and EcoRV (Amersham Pharmacia, Freiburg, Germany). The ligation of the fragment in the vector pUC18 then takes place (Norrander et al., Gene 26:101–106 (1983)). This is cleaved beforehand with the restriction enzymes BamHI and SmaI and dephosphorylated, mixed with the aecD-carrying fragment of approx. 1.5 kb, and the mixture is treated with T4 DNA Ligase (Amersham-Pharmacia, Freiburg, Germany). The ligation batch is transformed in the *E. coli* strain TOP10 (Invitrogen, Leek, The Netherlands). Selection of plasmid-carrying cells is made by plating out the transformation batch on kanamycin (50 mg/l)-containing LB agar with X-Gal (64 mg/l).

The plasmid obtained is checked by means of restriction cleavage, after isolation of the DNA, and identified in agarose gel. The resulting plasmid is called pUC18aecD.

With the aid of the polymerase chain reaction, a further DNA fragment which carries the dapA gene and surrounding regions is amplified. On the basis of the sequence of the dapA gene known for *C. glutamicum* (Bonassi et al., Nucleic Acids Research 18:6421 (1990)) (Accession Number X53993 and AX127149), the following primer oligonucleotides are chosen for the PCR:

```
dapA_beg:
5' CGA GCC AGT GAA CAT GCA GA 3'        (SEQ ID NO: 17)

dapA_end:
5' CTT GAG CAC CTT GCG CAG CA 3'        (SEQ ID NO: 18)
```

The primers shown are synthesized by MWG Biotech and the PCR reaction is carried out by the standard PCR method of Innis et al. (PCR Protocols. A Guide to Methods and Applications, 1990, Academic Press). The primers allow amplification of a DNA fragment of approx. 1.4 kb in size, which carries the dapA gene and adjacent regions.

The amplified DNA fragment of approx. 1.4 kb in length is identified by means of electrophoresis in a 0.8% agarose gel and isolated from the gel and purified by conventional methods (QIAquick Gel Extraction Kit, Qiagen, Hilden).

After purification, the dapA-containing DNA fragment approx. 1.4 kb in length is employed for ligation with the vector pUC18aecD described above. This is cleaved beforehand with the restriction enzyme StuI, mixed with the DNA fragment of approx. 1.4 kb, and the mixture is treated with T4 DNA Ligase (Amersham-Pharmacia, Freiburg, Germany).

The E. coli strain DH5αmcr (Life Technologies GmbH, Karlsruhe, Germany) is then transformed with the ligation batch (Hanahan, In: DNA Cloning. A Practical Approach. Vol. 1, ILR-Press, Cold Spring Harbor, N.Y., 1989). Selection of plasmid-carrying cells is made by plating out the transformation batch on LB agar (Sambrook et al., Molecular Cloning: A Laboratory Manual. $2^{nd}$ Ed., Cold Spring Harbor, N.Y., 1989), which was supplemented with 50 mg/l kanamycin.

Plasmid DNA is isolated from a transformant with the aid of the QIAprep Spin Miniprep Kit from Qiagen and checked by restriction cleavage and subsequent agarose gel electrophoresis. The plasmid is called pUC18aecD2.

The plasmid pUC18aecD2 is cleaved with the restriction enzyme SalI and partly with EcoRI (Amersham-Pharmacia, Freiburg, Germany) and after separation in an agarose gel (0.8%) with the aid of the QIAquick Gel Extraction Kit (Qiagen, Hilden, Germany) the fragment of approx. 2.7 kb which carries aecD and dapA is isolated from the agarose gel and employed for ligation with the mobilizable cloning vector pK18mobsacB described by Schäfer et al. (Gene 14: 69–73 (1994)). This is cleaved beforehand with the restriction enzymes EcoRI and with SalI and dephosphorylated with alkaline phosphatase (Alkaline Phosphatase, Boehringer Mannheim), mixed with the fragment of approx. 2.7 kb which carries aecD and dapA, and the mixture is treated with T4 DNA Ligase (Amersham-Pharmacia, Freiburg, Germany).

The E. coli strain DH5α (Grant et al.; Proceedings of the National Academy of Sciences USA, 87 (1990) 4645–4649) is then transformed with the ligation batch (Hanahan, In. DNA Cloning. A Practical Approach. Vol. 1, ILR-Press, Cold Spring Harbor, N.Y., 1989). Selection of plasmid-carrying cells is made by plating out the transformation batch on LB agar (Sambrook et al., Molecular Cloning: A Laboratory Manual. $2^{nd}$ Ed., Cold Spring Harbor, N.Y., 1989), which is supplemented with 50 mg/l kanamycin.

Plasmid DNA is isolated from a transformant with the aid of the QIAprep Spin Miniprep Kit from Qiagen and checked by restriction cleavage and subsequent agarose gel electrophoresis. The plasmid is called pK18mobsacBaecD2_1. A map of the plasmid is shown in FIG. 5.

3.2 Incorporation of a Second Copy of the dapA Gene into the Chromosome (Target Site: aecD Gene) of the Strain DSM12866 by Means of the Replacement Vector pK18mobsacBaecD2_1

As described in Example 1.3, the plasmid pK18mobsacBaecD2_1 described in Example 3.1 is transferred into the C. glutamicum strain DSM12866 by conjugation. Selection is made for targeted recombination events in the chromosome of C. glutamicum DSM12866 as described in Example 1.3.

Depending on the position of the second recombination event, after the excision the second copy of the dapA gene manifests itself in the chromosome at the aecD locus, or the original aecD locus of the host remains.

Approximately 40 to 50 colonies are tested for the phenotype "growth in the presence of sucrose" and "non-growth in the presence of kanamycin". Approximately 20 colonies which show the phenotype "growth in the presence of sucrose" and "non-growth in the presence of kanamycin" are investigated with the aid of the polymerase chain reaction. A DNA fragment which carries the aecD gene and surrounding regions is amplified here from the chromosomal DNA of the colonies. The same primer oligonucleotides as are described in Example 3.1 for the construction of the integration plasmid are chosen for the PCR.

```
aecD_beg:
5' GAA CTT ACG CCA AGC TGT TC 3'        (SEQ ID NO: 11)

aecD_end:
5' AGC ACC ACA ATC AAC GTG AG 3'        (SEQ ID NO: 12)
```

The primers allow amplification of a DNA fragment approx. 2.1 kb in size in control clones with the original aecD locus. In clones with a second copy of the dapA gene in the chromosome at the aecD locus, DNA fragments with a size of approx. 3.6 kb are amplified.

The amplified DNA fragments are identified by means of electrophoresis in a 0.8% agarose gel.

A clone which, in addition to the copy present at the dapA locus, has a second copy of the dapA gene at the aecD locus in the chromosome was identified in this manner. This clone was called strain DSM12866aecD::dapA.

EXAMPLE 4

Incorporation of a second copy of the pyc gene in the form of the pyc allele pycP458S into the chromosome (target site: pck gene) of the strain DSM12866

4.1 Construction of the Replacement Vector pK18mobsacBpck1_3

The replacement vector pK18mobsacBpck1 described in Example 1.5 is used as the base vector for insertion of the pyc allele.

As described in Example 2.1, a DNA fragment which carries the pyc gene and surrounding regions is also amplified with the aid of the polymerase chain reaction. On the basis of the sequence of the pyc gene cluster known for C. glutamicum (Peters-Wendisch et al., Journal of Microbiology 144: 915–927 (1998)) (Accession Number Y09548), the following primer oligonucleotides are chosen for the PCR:

```
pyc_beg:
                                          (SEQ ID NO: 19)
5' TC(A CGC GT)C TTG AAG TCG TGC AGG TCA G 3' pyc_end:
                                          (SEQ ID NO: 20)
5' TC(A CGC GT)C GCC TCC TCC ATG AGG AAG A 3'
```

The primers shown are synthesized by MWG Biotech and the PCR reaction is carried out by the standard PCR method of Innis et al. (PCR Protocols. A Guide to Methods and Applications, 1990, Academic Press). The primers allow amplification of a DNA fragment of approx 3.6 kb in size, which carries the pyc gene. The primers moreover contain the sequence for the cleavage site of the restriction endonuclease MluI, which is marked by parentheses in the nucleotide sequence shown above.

The amplified DNA fragment of approx. 3.6 kb in length, which carries the pyc gene, is cleaved with the restriction endonuclease MluI, identified by means of electrophoresis in a 0.8% agarose gel and isolated from the gel and purified by conventional methods (QIAquick Gel Extraction Kit, Qiagen, Hilden).

After purification, the fragment carrying the pyc gene is employed for ligation in the vector pK18mobsacBpck1 described. This is cleaved beforehand with the restriction enzyme BssHII, dephosphorylated with alkaline phosphatase (Alkaline Phosphatase, Boehringer Mannheim, Germany), mixed with the DNA fragment of approx. 3.6 kb which carries the pyc gene, and the mixture is treated with T4 DNA Ligase (Amersham-Pharmacia, Freiburg, Germany).

The *E. coli* strain DH5αmcr (Life Technologies GmbH, Karlsruhe, Germany) is then transformed with the ligation batch (Hanahan, In: DNA Cloning. A Practical Approach. Vol. 1, ILR-Press, Cold Spring Harbor, N.Y., 1989). Selection of plasmid-carrying cells is made by plating out the transformation batch on LB agar (Sambrook et al., Molecular Cloning: A Laboratory Manual. $2^{nd}$ Ed., Cold Spring Harbor, N.Y., 1989), which was supplemented with 50 mg/l kanamycin.

Plasmid DNA is isolated from a transformant with the aid of the QIAprep Spin Miniprep Kit from Qiagen and checked by restriction cleavage and subsequent agarose gel electrophoresis. The plasmid is called pK18mobsacBpck1_2.

4.2 Construction of the pyc Allele pyc P458S by Means of Site-specific Mutagenesis of the Wild-type pyc Gene The site-directed mutagenesis is carried out with the QuikChange Site-Directed Mutagenesis Kit (Stratagene, La Jolla, USA). EP-A-1108790 describes a point mutation in the pyc gene for *C. glutamicum* which allows improved L-lysine production. On the basis of the point mutation in the nucleotide sequence of cytosine to thymine in the pyc gene at position 1372, replacement in the amino acid sequence derived therefrom of proline for serine at position 458 results. The allele is called pyc P458S. To generate the mutation described, the following primer oligonucleotides are chosen for the linear amplification:

```
P458S-1:
                                          (SEQ ID NO: 21)
5' GGATTCATTGCCGATCAC (TCG) CACCTCCTTCAGGCTCCA 3'

P458S-2:
                                          (SEQ ID NO: 22)
5' GTGGAGGAAGTCCGAGGT (CGA) GTGATCGGCAATGAATCC 3'
```

The primers shown are synthesized by MWG Biotech. The codon for serine, which is to replace the proline at position 458, is marked by parentheses in the nucleotide sequence shown above. The plasmid pK18mobsacBpck1_2 described in Example 4.1 is employed with the two primers, which are each complementary to a strand of the plasmid, for linear amplification by means of Pfu Turbo DNA polymerase. By this lengthening of the primers, a mutated plasmid with broken circular strands is formed. The product of the linear amplification is treated with DpnI—this endonuclease cleaves the methylated and half-methylated template DNA specifically. The newly synthesized broken, mutated vector DNA is transformed in the *E. coli* strain XL1 Blue (Bullock, Fernandez and Short, BioTechniques (5) 376–379 (1987)). After the transformation, the XL1 Blue cells repair the breaks in the mutated plasmids. Selection of the transformants was carried out on LB medium with kanamycin 50 mg/l. The plasmid obtained is checked by means of restriction cleavage, after isolation of the DNA, and identified in agarose gel. The DNA sequence of the mutated DNA fragment is checked by sequencing. The sequence of the PCR product coincides with the sequence described Ohnishi et al. (2002). The resulting plasmid is called pK18mobsacBpck1_3. A map of the plasmid is shown in FIG. 6.

4.3 Incorporation of a Second Copy of the pyc Gene in the Form of the pyc Allele pycP458S into the Chromosome (Target Site pck Gene) of the Strain DSM12866 by Means of the Replacement Vector pk18mobsacBpck1_3

The plasmid pK18mobsacBpck1_3 described in Example 4.2 is transferred as described in Example 1.3 into the *C. glutamicum* strain DSM12866 by conjugation. Selection is made for targeted recombination events in the chromosome of *C. glutamicum* DSM12866 as described in Example 1.3. Depending on the position of the second recombination event, after the excision the second copy of the pyc allele manifests itself in the chromosome at the pck locus, or the original pck locus of the host remains.

Approximately 40 to 50 colonies are tested for the phenotype "growth in the presence of sucrose" and "non-growth in the presence of kanamycin". Approximately 20 colonies which show the phenotype "growth in the presence of sucrose" and "non-growth in the presence of kanamycin" are investigated with the aid of the polymerase chain reaction. A DNA fragment which carries the pck gene and surrounding regions is amplified here from the chromosomal DNA of the colonies. The same primer oligonucleotides as are described in Example 1.5 for the construction of the replacement plasmid are chosen for the PCR.

```
pck_beg:
                                          (SEQ ID NO: 9)
5' TA(A GAT CT) G CCG GCA TGA CTT CAG TTT 3' pck_end:
                                          (SEQ ID NO: 10)
5' AC(A GAT CT) G GTG GGA GCC TTT CTT GTT ATT 3'
```

The primers allow amplification of a DNA fragment approx. 2.9 kb in size in control clones with the original pck locus. In clones with a second copy of the pyc allele in the chromosome at the pck locus, DNA fragments with a size of approx. 6.5 kb are amplified.

The amplified DNA fragments are identified by means of electrophoresis in a 0.8% agarose gel.

A clone which, in addition to the copy of the wild-type gene present at the pyc locus, has a second copy of the pyc gene in the form of the pyc allele pycP458S at the pck locus in the chromosome was identified in this manner. This clone was called strain DSM12866pck::pyc.

EXAMPLE 5

Preparation of Lysine

The *C. glutamicum* strains DSM13994glu::lysC, DSM12866glu::lysC, DSM12866pck::lysC, DSM12866aecD::lysC, DSM12866glu::ddh, DSM12866aecD::dapA and DSM12866pck::pyc obtained in Example 1, 2, 3 and 4 are cultured in a nutrient medium suitable for the production of lysine and the lysine content in the culture supernatant was determined.

For this, the cultures are first incubated on a brain-heart agar plate (Merck, Darmstadt, Germany) for 24 hours at 33° C. Starting from this agar plate culture, a preculture is seeded (10 ml medium in a 100 ml conical flask). The medium MM is used as the medium for the preculture. The preculture is incubated for 24 hours at 33° C. at 240 rpm on a shaking machine. A main culture is seeded from this preculture such that the initial OD (660 nm) of the main culture is 0.1 OD. The Medium MM is also used for the main culture.

| Medium MM | |
|---|---|
| CSL | 5 g/l |
| MOPS | 20 g/l |
| Glucose (autoclaved separately) | 50 g/l |
| Salts: | |
| $(NH_4)_2SO_4$ | 25 g/l |
| $KH_2PO_4$ | 0.1 g/l |
| $MgSO_4 * 7 H_2O$ | 1.0 g/l |
| $CaCl_2 * 2 H_2O$ | 10 mg/l |
| $FeSO_4 * 7 H_2O$ | 10 mg/l |
| $MnSO_4 * H_2O$ | 5.0 mg/l |
| Biotin (sterile-filtered) | 0.3 mg/l |
| Thiamine * HCl (sterile-filtered) | 0.2 mg/l |
| $CaCO_3$ | 25 g/l |

The CSL (corn steep liquor), MOPS (morpholinopropanesulfonic acid) and the salt solution are brought to pH 7 with aqueous ammonia and autoclaved. The sterile substrate and vitamin solutions, as well as the $CaCO_3$ autoclaved in the dry state, are then added.

Culturing is carried out in a 10 ml volume in a 100 ml conical flask with baffles. Culturing is carried out at 33° C. and 80% atmospheric humidity.

After 48 hours, the OD is determined at a measurement wavelength of 660 nm with a Biomek 1000 (Beckmann Instruments GmbH, Munich). The amount of lysine formed is determined with an amino acid analyzer from Eppendorf-BioTronik (Hamburg, Germany) by ion exchange chromatography and post-column derivation with ninhydrin detection.

The result of the experiment is shown in Table 14.

TABLE 14

| Strain | OD (660 nm) | Lysine HCl g/l |
|---|---|---|
| DSM13994 | 12.0 | 19.1 |
| DSM13994glu::lysC | 9.9 | 20.0 |
| DSM12866 | 12.5 | 14.9 |
| DSM15039 | 11.4 | 16.2 |
| DSM12866pck::lysC | 12.6 | 16.5 |
| DSM12866aecD::lysC | 12.0 | 15.9 |
| DSM12866glu::ddh | 11.0 | 15.5 |
| DSM12866aecD::dapA | 11.1 | 16.2 |
| DSM12866pck::pyc | 10.9 | 16.9 |

EXAMPLE 6

Integration of a copy of the lysC$_{-T}$311I allele into the intergenic area ncode1 of the chromosome of the strain DSM13992

6.1 Construction of the Exchange Vector pK18mobsacBnc1::lysC

The *Corynebacterium glutamicum* strain DSM13994 (see example 1) is used as a donor for the chromosomal DNA. Chromosomal DNA is isolated from the strain DSM13994 with the customary methods (Eikmanns et al., Microbiology 140: 1817–1828 (1994). With the help of the polymerase chain reaction (PCR), a DNA fragment which encompasses an intergenic area of the chromosome labelled as "ncode1" (SEQ ID NO: 23) is amplified. This area lies within the positions 27398 to 28707 of the sequence of the *Corynebacterium glutamicum* genome, which is accessible under the access code AX127149 (see table 12). Due to the known sequence of this area, the following primer oligonucleotides are selected for the PCR:

```
Primer ncode_1:
5' GA(A GAT CT)A AGC TCT ATT GTC CCC TAC G 3'                         (SEQ ID NO: 24)

Primer ncode_2:
5' GAT CCT TTT AAA AGC CAG TAA CAA G 3'                                (SEQ ID NO: 25)

Primer ncode_3:
5' CTT GTT ACT GGC TTT AAA AAG GAT CCT ATT AAA GAA CAC TCC CCT AT 3'   (SEQ ID NO: 26)

Primer ncode_4:
5' GA(A GAT CT)C GAC TCT GGC TAA TTG CTA C 3'                          (SEQ ID NO: 27)
```

The primers shown are synthesized by the company MWG Biotech and the PCR reaction is carried out using the standard PCR method of Innis et al. (PCR protocols. A guide to methods and applications, 1990, Academic Press), in which first two products are amplified with the primer combinations ncode_1 and ncode_2 or ncode_3 and ncode_4, which then serve as a template for the primer combination ncode_1 and ncode_4 together in a second PCR. In this manner, the selected primers enable the amplification of an approx. 1.2 kb sized DNA fragment which bears an artificially created interface of the restriction endonuclease BamHI in the center of the intergenic area (emphasized by underlining, (SEQ ID NO: 28)). Furthermore, the primers contain the sequence for the interface of the restriction endonuclease BglII, which is marked with brackets in the nucleotide series shown above.

The amplified DNA fragment of a length of approx. 1.2 kb which bears the intergenic area ncode1 is identified by means of electrophoresis in an 0.8% agarose gel and is isolated from the gel and cleaned using the customary methods (QIAquick Gel Extraction Kit, Qiagen, Hilden).

Next, the ligation of the fragment using the Topo TA Cloning Kit (Invitrogen, Leek, Netherlands, Cat. Number K4600-01) into the vector pCRII-TOPO takes place. The ligation culture is transformed into the *E. coli* strain TOP10 (Invitrogen, Leek, Netherlands). The selection of plasmide-bearing cells takes place through plating of the transformation culture onto Kanamycin (50 mg/l)-containing LB agar with X-Gal (64 mg/l),.

Following isolation of the DNA, the plasmide thus obtained is verified using restriction splitting and identified in the agarose gel. The plasmide obtained is called pCRII-TOPOnc.

The plasmide pCRII-TOPOnc is cut with the restriction enzyme BglII (Amersham-Pharmarcia, Freiburg, Germany), and following splitting in an agarose gel (0.8%), the approx. 1.2 kb fragment is isolated out of the agarose gel with the aid of the Qiagenquick Gel Extraction Kit (Qiagen, Hilden, Germany) and used for ligation with the mobilizable cloning vector pK18mobsacB described in Schäfer et al. (Gene 14, 69–73 (1994)). This is first split with the restriction enzyme BamHI and dephosphorylized with alkaline phosphatase (Alkaline Phosphatase, Boehringer Mannheim), mixed with the approx. 1.2 kb fragment and the culture is treated with T4-DNA ligase (Amersham-Pharmacia, Freiburg, Germany).

Following this, the *E.coli* strain DH5α (Grant et al.; Proceedings of the National Academy of Sciences USA, 87 (1990) 4645–4649) is transformed with the ligation culture (Hanahan, In. DNA cloning. A practical approach. Vol. 1. ILR-Press, Cold Spring Harbor, N.Y., 1989). The selection of the plasmide-bearing cells takes place through plating of the transformation cultures onto LB agar (Sambrock et al., Molecular Cloning: a laboratory manual. $2^{nd}$ Ed. Cold Spring Harbor, N.Y., 1989) which is supplemented with 25 mg/l Kanamycin.

Plasmide DNA is isolated from a transformant with the aid of the QIAprep Spin Miniprep Kit from the company Qiagen and verified using restriction splitting with the enzyme XbaI and following agarose gel electrophoresis. The plasmide is called pK18mobsacBnc.

The plasmide pCRIITOPOlysC described in example 1 is cut using the restriction enzyme BamHI (Amersham-Pharmarcia, Freiburg, Germany). Following splitting in an agarose gel (0.8%) with the aid of the Qiagenquick Gel Extraction Kit (Qiagen, Hilden, Germany), the approx. 1.7 kb long, lysC$_{-T}$311I containing DNA fragment is isolated out of the agarose gel and used for ligation with the vector pK18mobsacBnc described above. This is first split with the restriction enzyme BamHI, dephosphorylized with alkaline phosphatase (Alkaline Phosphatase, Boehringer Mannheim, Germany), mixed with the approx. 1.7 kb DNA fragment and the culture is treated with T4-DNA ligase (Amersham-Pharmacia, Freiburg, Germany).

Following this, the *E.coli* Strain DH5αmcr (Life Technologies GmbH, Karlsruhe, Germany) is transformed using the ligation culture (Hanahan, In. DNA cloning. A practical approach. Vol. 1. ILR-Press, Cold Spring Harbor, N.Y., 1989). The selection of the plasmide-bearing cells takes place through plating of the transformation culture onto LB agar (Sambrock et al., Molecular Cloning: a laboratory manual. $2^{nd}$ Ed. Cold Spring Harbor, N.Y., 1989), which was supplemented with 25 mg/l Kanamycin.

Plasmide DNA is isolated from a transformant with the aid of the QIAprep Spin Miniprep Kit from the company Qiagen isolated and verified through restriction splitting with the enzymes HindIII and XbaI and following agarose gel electrophoresis. The plasmide is called pK18mobsacBnc::lysC. A card of the plasmide is shown in FIG. 7.

6.2 Integration of a Second Copy of the lysC Gene in the Form of the lysC$^{FBR}$m Allele lysC T311I into the Chromosome (Target Site: the Intergenic Area ncode1) of the Strain DSM13992, Using the Exchange Vector pK18mobsacBnc::lysC The vector pK18mobsacBnc::lysC named in example 6.1 is transferred into the *C. glutamicum* strain DSM13992 according to a modified protocol of Schäfer et al.(1990 Journal of Microbiology 172: 1663–1666).

The *Corynebacterium glutamicum* strain DSM13992 was manufactured by repeated, undirected mutagenesis, selection and mutant selection from *C. glutamicum* ATCC13032. The strain is resistant to the antibiotic Streptomycin and phenotypically resistant to the lysine analogon S-(2-Aminoethyl)-L-Cystein. However, the strain has a wild-type aspartate kinase which is sensitive to inhibition by a mixture of lysine and therein (25 mM each). A pure culture of this strain was filed on Jan. 16, 2001 with the Deutsche Sammlung für Mikroorganismen und Zellkulturen [=German Collection of Microorganisms and Cell Cultures] (DSMZ, Braunschweig, Germany) in accordance with the Budapest Convention.

The vector pK18mobsacBnc::lysC cannot replicate independently in DSM13992 and only remains in the cell if it has integrated into the chromosome through recombination.

The selection of clones with integrated pK18mobsacBnc::lysC takes place through plating of the conjugation culture onto LB agar (Sambrook et al., Molecular Cloning: A Laboratory Manual. $2^{nd}$ Ed., Cold Spring Harbor, N.Y., 1989) which was supplemented with 15 mg/l Kanamycin and 50 mg/l nalidixin acid. Clones that have begun to grow are plated onto LB agar plates with 25 mg/l Kanamycin and incubated for 16 hours at 33° C. To bring about the excision of the plasmide through a second recombination event, the clones are started with 10% sucrose after the 16-hour incubation in the LB liquid medium. The plasmide pK18mobsacB contains a copy of the sacB gene, which changes sucrose into levan, which in turn is toxic to *C. glutamicum*.

Consequently, only clones in which the integrated pK18mobsacBnc::lysC has excised again grow on LB agar with sucrose. In dependency from the position of the second recombination event, during excision, either the copy of the lysC with the surrounding intergenic area ncode1 will excise together with the plasmide, or only the intergenic area ncode1 will excise.

In order to prove that the copy of lysC has remained in the intergenic area ncode1 of the chromosome, approximately 20 colonies which show the phenotype "Growth in the Presence of Sucrose" and "Non-Growth in the Presence of Kanamycin" according to the standard PCR method of Innis et al. (PCR Protocols. A Guide to Methods and Applications, 1990, Academic Press) are researched with the aid of the polymerase chain reaction. In this, a DNA fragment from the chromosomal colonies of the DNA which carries the lysC gene as well as the surrounding areas is amplified. The following primer oligonucleotides are selected for the PCR.

```
3371V:
5' TAT CAT GCG GTG AGC TGT GA 3'    (SEQ ID NO: 29)

3372N:
5' TAG GGG TGA TGT GCT ACT GT 3'    (SEQ ID NO: 30)
```

In control clones with the original ncode1 location, the primers enable the amplification of an approx. 1.3 kb sized DNA fragment. In clones with a copy of the lysC gene in the intergenic area ncode1 of the chromosome, DNA fragments with a size of approx. 3.0 kb are amplified.

The amplified DNA fragments are identified using electrophoresis in an 0.8% agarose gel.

In this manner, a clone was identified which in addition to the copy existing in the lysC location, has a second copy of the lysC$^{FBR}$ allele lysC T311I in the intergenic area ncode1 in the chromosome. This clone was named as the strain DSM13992nc::lysC.

BRIEF DESCRIPTION OF THE FIGURES

The base pair numbers stated are approximate values obtained in the context of reproducibility of measurements.

FIG. 1: Map of the plasmid pK18mobsacBglu1_1.

The abbreviations and designations used have the following meaning:

| KanR: | Kanamycin resistance gene |
|---|---|
| HindIII: | Cleavage site of the restriction enzyme HindIII |
| BamHI: | Cleavage site of the restriction enzyme BamHI |
| lysC: | lysC$^{FBR}$ allele, lysC T311I |
| 'gluA: | 3' terminal fragment of the gluA gene |
| gluB': | 5' terminal fragment of the gluB gene |
| 'gluB: | 3' terminal fragment of the gluB gene |
| gluC': | 5' terminal fragment of the gluC gene |
| sacB: | sacB gene |
| RP4mob: | mob region with the replication origin for the transfer (oriT) |
| oriV: | Replication origin V |

FIG. 2: Map of the plasmid pK18mobsacBaecD1_1.

The abbreviations and designations used have the following meaning:

| KanR: | Kanamycin resistance gene |
|---|---|
| SalI: | Cleavage site of the restriction enzyme SalI |
| lysC: | lysC$^{FBR}$ allele, lysC T311I |
| aecD': | 5' terminal fragment of the aecD gene |
| 'aecD: | 3' terminal fragment of the aecD gene |
| sacB: | sacB gene |
| RP4mob: | mob region with the replication origin for the transfer (oriT) |
| oriV: | Replication origin V |

FIG. 3: Map of the plasmid pK18mobsacBpck1_1.

The abbreviations and designations used have the following meaning:

| KanR: | Kanamycin resistance gene |
|---|---|
| BamHI: | Cleavage site of the restriction enzyme BamHI |
| lysC: | lysC$^{FBR}$ allele, lysC T311I |
| pck': | 5' terminal fragment of the pck gene |
| 'pck: | 3' terminal fragment of the pck gene |
| sacB: | sacB gene |
| RP4mob: | mob region with the replication origin for the transfer (oriT) |
| oriV: | Replication origin V |

FIG. 4: Map of the plasmid pK18mobsacBgluB2_1.

The abbreviations and designations used have the following meaning:

| KanR: | Kanamycin resistance gene |
|---|---|
| SalI | Cleavage site of the restriction enzyme SalI |
| EcoRI | Cleavage site of the restriction enzyme EcoRI |
| BamHI: | Cleavage site of the restriction enzyme BamHI |
| ddh: | ddh gene |
| gluA | gluA gene |
| gluB': | 5' terminal fragment of the gluB gene |
| 'gluB: | 3' terminal fragment of the gluB gene |
| gluC | gluC gene |
| gluD': | 5' terminal fragment of the gluD gene |
| sacB: | sacB gene |
| RP4mob: | mob region with the replication origin for the transfer (oriT) |
| oriV: | Replication origin V |

FIG. 5: Map of the plasmid pK18mobsacBaecD2_1.

The abbreviations and designations used have the following meaning:

| KanR: | Kanamycin resistance gene |
|---|---|
| EcoRI | Cleavage site of the restriction enzyme EcoRI |
| SalI: | Cleavage site of the restriction enzyme SalI |
| dapA: | dapA gene |
| aecD': | 5' terminal fragment of the aecD gene |
| 'aecD: | 3' terminal fragment of the aecD gene |
| sacB: | sacB gene |
| RP4mob: | mob region with the replication origin for the transfer (oriT) |
| oriV: | Replication origin V |

FIG. 6: Map of the plasmid pK18mobsacBpck1_3.

The abbreviations and designations used have the following meaning:

| KanR: | Kanamycin resistance gene |
|---|---|
| pyc: | pyc allele, pyc P458S |
| pck': | 5' terminal fragment of the pck gene |
| 'pck: | 3' terminal fragment of the pck gene |
| sacB: | sacB gene |
| RP4mob: | mob region with the replication origin for the transfer (oriT) |
| oriV: | Replication origin V |

FIG. 7: Map of the plasmid pK18mobsacBnc::lysC
The abbreviations and designations used have the following meaning:

| | |
|---|---|
| KanR: | Kanamycin resistance gene |
| BamHI: | Cleavage site of the restriction enzyme BamHI |
| HindIII: | Cleavage site of the restriction enzyme HindIII |
| XbaI | Cleavage site of the restriction enzyme XbaI |
| lysC: | lysC$^{FBR}$ allele, lysC T311I |
| sacB: | sacB gene |
| RP4mob: | mob region with the replication origin for the transfer (oriT) |
| oriV: | Replication origin V |

What is claimed is:

1. A coryneform bacterium comprising two or more copies of a coryneform gene selected from the group consisting of accBC, accDA, cstA, cysD, cysE, cysH, cysK, cysN, cysQ, dapB, dapC, dapD, dapE, dapF, ddh, dps, eno, gap, gap2, gdh, gnd, lysC, lysC$^{FBR}$, lysE, msiK, opcA, oxyR, ppc, ppc$^{FBR}$, pgk, pknA, pknB, pknD, pknG, ppsA, ptsH, ptsI, ptsM, pyc, pyc P458S, sigC, sigD, sigE, sigH, sigM, tal, thyA, tkt, tpi, zwa1, zwf and zwf A213T within the bacterium's chromosome, wherein said coryneform gene contains no nucleotide sequence encoding antibiotic resistance, wherein said coryneform bacterium produces enhanced levels of L-amino acid over a coryneform bacterium having one copy of said coryneform gene.

2. The coryneform bacterium of claim 1, wherein at least one coryneform gene selected from the group consisting of accBC, accDA, cstA, cysD, cysE, cysH, cysK, cysN, cysQ, dapB, dapC, dapD, dapE, dapF, ddh, dps, eno, gap, gap2, gdh, gnd, lysC, lysC$^{FBR}$, lysE, msiK, opcA, oxyR, ppc, ppc$^{FBR}$, pgk, pknA, pknB, pknD, pknG, ppsA, ptsH, ptsI, ptsM, pyc, pyc P458S, sigC, sigD, sigE, sigH, sigM, tal, thyA, tkt, tpi, zwa1, zwf and zwf A213T is inserted into one or more coryneform chromosomal sites selected from the group consisting of ccpA1, ccpA2, citA, citB, citE, fda, gluA, gluB, gluC, gluD, luxR, luxS, lysR1, lysR2, lysR3, menE, mqo, pck, pgi, and poxB.

3. The coryneform bacterium of claim 1, wherein the L-amino acid produced is selected from the group consisting of L-aspartic acid, L-asparagine, L-threonine, L-serine, L-glutamic acid, L-glutamine, glycine, L-alanine, L-cysteine, L-valine, L-methionine, L-isoleucine, L-leucine, L-tyrosine, L-phenylalanine, L-histidine, L-lysine, L-tryptophan, L-proline and L-arginine.

4. The coryneform bacterium of claim 3, wherein the L-amino acid produced is L-lysine.

5. The coryneform bacterium of claim 3, wherein two or more copies of a lysC$^{FBR}$ variant gene are within the bacterium chromosome, wherein said lysC$^{FBR}$ variant gene is encoded by one or more amino acid substitutions selected from the group consisting of A279T, A279V, S301F, T308I, S301Y, G345D, R320G, T311I, and S381F of an amino acid sequence as set forth in SEQ ID NO: 2, wherein said coryneform bacterium produced enhanced levels of L-amino acid over a coryneform bacterium having one copy of said lysC$^{FBR}$ variant gene.

6. The coryneform bacterium of claim 1, wherein the coryneform bacterium is a member of the genus of *Corynebacterium*.

7. The coryneform bacterium of claim 1, wherein the *Corynebacterium* is a *Corynebacterium glutamicum*.

8. The coryneform bacterium of claim 1, wherein no nucleotide sequences of said genes is capable of episomal replication in the coryneform bacterium.

9. The coryneform bacterium of claim 1, wherein no nucleotide sequence of said gene is capable of transposition.

10. The coryneform bacterium of claim 1, wherein no nucleotide sequence imparts resistance to antibiotics within the chromosome.

11. The coryneform bacterium of claim 1, wherein at least one copy of said gene is inserted in an intergenic region of the chromosome, a target site for a prophage nucleotide sequence contained within the chromosome, or a target site for a defective phage nucleotide sequence contained within the chromosome.

12. The coryneform bacterium of claim 11, wherein the intergenic region of the *C. glutamicum* chromosome is selected from the group consisting of nucleotide positions 192,176 to 194,501; 235,840 to 237,311; 236,096 to 237,311; 322,628 to 330,877; 334,045 to 336,467; 289,565 to 291,841; 154,823 to 161,111; 190,088 to 193,497; 27,390 to 28,707; 61,478 to 62,944; 116,234 to 117,561; 140,847 to 144,605; 113,274 to 114,324; and 244,281 to 246,403.

13. The coryneform bacterium of claim 11, wherein the target site of prophage and defective prophages suitable for integration of open reading frames, genes or alleles within a *C. glutamicum* chromosome are selected from the group consisting of nucleotide positions 50,474 to 51,049; 67,886 to 68,587; 72,893 to 73,480; 88,231 to 89,445; 139,781 to 140,155; 140,546 to 141,001; 194,608 to 1952294; 200,185 to 200,940; 208,157 to 208,450; 269,616 to 269,948; 336,468 to 338,324; 342,235 to 342,681; 343,518 to 345,356; and 345,872 to 346,207.

14. A plasmid designated pK18mobsacBglu1__1 as shown in FIG. 1 and deposited in the form of a pure culture of the strain *E. coli* DH5.alpha.mcr/pK18mobsacBglu1__1 (=DH5alpha mcr/pK18mobsacBglu1__1) under number DSM14243.

15. A plasmid designated Plasmid pK18mobsacBaecD1.__1 shown in FIG. 2 and deposited in the form of a pure culture of the strain *E. coli* DH5.alpha.mcr/pK18mobsacBaec-D1__1 (=DH5alphamcr/pK18mobsacBaecD1__1) under number DSM15040.

16. A *Corynebacterium glutamicum* strain DSM12866glu::lysC deposited in the form of a pure culture under number DSM15039.

* * * * *